US012774475B2

(12) United States Patent
Ward et al.

(10) Patent No.: US 12,774,475 B2
(45) Date of Patent: Oct. 27, 2026

(54) COMPOSITIONS AND METHODS FOR PRODUCING RECOMBINANT AAV

(71) Applicant: Sangamo Therapeutics, Inc., Brisbane, CA (US)

(72) Inventors: Alex Michael Ward, El Cerrito, CA (US); Hung Tran, San Francisco, CA (US); Andrea J. Kang, San Carlos, CA (US); Tzu-Hung Chen, Berkeley, CA (US); Richard T. Surosky, Oakland, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 1037 days.

(21) Appl. No.: 17/777,723

(22) PCT Filed: Dec. 4, 2020

(86) PCT No.: PCT/US2020/063481
§ 371 (c)(1),
(2) Date: May 18, 2022

(87) PCT Pub. No.: WO2021/113767
PCT Pub. Date: Jun. 10, 2021

(65) Prior Publication Data

US 2023/0020565 A1 Jan. 19, 2023

Related U.S. Application Data

(60) Provisional application No. 62/943,715, filed on Dec. 4, 2019.

(51) Int. Cl.
*C12N 15/86* (2006.01)
*C07K 14/005* (2006.01)
*C12N 5/07* (2010.01)

(52) U.S. Cl.
CPC ............ *C12N 15/86* (2013.01); *C07K 14/005* (2013.01); *C12N 5/0601* (2013.01)

(58) Field of Classification Search
CPC ..... C12N 15/86; C12N 5/0601; C07K 14/005
See application file for complete search history.

(56) References Cited

U.S. PATENT DOCUMENTS

| | | | | |
|---|---|---|---|---|
| 11,306,291 | B2 * | 4/2022 | Bakker | C12N 7/00 |
| 2003/0148506 | A1 | 8/2003 | Kotin et al. | |
| 2004/0197895 | A1 * | 10/2004 | Kotin | C12N 7/00 435/235.1 |
| 2009/0191597 | A1 | 7/2009 | Samulski et al. | |
| 2011/0236353 | A1 * | 9/2011 | Wilson | A61K 48/00 424/93.2 |

FOREIGN PATENT DOCUMENTS

| | | | | |
|---|---|---|---|---|
| CN | 111183225 | A | 5/2020 | |
| CN | 113728108 | A | 11/2021 | |
| JP | 2009540823 | A | 11/2009 | |
| JP | 2017506898 | A | 11/2019 | |
| WO | 2003042361 | A2 | 5/2003 | |
| WO | 2007084773 | A2 | 7/2007 | |
| WO | 2019016349 | A1 | 1/2019 | |
| WO | WO 2019/221992 | A1 * | 11/2019 | A61K 31/7088 |

OTHER PUBLICATIONS

Valdmanis, P.N. and Kay, M.A., 2017. Future of rAAV gene therapy: platform for RNAi, gene editing, and beyond. Human Gene Therapy, 28(4), pp. 361-372. (Year: 2017).*

CN: First Office Action dated Jun. 5, 2024 for Application No. 202080084068.6 Machine Translation.

EP: First Examination Report in European Application No. 20829463.7 dated Dec. 13, 2024 (7 pages).

Im et al., "Partial purification of adeno-associated virus Rep78, Rep52, and Rep40 and their biochemical characterization." J Virol. Feb. 1992;66(2):1119-28. doi: 10.1128/JVI.66.2.1119-1128.1992. PMID: 1309894; PMCID: PMC240816.

JP: Decision to Grant JP Application No. 2022-533493 dated May 7, 2025 (5 pages) English Translation.

JP: Notice of Reasons for Refusal in JP Application No. 2022-533493 dated Oct. 1, 2024 (12 pages) English Translation.

Kohlbrenner et al. "Successful Production of Pseudotyped rAAV Vectors Using a Modified Baculovirus Expression System" Molecular Therapy 12(6): pp. 1217-1225 (2005).

TW: Office Action in Taiwan Application No. 109142971 dated Aug. 20, 2014 (17 pages) Machine Translation.

WO: International Preliminary Report on Patentability in PCT/US2020/063481 dated May 17, 2022 (6 pages).

WO: International Search Report and Written Opinion in PCT/US2020/063481 dated Mar. 12, 2021 (10 pages).

Xia, "Study on production of recombinant adeno-associated virus for gene therapy using insect cell expression system." China Excellent Master's Degree Theses Full-text Database (Electronic Journal) Feb. 15, 2013.

AU: Office Action in Application No. 2020398178 dated Jan. 30, 2026 (3 pages).

CN: Second Office Action in Application No. 202080084068.6 dated Sep. 30, 2025 (Machine Translation).

KR: Office Action in Application No. 10-2022-7022189 dated Oct. 29, 2025 (Machine Translation).

Marwidi et al., "A robust and flexible baculovirus-insect cell system for AAV vector production with improved yield, capsid ratios and potency." Mol Ther Methods Clin Dev. Mar. 4, 2024;32(2):101228. doi: 10.1016/j.omtm.2024.101228. PMID: 38524756; PMCID: PMC10959708.

SG: Written Opinion in Application No. 11202205393Y dated Aug. 5, 2025 (8 pages).

* cited by examiner

*Primary Examiner* — Titilayo Moloye
*Assistant Examiner* — Risa Takenaka
(74) *Attorney, Agent, or Firm* — Snell & Wilmer, L.L.P.; April Wurster

(57) ABSTRACT

Provided herein are nucleic acid constructs, host insect cells, and methods for producing recombinant AAV capsids with high potency at high yield.

20 Claims, 8 Drawing Sheets

Specification includes a Sequence Listing.

| | Position | | | | | | | | | | | | | | |
|---|---|---|---|---|---|---|---|---|---|---|---|---|---|---|---|
| Serotype | 158 | 160 | 163 | 165 | 169 | 171 | 173 | 175 | 176 | 177 | 178 | 179 | 180 | 181 | 182 |
| 1 | S158 T/A | I160 T/V | T163 A/S/K | Q165 K/A | K169R | | | | | | | | S180 A/T | | |
| 4 | T158S /A | I160 T/V | K163 A/S | K165 Q/A | K169R | K171R | V173N | E175G | D176 Q/E | E177T | T178G | G179 D/E | A180 S/T | G181 D/E | D182S |
| 6 | S158 T/A | I160T /V | T163 A/S/K | Q165 K/A | K169R | | | | | | | | S180 A/T | | |
| 7 | T158 S/A | I160T T/V | K163 A/S | Q165 K/A | R169K | | | | | | | | S180 A/T | | |
| 8 | T158 S/A | I160T /V | K163 A/S | Q165 K/A | R169K | | | | | | | | S180 A/T | | |
| 11 | S158 T/A | I160T /V | K163 A/S | K165 Q/A | R169K | | | E175G | E176Q | D177T | T178G | G179 D/E | A180 S/T | G181 D/E | D182S |

| | Position | | | | | | | | | | | | | | |
|---|---|---|---|---|---|---|---|---|---|---|---|---|---|---|---|
| Serotype | 183 | 189 | 191 | 192 | 193 | 194 | 195 | 196 | 197 | 198 | 199 | 200 | 201 | 202 | 203 |
| 1 | | L189 E/I | | | | | T195A | | A197 S/T | A198S/ G | V199L | | P201T/ S | T202 N/L | |
| 4 | G183V | E189 L/I | S191 Q/E | T192P | S193P | G194A | | M196P | S197T | | | D200G | D201T /S | S202 N/L | E203T |
| 6 | | L189 E/I | | | | | T195A | | A197 S/T | A198S/ G | V199L | | P201T/ S | T202N /L | |
| 7 | | L189 E/I | | | | | | | S197T | S198G | V199L | | | G202 N/L | |
| 8 | | L189 E/I | | | | | | | S197T | G198S | V199L | | P201T/ S | N202L | |
| 11 | G183V | E189 L/I | S191 Q/E | D192P | T193P | S194A | | M196P | S197T | | | S200G | D201 T/S | I202 N/L | E203T |

FIG. 1C

| | Position | | | | | | | | | | | | |
|---|---|---|---|---|---|---|---|---|---|---|---|---|---|
| Serotype | 2 | 3 | 4 | 5 | 6 | 7 | 8 | 9 | 10 | 11 | 12 | 13 | 14 |
| 1 | | | | | | | P8Q | I9T | H10L | | L12Q | | |
| 2 | E2A | | | T5S | | Y7S | L8Q | | P10L | S11N | L12Q | | D14E |
| 4 | E2A | Q3T | A4Q | T5S | D6Q | P7S | | | | | L12Q | R13S | D14E |
| 6 | | | | | | | P8Q | | H10L | | L12Q | | |
| 7 | | | | | | | P8Q | | | | L12Q | | |
| 8 | | | | | | F7S | | | | | L12Q | | |
| 10 | | S3T | | | | | P8Q | | | | Q12L | | |
| 11 | E2A | P3T | E4Q | T5S | D6Q | P7S | | | | | L12Q | R13S | D14E |

| | Position | | | | | | | | | | | | |
|---|---|---|---|---|---|---|---|---|---|---|---|---|---|
| Serotype | 15 | 16 | 17 | 18 | 19 | 21 | 22 | 23 | 24 | 25 | 26 | 27 | 28 |
| 1 | | L16H | Q17P | | | L21Q | L22V | | | | L26I | | |
| 2 | S15N | H16L | Q17P | | | L21Q | | | E24D | | I26L | R27Q | |
| 4 | Q15N | L16H | P17Q | E18Q | | | C22V | L23W | M24D | T25L | V26I/L | R27Q | C28W |
| 6 | | L16H | Q17P | | | L21Q | L22V | | | | L26I | | |
| 7 | | L16H | Q17P | | R19P | L21Q | | | | | V26I/L | | |
| 8 | | L16H | Q17P | | R19P | L21Q | | | | | I26L | | |
| 10 | | L16H | Q17P | | A19P | L21Q | | | | | V26I/L | | |
| 11 | Q15N | I16L/H | P17Q | A18Q | | | C22V | L23W | Q24D | T25L | L26I | K27Q | C28W |

FIG. 4B

COMPOSITIONS AND METHODS FOR PRODUCING RECOMBINANT AAV

CROSS REFERENCE TO RELATED APPLICATIONS

The present application claims priority from U.S. Provisional Application 62/943,715, filed Dec. 4, 2019, the content of which is incorporated herein by reference in its entirety.

SEQUENCE LISTING

The instant application contains a Sequence Listing that has been submitted electronically in ASCII format. The Sequence Listing is hereby incorporated by reference in its entirety. The ASCII copy, created on Nov. 30, 2020, is named 025297_WO015_SL.txt and is 111,015 bytes in size.

BACKGROUND OF THE INVENTION

Adeno-associated virus (AAV) is a small non-enveloped virus belonging to the family Parvoviridae and the genus *Dependoparvovirus*. AAV is composed of a single-stranded DNA genome packaged into capsids assembled from three capsid proteins—viral protein (VP) 1, VP2, and VP3—at an approximate molar ratio of 1:1:10 (Berns and Parrish (2007) Parvoviridae in Fields Virology (Knipe and Howley, eds., 5th ed. Philadelphia: Wolters Kluwer Health/Lippincott Williams & Wilkins); Wang et al., *Nat Rev Drug Discov.* (2019) 18(5):358-78). The capsid proteins are encoded by a single capsid (cap) gene and are generated by alternative splicing and differential codon usage (id.). VP1 is the largest capsid protein (81.6 kD). VP2 (66.6 kD) is an N-terminal truncated form of VP1. VP3 (59.9 kD) is an N-terminal truncated form of VP2. See, e.g., Cecchini et al., *Hum Gene Ther.* (2011) 22:1021-30.

Recombinant AAV (rAAV) has been intensively explored as a vector for gene therapy and DNA vaccines in humans. For rAAV production in mammalian cells, a helper virus (e.g., adenovirus, vaccinia, or herpesvirus) is needed. Over the years, several modifications have been made to facilitate the production of rAAV, including (1) identifying and cloning the minimal set of helper proteins (adenovirus E1, E2A, E4, and VA), (2) providing the AAV Rep (Rep78, Rep68, Rep52, and Rep40) and capsid proteins in trans, and (3) developing a transgene system that allows packaging of DNA sequences flanked by the AAV Inverted Terminal Repeats (ITRs) (Samulski et al., *J Virol.* (1989) 63(9):3822-8). When these three components are introduced into mammalian cells, rAAV containing a transgene of interest can be readily purified. Recombinant AAV so produced has been used in clinical trials (Clement and Grieger, *Mol Ther Methods Cin Dev.* (2016) 3:16002).

The need for scaled-up rAAV production for larger clinical trials and commercialization has led to the development of insect cell-based production systems that utilize baculoviral vectors to express the Rep and capsid proteins and to carry the coding sequence for a transgene-containing AAV vector genome, which is packaged into rAAV capsids. Insect cell-based manufacturing of recombinant AAV (rAAV) offers several advantages over mammalian cell-based rAAV manufacturing, including scalability of non-adherent cells and cost savings due to the use of serum-free growth conditions. Such systems also do not require adenovirus helper functions (see, e.g., Urabe et al., *Hum Gene Ther.* (2002) 13:1935-43; Urabe et al., *J Vir.* (2006) 80(4):1874-85; Chen et al., *Mol Ther.* (2008) 16(5):924-30; Smith et al., *Mol Ther.* (2009) 17(11):1888-96; and Mietzsch et al., *Hum Gene Ther Methods* (2017) 28(1):15-22). While the baculovirus-insect cell system has been successfully utilized for rAAV production at multiple scales, it has been observed that rAAV generated in insect cells has reduced VP1 content (e.g., with a VP1:VP2:VP3 ratio of approximately 1:1:30 to 1:1:60) and consequently reduced potency, as compared to rAAV produced in mammalian cells (see, e.g., Urabe et al., 2002, supra; Kohlbrenner et al., *Mol Ther.* (2005) 12(6):1217-25; Urabe et al., 2006, supra; Aslanidi et al., *Proc Natl Acad Sci USA* (2009) 106(13):5059-64; Kondratov et al., *Mol Ther.* (2017) 25(12):2661-75; and Mietzsch et al., supra). Several efforts have been made to improve the capsid ratios by modifying the start codon context of VP1 (see, e.g., Kondratov et al., supra; Mietzsch et al., supra).

Thus, there remains a need for an improved baculovirus-insect cell system for producing rAAV at industrial scales.

SUMMARY OF THE INVENTION

The present disclosure provides baculovirus-insect cell systems for producing potent recombinant AAV at high yield. In one aspect, the present disclosure provides an insect cell (e.g., an Sf9 or Sf21 cell) comprising a first baculoviral vector comprising an expression cassette for Rep78 and a second baculoviral vector comprising an expression cassette for Rep52, wherein the first vector and the second vector further comprise (i) an expression cassette for VP1 and an expression cassette for VP2/VP3, respectively; or (ii) an expression cassette for VP2/VP3 and an expression cassette for VP1, respectively. In some embodiments, one or both of the first and second vectors are stably integrated into the genome of the insect cell.

In some embodiments, the Rep78 expression cassette and the Rep52 expression cassette comprise identical insect promoters. In some embodiments, the Rep78 expression cassette comprises a non-canonical start codon for the Rep78 coding sequence, wherein the codon is optionally ACG, TTG, GTG, or CTG.

In some embodiments, the VP1 expression cassette and the VP2/VP3 expression cassette comprise identical insect promoters. In some embodiments, the VP1, VP2, and VP3 proteins comprise amino acid sequences from the same AAV serotype, or from more than one AAV serotype. In certain embodiments, the VP1, VP2, and/or VP3 proteins comprise amino acid sequences from AAV1, AAV2, AAV3 (e.g., AAV3B), AAV6, and/or AAV9. In certain embodiments, the Rep78 and Rep52 proteins are derived from a different AAV serotype from the VP1, VP2, and/or VP3 proteins.

In some embodiments, the Rep78, Rep52, VP1, and VP2/VP3 expression cassettes each comprise an insect promoter selected from a polyhedron promoter, an IE-1 promoter, and a p10 promoter.

The insect cell herein may further comprise a coding sequence for a recombinant AAV genome, wherein the recombinant AAV genome comprises an expression cassette for a transgene of interest that is under the transcriptional control of a mammalian promoter, and an AAV inverted terminal repeat (ITR) on both termini. In some embodiments, the coding sequence for the recombinant AAV genome is located on the first or second vector, or is located on a third vector. The transgene of interest may encode, for example, a therapeutic protein, including, without limitation: a protein whose function is lacking or deficient in a genetic disease (e.g., a lysosomal storage disease, or a hemophilia), such as an enzyme (for use in an enzyme replacement therapy) and a blood clotting factor (for use as replacement factor); and a protein for regulating gene expression (e.g., a zinc finger protein (ZFP) transcription factor). The transgene of interest may also encode a gene editing protein, such as a zinc finger nuclease (ZFN), a ZFP deaminase, a ZFP recombinase, a TALEN, a CRISPR Cas protein, and a CRISPR Cpf protein. The transgene may also encode an interfering RNA molecule such as a small hairpin RNA.

In some embodiments, the VP1 protein and/or the VP2 protein comprise two or more mutations at residues 157, 162, 164, 179, 188, 194, 196, 197, 200, and 201 (numbering according to SEQ ID NO:1) relative to wildtype VP1 and VP2 proteins, respectively. As used herein, "numbering according to SEQ ID NO:1" means amino acid residue positions in SEQ ID NO:1, or the corresponding amino acid residue positions in a different VP1 sequence (e.g., VP1 sequence from a serotype other than AAV6). In some embodiments, the VP1 protein and/or the VP2 protein comprise two or more mutations selected from the group consisting of S157A, T162S, Q164A, S179T, L188I, T194A, A196S, A197G, P200S, and T201L (numbering according to SEQ ID NO:1). In further embodiments, the VP1 protein and/or the VP2 protein comprise all of these ten mutations.

In some embodiments, the VP1 protein further comprises one or more mutations at residues 67, 81, 84, 85, and 92 relative to wildtype VP1 protein (numbering according to SEQ ID NO:1). In certain embodiments, the VP1 protein comprises one or more mutations selected from the group consisting of A67E, Q81R, K84D, A85S, and R92K. In further embodiments, the VP1 protein comprises all of these five mutations.

In some embodiments, the VP1 protein and the VP2 protein disclosed herein are identical to the VP1 protein and the VP2 protein, respectively, of AAV6 but for the mutations. In particular embodiments, the VP1 protein and/or the VP2 protein are derived from AAV6 and comprise mutations S157A, T162S, Q164A, S179T, L188I, T194A, A196S, A197G, P200S, and T201L relative to wildtype AAV6 VP1 and VP2 proteins, respectively.

In some embodiments, the VP1-expressing vector also comprises an expression cassette for assembly-activating protein (AAP), wherein the AAP comprises one or more mutations at residues 8, 10, 12, 17, 21, and 22 (numbering according to SEQ ID NO:10) relative to wildtype AAP protein. As used herein, "numbering according to SEQ ID NO:10" means amino acid residue positions in SEQ ID NO:10, or the corresponding amino acid residue positions in a different AAP sequence (e.g., AAP sequence from a serotype other than AAV6). In certain embodiments, the AAP comprises one or more (e.g., all) mutations selected from the group consisting of P8Q, H10L, L12Q, Q17P, L21Q, and L22V. In particular embodiments, the AAP is identical to wildtype AAP of AAV6 but for the AAP mutations.

In particular embodiments, the VP1 expression cassette comprises a coding sequence for SEQ ID NO:7, with or without the first amino acid (e.g., nucleotides 18-151 of SEQ ID NO:14). In further embodiments, the capsid expression cassettes comprise 10 or more (e.g., 20 or more, 30 or more, 40 or more, 50 or more, 75 or more, 100 or more, 125 or more, or 150 or more) contiguous nucleotides, or the entire nucleotide sequence, of SEQ ID NO:14.

In some embodiments, the VP1 protein comprises one or more mutations at residues 81, 84, 85, and 92 relative to wildtype VP1 protein (numbering according to SEQ ID NO:1). In some embodiments, the VP1 protein comprises one or more mutations selected from the group consisting of Q81R, K84D, A85S, and R92K. In further embodiments, the VP1 protein comprises all of these four mutations. In particular embodiments, the VP1 protein further comprises a mutation at residue 67, e.g., an A67E mutation. In some embodiments, the VP1 protein is identical to the VP1 protein of AAV6 but for the mutation(s). In certain embodiments, the VP1 protein comprises mutations A67E, Q81R, K84D, A85S, and R92K relative to wildtype AAV6 VP1.

In particular embodiments of the present insect cell AAV production systems, the VP1 comprises SEQ ID NO:1, 7, or 16 with or without the first amino acid residue; the VP2 comprises amino acid residues 138-736 or 139-736 of SEQ ID NO:1 or 7, or comprises SEQ ID NO:18 with or without the first amino acid residue; the VP3 comprises amino acid residues of 204-736 or 205-736 of SEQ ID NO:1 or amino acid residues 203-736 or 204-736 of SEQ ID NO:7, or comprises SEQ ID NO:19 with or without the first amino acid residue.

In some embodiments, the VP1 comprises SEQ ID NO:24 with or without the first amino acid residue; the VP2 comprises amino acid residues 138-736 or 139-736 of SEQ ID NO:24; and the VP3 comprises amino acid residues of 203-736 or 204-736 of SEQ ID NO:24.

In some embodiments, the VP1 comprises SEQ ID NO:25 with or without the first amino acid residue; the VP2 comprises amino acid residues 138-735 or 139-735 of SEQ ID NO:25; and the VP3 comprises 203-735 or 204-735 of SEQ ID NO:25.

In some embodiments, the VP1 comprises SEQ ID NO:26 with or without the first amino acid residue; the VP2 comprises amino acid residues 138-736 or 139-736 of SEQ ID NO:26; and the VP3 comprises amino acid residues of 203-736 or 204-736 of SEQ ID NO:26.

In some embodiments, the VP1 comprises SEQ ID NO:27 with or without the first amino acid residue; the VP2 comprises amino acid residues 138-736 or 139-736 of SEQ ID NO:27; and the VP3 comprises amino acid residues of 203-736 or 204-736 of SEQ ID NO:27.

In some embodiments, the Rep78 comprises SEQ ID NO:21 with or without the first amino acid residue; and/or the Rep52 comprises SEQ ID NO:23 with or without the first amino acid residue.

These embodiments encompass helper proteins (Rep78, Rep52, VP1, VP2, and VP3) that do not contain the first amino acid residue encoded by the coding sequence (i.e., the amino acid encoded by the start codon) because the producing cell cleaves off that first amino acid residue. These embodiments also encompass helper proteins whose first amino acid residues are encoded by a non-canonical start codon such as those described herein or otherwise known in the art.

In another aspect, the present disclosure also provides a recombinant AAV virion produced in the insect cell herein, its use in treating a human patient in need of the transgene, its use in the manufacture of a medicament for such treatment, and a pharmaceutical composition comprising the recombinant AAV virion and pharmaceutically acceptable carrier.

In another aspect, the present disclosure provides a method of producing a recombinant AAV virion, comprising providing an insect cell herein, culturing the insect cell under conditions that allow expression of the recombinant AAV genome and packaging of the recombinant AAV genome within an AAV capsid comprising the VP1, VP2, and VP3 proteins, and isolating the recombinant AAV from the culture. Also provided are a combination (e.g., a composition) of the expression cassettes for making the AAV virion in insect cells.

Other features, objectives, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

BRIEF DESCRIPTION OF THE FIGURES

FIG. 1A discloses SEQ ID NOs:28-33, respectively, in order of appearance, wherein SEQ ID NO: 28 represents a consensus sequence used for alignment numbering, and SEQ ID NO: 29 corresponds to AAV3B, SEQ ID NO: 30 corresponds to AAV5, SEQ ID NO: 31 corresponds to AAV6, SEQ ID NO: 32 corresponds to AAV8, and SEQ ID NO: 33 corresponds to AAV9.

FIG. 1B discloses SEQ ID NOs:34-38, 73, and 39-43, respectively, in order of appearance, wherein SEQ ID NO: 34 represents a consensus sequence used for alignment numbering, SEQ ID NO: 35 corresponds to AAV1, SEQ ID NO: 36 corresponds to AAV2, SEQ ID NO: 37 corresponds to AAV3B, SEQ ID NO: 38 corresponds to AAV4, SEQ ID NO: 73 corresponds to AAV6, SEQ ID NO: 39 corresponds to AAV7, SEQ ID NO: 40 corresponds to AAV8, SEQ ID NO: 41 corresponds to AAV9, SEQ ID NO: 42 corresponds to AAV10, and SEQ ID NO: 43 corresponds to AAV11.

FIG. 1C is a table comparing corresponding amino acid positions from AAV serotypes 1, 4, 6, 7, 8, and 11 between amino acid residues 158-203 as aligned in FIG. 1B. The table indicates amino acid mutations that may prevent proteolytic cleavage in these serotypes. Amino acid residue numbers are based on the consensus sequence shown in FIG. 1B (SEQ ID NO: 34). The amino acid sequences corresponding to AAV1 (SEQ ID NO: 35), AAV4 (SEQ ID NO: 38), AAV6 (SEQ ID NO: 73), AAV7 (SEQ ID NO: 39), AAV8 (SEQ ID NO: 40), and AAV11 (SEQ ID NO: 43) are referenced in FIG. 1C.

FIG. 2 discloses SEQ ID NOs:44-45, respectively, in order of appearance.

FIG. 3A: a sequence alignment of Variants 1, 2, 3, and 4 of AAV6/9 VP1/VP2 (numbering according to SEQ ID NO:1). FIG. 3B: partial alignment of the cap/AAP nucleotide sequences and the AAP amino acid sequences (in rectangle) of AAV6, AAV9 Transplant, Variant 1, Variant 2, Variant 3, and Variant 4. The AAP amino acid sequence of AAV9 Transplant has six mutations (P8Q, H10L, L12Q, Q17P, L21Q, and L22V) relative to that of AAP6 in the indicated region, while the AAP amino acid sequences of Variants 1-3 each have only two mutations (L21Q and L22V). Variant 4 has the native AAP6 sequence in the indicated region. FIG. 3A discloses SEQ ID NOs:46-51 wherein AAV6 corresponds to SEQ ID NO: 46, AAV9 Transplant corresponds to SEQ ID NO: 47, Variant 1 corresponds to SEQ ID NO: 48, Variant 2 corresponds to SEQ ID NO: 49, Variant 3 corresponds to SEQ ID NO: 50, and Variant 4 corresponds to SEQ ID NO: 51 and FIG. 3B discloses SEQ ID NOs:52, 67, 53, 68, 54, 69, 55, 70, 56, 71, 57, and 72 wherein AAV6 corresponds to SEQ ID NOs: 52 and 67, AAV9 Transplant corresponds to SEQ ID NOs: 53 and 68, Variant 1 corresponds to SEQ ID NOs: 54 and 69, Variant 2 corresponds to SEQ ID NOs: 55 and 70, Variant 3 corresponds to SEQ ID NOs: 56 and 71, and Variant 4 corresponds to SEQ ID NOs: 57 and 72.

FIG. 4A discloses SEQ ID NOs:58-62, 8, 63-64, 9, and 65-66, respectively, in order of appearance, wherein SEQ ID NO: 58 represents the consensus sequence used for residue numbering, and wherein AAV1 corresponds to SEQ ID NO: 59, AAV2 corresponds to SEQ ID NO: 60, AAV3B corresponds to SEQ ID NO: 61, AAV4 corresponds to SEQ ID NO: 62, AAV6 corresponds to SEQ ID NO: 8, AAV7 corresponds to SEQ ID NO: 63, AAV8 corresponds to SEQ ID NO: 64, AAV9 corresponds to SEQ ID NO: 9, AAV10 corresponds to SEQ ID NO: 65, and AAV11 corresponds to SEQ ID NO: 66.

FIG. 4B shows the amino acid differences in the indicated AAP region (consensus numbering) between (i) AAV1 (SEQ ID NO: 59), AAV2 (SEQ ID NO: 60), AAV4 (SEQ ID NO: 62), AAV6 (SEQ ID NO: 8), AAV7 (SEQ ID NO: 63), AAV8 (SEQ ID NO: 64), AAV10 (SEQ ID NO: 65), or AAV11 (SEQ ID NO: 66) and (ii) AAV9 (SEQ ID NO: 9) or AAV3B (SEQ ID NO: 61). Amino acid residue numbers are based on the consensus sequence shown in FIG. 4A.

DETAILED DESCRIPTION OF THE INVENTION

Figure 1A:
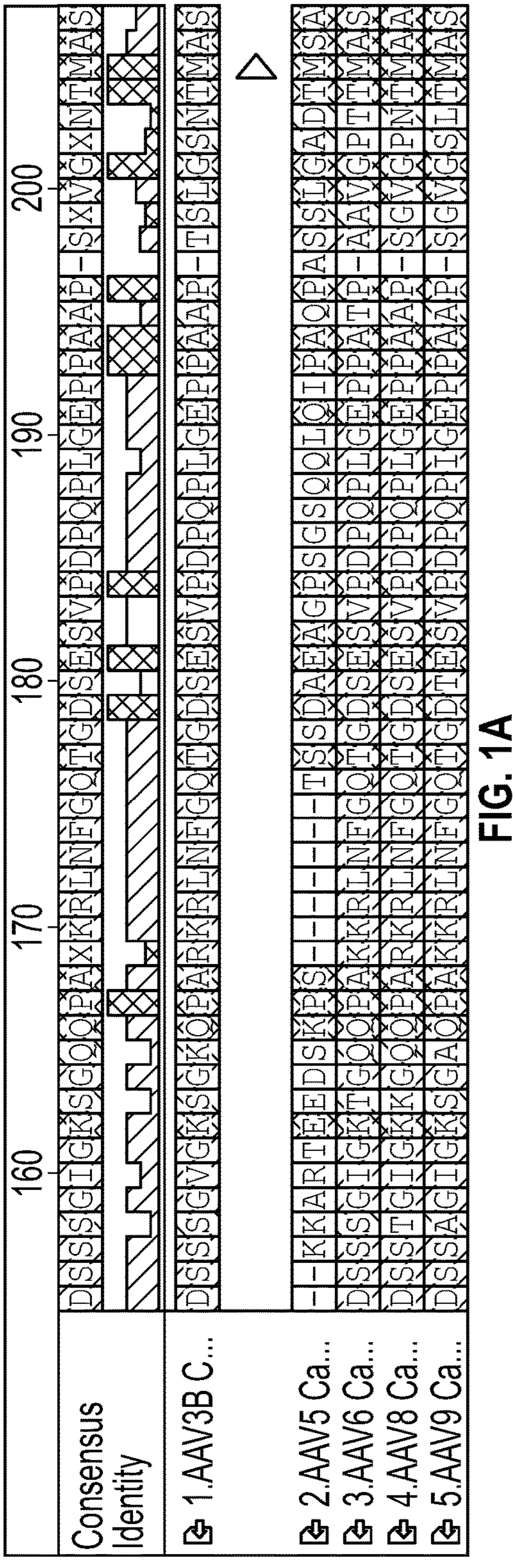
FIG. 1A shows the alignment of the VP1/VP2 amino acid sequences from AAV serotypes 3B, 5, 6, 8, and 9 between amino acid residues 155 and 207 (numbering based on consensus sequence). N-terminal Edman degradation sequencing was performed on the proteolytic cleavage products cored from an SDS-PAGE gel to identify the proteolytic cleavage site in AAV6 VP1/VP2. The cleavage site maps to residues $G_{190}E_{191}$. Multiple sequence alignment was generated using the Geneious software package and default settings for ClustalW alignment. The VP3 start site is indicated by the triangle at residue 205.
Figure 1B:
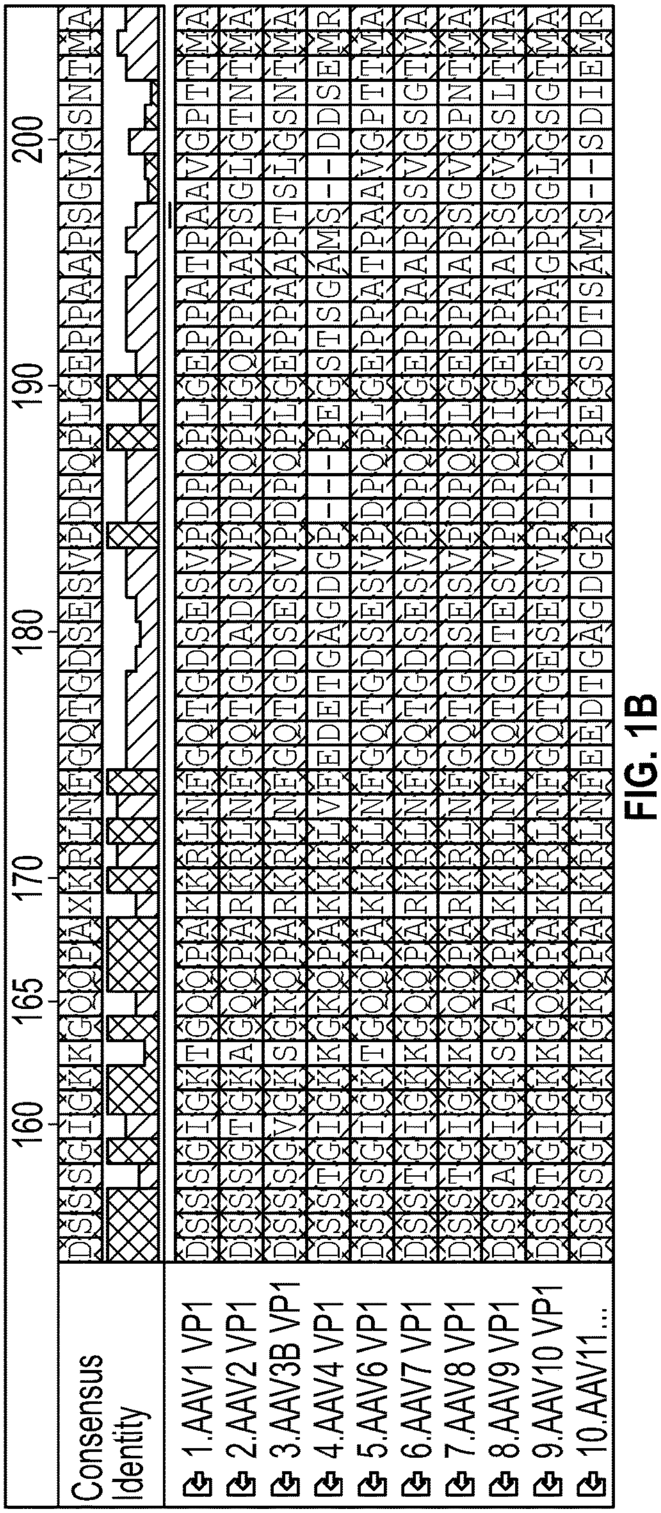
FIG. 1B shows the alignment of the VP1/VP2 amino acid sequences from AAV serotypes 1, 2, 3B, 4, and 6-11 between amino acid residues 155 and 205 (numbering based on consensus sequence). Multiple sequence alignment was generated using the Geneious software package and default settings for ClustalW alignment.

The present disclosure provides improved baculovirus-insect cell systems and related compositions for producing potent rAAV capsids at high yield. The present rAAV production systems utilize dual baculoviral helper vectors. The first vector carries an expression cassette for Rep78 and an expression cassette for VP1 or VP2/VP3, while the second vector carries an expression cassette for Rep52 and an expression cassette for the remaining capsid protein(s) (VP2/VP3 if the first vector expresses VP1, or VP1 if the first vector expresses VP2/VP3). In some embodiments, the Rep78 cassette uses a promoter identical (or having similar strength) to the promoter in the Rep52 cassette, and optionally has a suboptimal start codon, such that the Rep78 and Rep52 proteins can be produced with an optimal stoichiometry. In other embodiments, the Rep78 cassette uses a promoter weaker than the promoter in the Rep52 cassette, but has a canonical start codon, such that the Rep78 and Rep52 proteins can be produced with an optimal stoichiometry.

In some embodiments, the VP1 cassette uses a promoter identical (or having similar strength) to the promoter in the VP2/VP3 cassette, and optionally has a suboptimal start codon, such that the three capsid proteins can be produced with an optimal stoichiometry. In other embodiments, the VP1 cassette uses a promoter weaker than the promoter in the VP2/VP3 cassette, but has a canonical start codon, such that the capsid proteins can be produced with an optimal stoichiometry.

To reduce the number of baculoviral vectors needed to transduce the rAAV-producing cells, the coding sequence for the rAAV genome may also be included in one of the two vectors, for example, in the second vector (i.e., the vector that carries the Rep52 expression cassette).

The present inventors have discovered that expressing Rep78 and Rep52 from separate cassettes and expressing VP1 and VP2/VP3 from separate cassettes greatly improve the potency and/or yield of the rAAV produced in the insect cell systems. As demonstrated in the Working Example below, the present systems produce rAAV with a multi-fold increase in potency and/or yield as compared to production systems in which the capsid proteins are produced from the prevailing one-vector system, in which the capsid proteins are produced from a single Cap gene and the Rep proteins are produced from a single Rep gene.

The present production systems can be used to produce rAAV of any serotype, such as AAV1, AAV2, AAV3, AAV3A, AAV3B, AAV4, AAV5, AAV6, AAV7, AAV8, AAV8.2, AAV9, AAVrh10, or an engineered serotype. The coding sequences of the capsid proteins may be derived from any desired serotype.

The present systems also can be used to produce rAAV of a pseudotype such as AAV2/8, AAV2/5, or AAV2/6. By "pseudotype," "pseudotyped," or "cross-packaged" rAAV is meant a recombinant AAV whose capsid is replaced with the capsid of another AAV serotype, to, for example, alter transduction efficacy or tropism profiles of the virus (see, e.g., Balaji et al., *J Surg Res.* (2013) 184(1):691-8). For example, an AAV2/8 pseudotyped AAV contains capsids of AAV8 and the ITRs derived from AAV2.

The present systems also may be used to produce a chimeric or hybrid AAV. By "chimeric" or "hybrid" rAAV is meant a recombinant AAV whose capsid is assembled from capsid proteins derived from different serotypes and/or whose capsid proteins are chimeric proteins with sequences derived from different serotypes (e.g., serotypes 1 and 2; see, e.g., Hauck et al., *Mol Ther.* (2003) 7(3):419-25).

I. Capsid Protein Expression Cassettes

In mammalian cells, the Cap gene is transcribed into two mRNAs under the control of the mammalian p40 promoter. One mRNA is translated to VP1, and the other into VP2 and VP3. The translation start codon for VP2 is ACG, a suboptimal start codon that often causes ribosome skip, whereas the start codon for VP3 is the canonical ATG. Through an interplay of alternative splicing and the weak VP2 start codon, the Cap gene produces VP1, VP2, and VP3 in an apparent protein ratio of 1:1:10 (see, e.g., Berns and Parrish, supra).

Failures of prior insect cell systems to produce rAAV with high yield and potency have been attributed in part to the inability of these systems to achieve an optimal stoichiometry of the capsid proteins. In the present rAAV production systems, two separate expression cassettes are used for expressing VP1 and VP2/VP3. The use of separate expression cassettes for VP1 and VP2/VP3 surprisingly leads to high yield production of potent rAAV.

In some embodiments, the expression cassette for VP1 and the expression cassette for VP2/VP3 use insect promoters of the same or similar strengths. For example, the two cassettes may use identical promoters. Examples of insect promoters that can be used are a p10 promoter, a p35 promoter, a polyhedron (polyh) promoter, an E1 promoter, a ΔE1 promoter, a 4×Hsp27 EcRE+minimal Hsp70 promoter, and a basic promoter.

The expression cassettes may contain additional regulatory elements, such as Kozak sequences; transcription initiation and termination sites (either modified or unmodified); mRNA splice sites (either modified or unmodified, within or adjacent to the polypeptide coding sequence; and viral, eukaryotic, or prokaryotic RNA elements that control splicing, nuclear export, localization, stabilization, or translation of mRNAs (e.g., Woodchuck hepatitis virus posttranscriptional regulatory element (WPRE) (Zufferey et al., *J Virol.* (1999) 73(4):2886-92), MMLV/MPMV, eukaryotic constitutive transport element (CTE) (Li et al., *Nature* (2006) 443(7108):234-7), RNA zipcodes (Jambhekar and DeRisi, *RNA* (2007) 13(5):625-42), and omega or other 5'-UTR RNA elements that increase translational efficiency).

In some embodiments, the coding sequences for the capsid proteins may be modified to further enhance AAV yield and potency. For example, the coding sequences may be codon-modified to increase mRNA stability, translation efficiency, and/or DNA vector stability in insect cells. The start codon regions of the coding sequences may also be modified, to further fine tune expression levels of the capsid proteins; for example, the VP1 start codon may be changed from wildtype ATG to a suboptimal codon, such as the start codon of VP2 (ACG), such that VP1 expression levels are lower. The VP1 start codon may also be changed to other suboptimal start codons such as TTG, CTG, and GTG.

To avoid production of VP2 and VP3 or any other by-product peptide from the VP1 expression cassettes, the VP1 coding sequence may be mutated to remove the native start codons for the embedded VP2 and VP3 ORFs, any out-of-frame ATG sites, any undesired splice acceptor sites, any cryptic promoter sequences, and/or any destabilizing elements (see, e.g., Smith et al., supra).

In some embodiments, the present production systems produce rAAV6. The complete amino acid sequence of an AAV6 VP1 protein is shown below, where the start site of VP2 (T) and the mutated start site of VP3 (changed from the native M) are boldfaced and underlined:

(SEQ ID NO: 1)

```
1    XAADGYLPDW LEDNLSEGIR EWWDLKPGAP KPKANQQKQD DGRGLVLPGY KYLGPFNGLD
61   KGEPVNAADA AALEHDKAYD QQLKAGDNPY LRYNHADAEF QERLQEDTSF GGNLGRAVFQ
121  AKKRVLEPFG LVEEGAKTAP GKKRPVEQSP QEPDSSSGIG KTGQQPAKKR LNFGQTGDSE
181  SVPDPQPLGE PPATPAAVGP TTVVASGGGAE MADNNEGADG VGNASGNWHC DSTWLGDRVI
241  TTSTRTWALP TYNNHLYKQI SSASTGASND NHYFGYSTPW GYFDFNRFHC HFSPRDWQRL
301  INNNWGFRPK RLNFKLFNIQ VKEVTTNDGV TTIANNLTST VQVFSDSEYQ LPYVLGSAHQ
361  GCLPPFPADV FMIPQYGYLT LNNGSQAVGR SSFYCLEYFP SQMLRTGNNF TFSYTFEDVP
421  FHSSYAHSQS LDRLMNPLID QYLYYLNRTQ NQSGSAQNKD LLFSRGSPAG MSVQPKNWLP
481  GPCYRQQRVS KTKTDNNNSN FTWTGASKYN LNGRESIINP GTAMASHKDD KDKFFPMSGV
541  MIFGKESAGA SNTALDNVMI TDEEEIKATN PVATERFGTV AVNLQSSSTD PATGDVHVMG
601  ALPGMVWQDR DVYLQGPIWA KIPHTDGHFH PSPLMGGFGL KHPPPQILIK NTPVPANPPA
661  EFSATKFASF ITQYSTGQVS VEIEWELQKE NSKRWNPEVQ YTSNYAKSAN VDFTVDNNGL
721  YTEPRPIGTR YLTRPL
```

In the sequence above, X in position 1 may be M (wildtype; source: GenBank AAB95450.1), T, L, or V. In other embodiments, the VP1 start residue may be another amino acid encoded by a non-canonical start codon such as a suboptimal start codon (see, e.g., Kearse et al., *Genes Dev.* (2017) 31:1717-31). In some embodiments, the mutated VP3 start site in the VP1 protein is an amino acid other than the V shown above. In some embodiments, the AAV6 VP2 protein produced herein comprises a sequence spanning amino acids 138 to 736 of SEQ ID NO:1 where the VP3 start site is not mutated (i.e., is the native methionine) and the AAV6 VP3 protein comprises a sequence spanning amino acids 204-736 of SEQ ID NO:1 where the N-terminal amino acid is the native M.

Additional, non-limiting examples of coding sequence modifications are described below. See also WO 2020/168145, the disclosure of which is incorporated hereby by reference in its entirety.

A. Modifications to Reduce Proteolytic Degradation of VP1 and VP2

In some embodiments, the VP1 and VP2 coding sequences may be mutated in two or more codons such that the VP1 and VP2 proteins encoded thereby are resistant to proteolytic degradation during the production process. Because the VP1 coding sequence also contains the open reading frame for AAP, the codon changes may also cause mutations in the AAP. These mutations in VP1 and VP2 further improve the rAAV's infectivity, i.e., potency.

In some embodiments, the present improved baculovirus-insect cell systems can be used to produce any AAV serotype that is susceptible to proteolysis in insect cells. Such AAV serotypes may include, for example, AAV1, AAV6, AAV8, or variants thereof, or any pseudotyped or chimeric rAAV whose VP1 and VP2 proteins are susceptible to proteolysis in insect cells.

In an improved AAV production system of the present disclosure, two or more point mutations are introduced to AAV VP1 and VP2 proteins derived from, e.g., AAV1, AAV4, AAV6, AAV7, AAV8, or AAV11, to remove the sites susceptible to proteolysis in insect cells. The introduced point mutations may be residues identical to those at the corresponding positions in AAV2, AAV3, AAV5, AAV9, or AAV10.

By "corresponding" amino acid residue or region is meant an amino acid residue or region that aligns with (though not necessarily identical to) the reference residue or region, when the subject sequence and the reference sequence containing the residues or regions are aligned to achieve maximum homology (allowing gaps that are recognized in the art). For example, amino acid residue 189 (L) of AAV8 VP1 corresponds to amino acid residue 188 of AAV6 VP1.

In these systems, the overlapping region shared by the VP1 and VP2 proteins may be mutated to remove proteolytic sites. For example, the rAAV6 VP1 and/or VP2 may comprise mutations relative to the wildtype at two or more residues in a region corresponding to residues 138-203 (e.g., residues 151-201, residues 157-201, or residues 185-194 (i.e., PQPLGEPPAT (SEQ ID NO:2), where cleavage has been shown between G and E)) of SEQ ID NO:1, where the mutated residues are selected from a group consisting of residues 157, 162, 164, 179, 188, 194, 196, 197, 200, and 201. In some embodiments, the AAV6 VP1 and/or VP2 comprise two or more mutations selected from the group consisting of S157A, T162S, Q164A, S179T, L188I, T194A, A196S, A197G, P200S, and T201L (numbering according to SEQ ID NO:1). For example, an AAV6 VP1 and/or VP2 may have the mutations (i) S179T, L188I, T194A, A196S, A197G, P200S, and T201L ("Variant 1"); (ii) S179T, L188I, T194A, A196S, and A197G ("Variant 2"); (iii) T194A, A196S, A197G, P200S, and T201L ("Variant 3"); (iv) S157A, T162S, and Q164A ("Variant 4"); or (v) P200S and T201L. For convenience, only the residue numbers in VP1 are referred to herein. The numbers of the corresponding residues in VP2 can be readily discerned from SEQ ID NO:1 above. For example, residue S157 in VP1 is residue S20 in VP2.

In particular embodiments, the AAV6 VP1 and/or VP2 comprise the mutation L188I and one or more other mutations in the group. For example, the AAV6 VP1 and/or VP2 may have the mutations L188I, P200S, and T201L.

In some embodiments, the AAV6 VP1 and/or VP2 comprise all ten mutations of S157A, T162S, Q164A, S179T, L188I, T194A, A196S, A197G, P200S, and T201L, such that their sequence in the region corresponding to residues 157-201 in SEQ ID NO:1 is as follows. AGIGKSGAQP AKKRLNFGQT GDTESVPDPQ PIGEPPAAPS GVGSL (SEQ ID NO:4) This sequence is identical to the sequence in the corresponding region in AAV9 VP1 and VP2.

Figure 2:
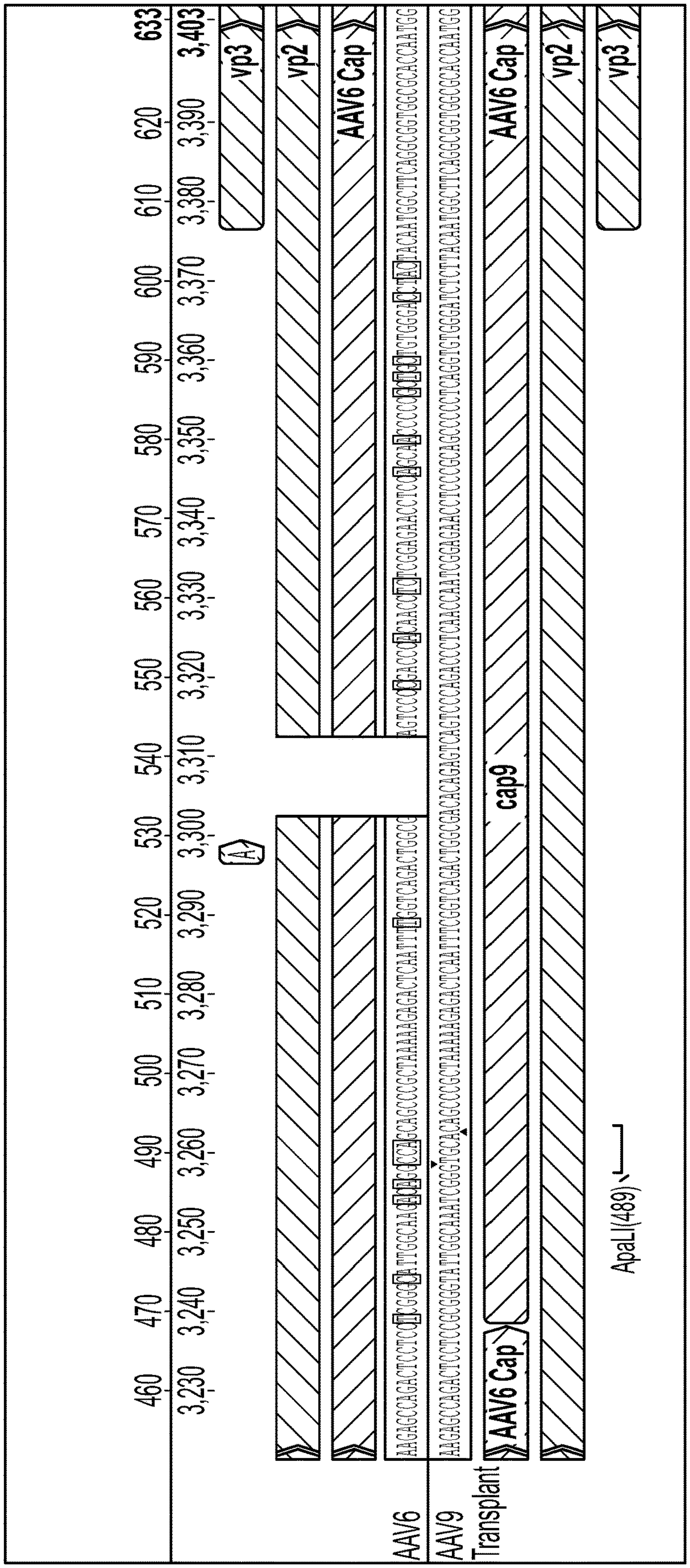
FIG. 2 shows the substitution of a 45-amino acid stretch of an AAV9 VP1/VP2 (SEQ ID NO:4) for the corresponding region in the AAV6 VP1/VP2 sequence (SEQ ID NO:3), which abolishes proteolytic cleavage of the resultant chimeric VP1/VP2 proteins ("AAV6/9 VP1/VP2"). The figure shows the alignment of the transplanted AAV9 Cap nucleotide sequence (SEQ ID NO:45) and the AAV6 Cap nucleotide sequence (SEQ ID NO:44) that is replaced in AAV9 Transplant; the arrow "A" indicates the AAP start codon. AAV9 Transplant: baculoviral helper vector whose AAV6 Cap gene contains a sequence from the AAV9 Cap gene.
Figure 3A:
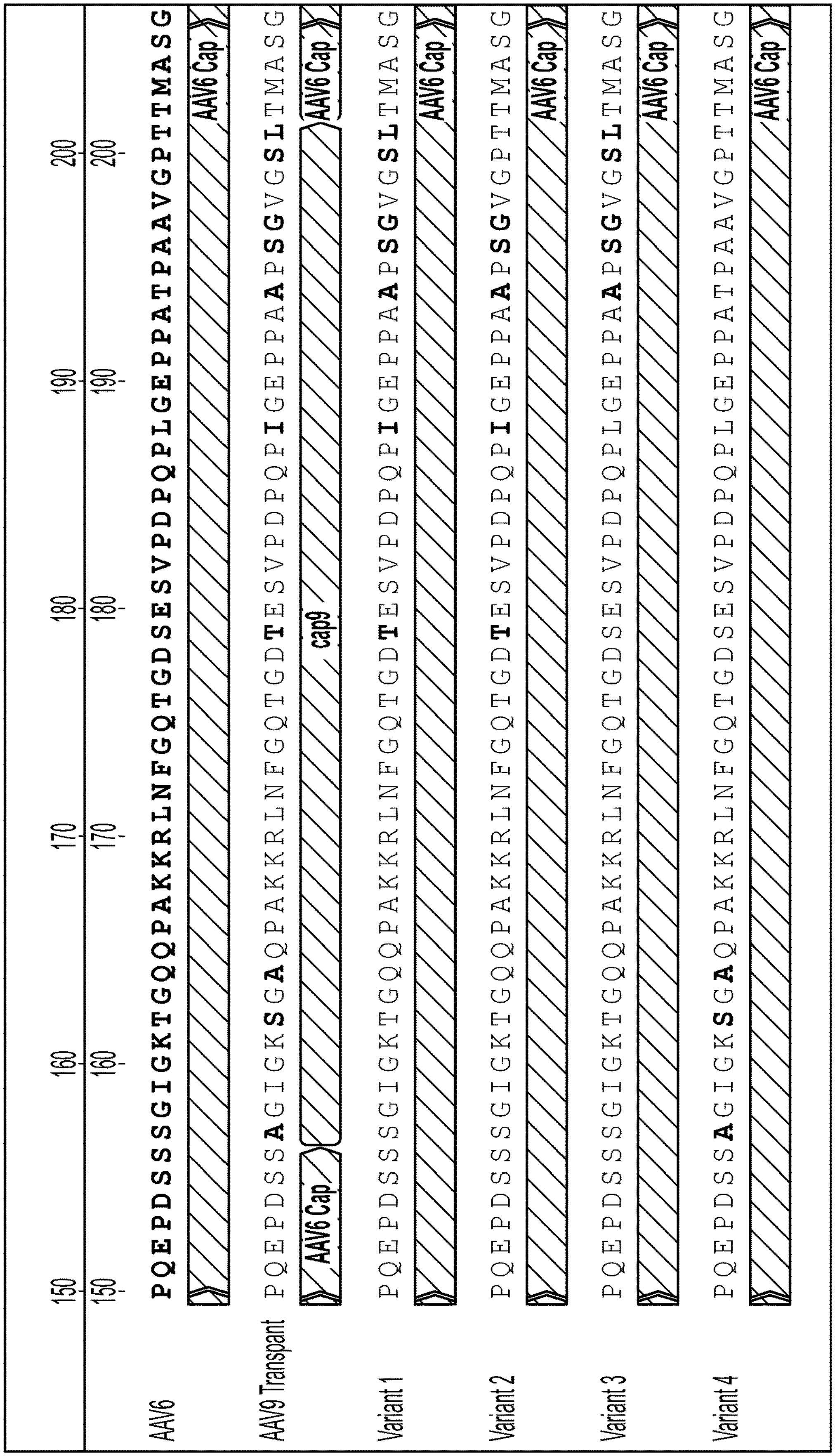
FIGS. 3A and 3B illustrate variants of AAV6/9 VP1/VP2 prevented cleavage.
Figure 3B:
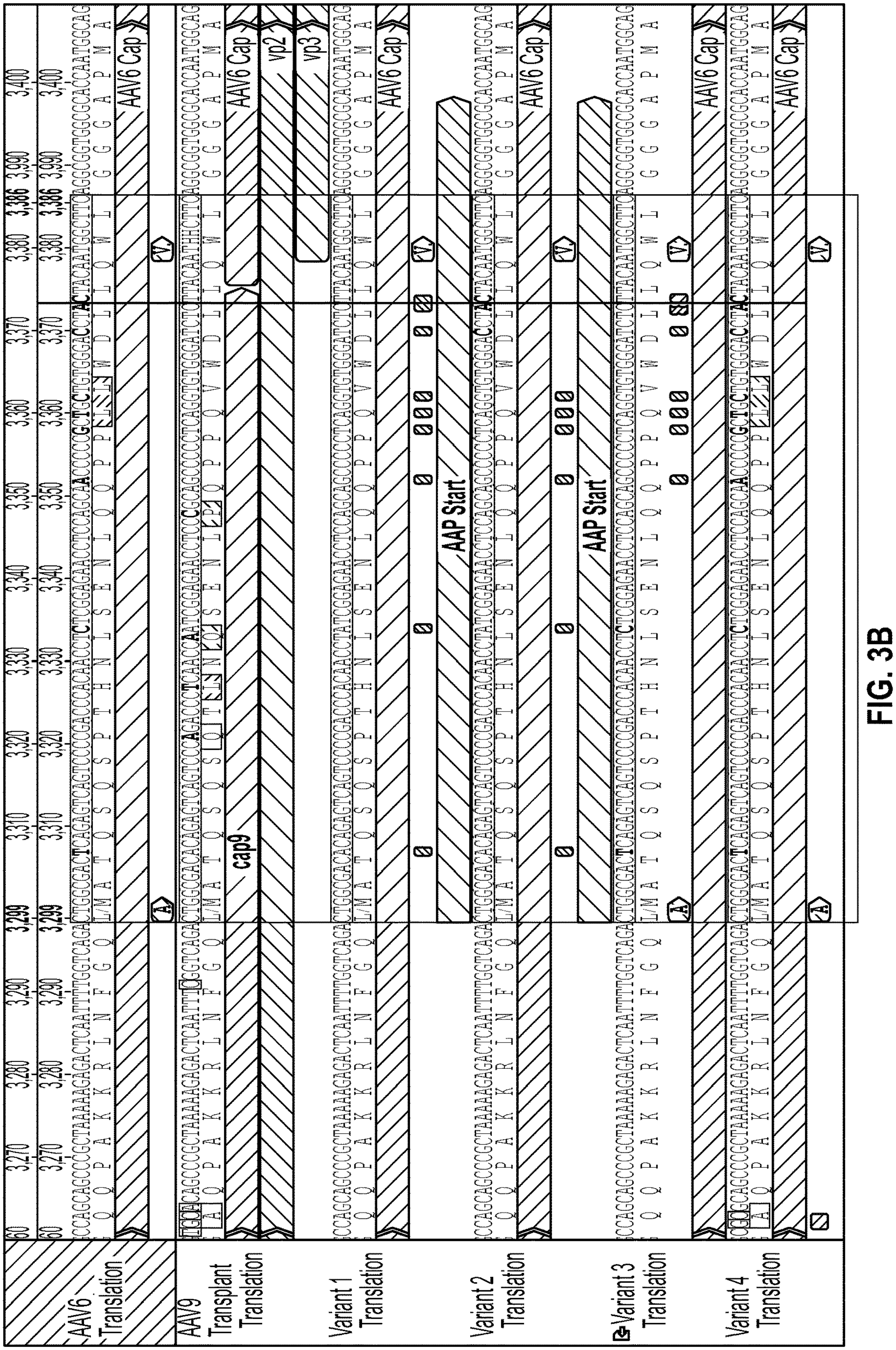

Thus, to generate a modified VP1 coding sequence, one can replace the coding sequence for residues 157-201 of VP1 (i.e., residues 20-64 of VP2; SEQ ID NO:3) with the coding sequence for the corresponding amino acid sequence (SEQ ID NO:4) of AAV9, using well known molecular clone techniques; the resultant modified baculoviral AAV6 helper vector is referred to herein as "AAV9 Transplant" and the resultant VP1 proteins are referred to herein as "AAV6/9 VP1." The same transplant may be made to mutate the same region in VP2, resulting in an AAV6/9 VP2. In some embodiments, the portion of the AAV6 VP1 gene sequence that is replaced comprises the underlined sequence shown below (see also FIG. 2):

```
                                        (SEQ ID NO: 13)
AAGAGCCAGACTCCTCCTCGGGCATTGGCAAGACAGGCCAGCAGCCCGC

TAAAAAGAGACTCAATTTTGGTCAGACTGGCGACTCAGAGTCAGTCCCC

GACCCACAACCTCTCGGAGAACCTCCAGCAACCCCCGCTGCTGTGGGAC

CTACTACAATGGCTTCAGGCGGTGGCGCACCAATGG
```

In certain embodiments, the underlined portion in SEQ ID NO: 13 is replaced by a corresponding Cap gene sequence from AAV9 to generate an AAV9 Transplant disclosed herein. In particular embodiments, the AAV9 Cap sequence transplanted to the AAV6 Cap gene in an AAV9 Transplant comprises the underlined sequence shown below (see also FIG. 2):

```
                                        (SEQ ID NO: 14)
AAGAGCCAGACTCCTCCGCGGGTATTGGCAAATCGGGTGCACAGCCCGC

TAAAAAGAGACTCAATTTCGGTCAGACTGGCGACACAGAGTCAGTCCCA

GACCCTCAACCAATCGGAGAACCTCCCGCAGCCCCCTCAGGTGTGGGAT

CTCTTACAATGGCTTCAGGCGGTGGCGCACCAATGG
```

In other embodiments, a modified cap6 gene in the baculoviral AAV6 helper construct can be generated by replacing the coding sequence for residues 157-201 of VP1 in SEQ ID NO:1 (i.e., residues 20-64 of VP2; SEQ ID NO:3) with the coding sequence for the corresponding amino acid sequence from a serotype whose VP1 and/or VP2 are resistant to proteolytic cleavage in insect cells, e.g., AAV2, AAV3, AAV5, or AAV10.

In other embodiments, the VP1/VP2 proteins of AAV serotypes, such as AAV1, AAV4, AAV7, AAV8, or AAV11, can be mutated such that they contain one or more mutations shown in FIG. 1C. The resultant proteins are expected to be more resistant to proteolysis in insect cells. Unlimiting examples of engineered VP1/VP2 proteins from various AAV serotypes are shown below:

(1) the engineered AAV1 VP1/VP2 proteins may contain one or more of the following mutations: S158T/A, I160T/V, T163A/S/K, Q165K/A, K169R, S180A/T, L189E/I, T195A, A197S/T, A198S/G, V199L, P201T/S, and T202N/L;

(2) the engineered AAV4 VP1/VP2 proteins may contain one or more of the following mutations: T158S/A, I160T/V, K163A/S, K165Q/A, K169R, K171R, V173N, E175G, D176Q/E, E177T, T178G, G179D/E, A180S/T, G181D/E, D182S, G183V, E189L/I, S191Q/E, T192P, S193P, G194A, M196P, S197T, D200G, D201T/S, S202N/L, and E203T;

(3) the engineered AAV6 VP1/VP2 proteins may contain one or more of the following mutations: S158T/A, I160T/V, T163A/S/K, Q165K/A, K169R, S180A/T, L189E/I, T195A, A197S/T, A198S/G, V199L, P201T/S, and T202N/L;

(4) the engineered AAV7 VP1/VP2 proteins may contain one or more of the following mutations: T158S/A, I160T/V, K163A/S, Q165K/A, R169K, S180A/T, L189E/I, S197T, S198G, V199L, and G202N/L;

(5) the engineered AAV8 VP1/VP2 proteins may contain one or more of the following mutations: T158S/A, I160T/V, K163A/S, Q165K/A, R169K, S180A/T, L189E/I, S197T, G198S, V199L, P201T/S, and N202L; and (6) the engineered AAV11 VP1/VP2 proteins may contain one or more of the following mutations: S158T/A, I160T/V, K163A/S, K165Q/A, R169K, E175G, E176Q, D177T, T178G, G179D/E, A180S/T, G181D/E, D182S, G183V, E189L/I, S191Q/E, D192P, T193P, S194A, M196P, S197T, S200G, D201T/S, 1202N/L, and E203T (consensus numbering; see FIG. 1C).

In some embodiments, the VP1/VP2 proteins from an AAV serotype susceptible to proteolysis in insect cells are mutated to contain one or more mutations at the following amino acid residues (consensus numbering in FIG. 1C): 158, 163, 165, 180, 189, 195, 197, 198, 201, and 202. (These residues correspond respectively to amino acid residues 157, 162, 164, 179, 188, 194, 196, 197, 200, and 201 according to the numbering of SEQ ID NO:1 (AAV6) or a corresponding sequence from another serotype aligned to show maximal homology to SEQ ID NO:1.) In further embodiments, the VP1/VP2 proteins may additionally contain one or more mutations at the following amino acid residues (consensus numbering in FIG. 1C): 160, 169, 171-179, 181-183, 191-194, 196, 199, and 203.

In some embodiments, the VP1/VP2 proteins from an AAV serotype susceptible to proteolysis in insect cells are mutated to contain one or more mutations: S158T/A, I160T/V, K/T163S/A/T, Q165K/A, K169R, K171R, V173N, E175G, D176Q/E, D/E177T, T178G, G179D/E, S180A/T, G181D/E, D182S, G183V, L189E/I, Q/S191E, T/D192P, S/T193P, G/S194A, T/G195A, M196P, A197S/T, A198G/S, V199L, S200G, D/P201S/T, T/S202N/L, and E203T (consensus numbering in FIG. 1C).

In some embodiments, the engineered VP1/VP2 proteins may contain one or more of the following mutations: S158A, T163S, Q165A, S180T, L189I, T195A, A197S, A198G, P201S, and T202L (consensus number in FIG. 1C). (These residues correspond respectively to amino acid residues S157A, T162S, Q164A, S179T, L188I, T194A, A196S, A197G, P200S, and T201L according to the numbering of SEQ ID NO:1 (AAV6) or a corresponding sequence from another serotype aligned to show maximal homology to SEQ ID NO:1.)

The mutations described herein remove sites in the AAV capsid proteins susceptible to proteolytic cleavage in insect cells. Thus, a helper construct containing the modified Cap gene will give rise to rAAV products of higher purity and uniformity, as well as improved capsid protein.

It has been surprisingly found that the point mutations introduced herein to the AAV VP1/VP2 unique region (i.e., region common to VP1 and VP2 but absent in VP3) can also significantly improve the rAAV's potency through a mechanism that does not rely on solely on the prevention of proteolytic cleavage.

B. Modifications to Further Improvement of rAAV Production Yield

Additionally or alternatively, the VP1 coding sequence in the baculoviral helper construct is mutated in one or more codons in the region coding for the VP1 PLA2 domain such that the engineered PLA2 domain acquires higher enzymatic activity. It has been shown that higher PLA2 enzymatic activity may lead to a higher yield of rAAV in the insect cell production system.

The present disclosure provides a baculovirus-insect system in which the VP1 coding sequence is altered in the VP1 unique region (i.e., region present in VP1 but not in VP2 or VP3) to improve the production yield of the rAAV in insect cells. The VP1 unique region (corresponding to residues 1-137 of SEQ ID NO:1) contains the PLA2 domain, and the mutations in the region may increase the enzymatic activity of the PLA2 domain in the resultant VP1 protein.

In some embodiments, the baculoviral helper construct of the present disclosure provides helper functions for the production of rAAV6 or rAAV9 and the VP1 expression cassette on a helper construct includes a modified AAV6 or AAV9 Cap gene (Cap6 or Cap9, respectively) with a mutated PLA2 domain. The mutated PLA2 domain may comprise mutations relative to the wildtype at one or more positions in a region corresponding to residues 1-137 (e.g., 52-97 or 67-92) of SEQ ID NO: 1, where the positions are selected from a group consisting of residues 67, 81, 84, 85, and 92 (numbering of SEQ ID NO:1). In some embodiments, the AAV6 VP1 protein comprises one or more mutations selected from the group consisting of A67E, Q81R, K84D, A85S, and R92K (numbering according to SEQ ID NO:1). In particular embodiments, the AAV6 VP1 protein comprises all of the five mutations, such that its sequence in the region corresponding to residues 52-97 (SEQ ID NO:5) in SEQ ID NO:1 is as follows.

```
                                                  (SEQ ID NO: 6)
YLGPFNGLDK GEPVNEADAA ALEHDKAYDR QLDSGDNPYL
KYNHAD
```

This sequence is identical to the sequence in the corresponding region in AAV2 VP1. Thus, to generate a modified cap6 gene in the baculoviral AAV6 helper construct, one can replace the coding sequence for residues 52-97 or 67-92 of VP1 with the coding sequence for the corresponding amino acid sequence of AAV2, using well known molecular cloning techniques.

It has been surprisingly found that the point mutations introduced herein to the AAV VP1 unique region can significantly improve the VP1 PLA2 domain's enzymatic activity and also lead to significant improvement (e.g., two or more fold, three or more fold, four or more fold, or five or more fold) in the yield of the rAAV produced in insect cells.

In particular embodiments, the engineered Cap gene encodes an AAV6 VP1 protein containing both the aforementioned mutations in the PLA2 domain and the aforementioned mutations that remove the proteolytic sites. One exemplary modified AAV6 VP1 protein ("AAV6/2/9 VP1") has the following sequence (where V203 may be M203 or another amino acid instead):

```
                                                                  (SEQ ID NO: 7)
1     MAADGYLPDW LEDNLSEGIR EWWDLKPGAP KPKANQQKQD DGRGLVLPGY KYLGPFNGLD

61    KGEPVNEADA AALEHDKAYD RQLDSGDNPY LKYNHADAEF QERLQEDTSF GGNLGRAVFQ

121   AKKRVLEPFG LVEEGAKTAP GKKRPVEQSP QEPDSSAGIG KSGAQPAKKR LNFGQTGDTE

181   SVPDPQPIGE PPAAPSGVGS LTVASGGGAP MADNNEGADG VGNASGNWHC DSTWLGDRVI

241   TTSTRTWALP TYNNHLYKQI SSASTGASND NHYFGYSTPW GYFDFNRFHC HFSPRDWQRL

301   INNNWGFRPK RLNFKLFNIQ VKEVTTNDGV TTIANNLTST VQVFSDSEYQ LPYVLGSAHQ

361   GCLPPFPADV FMIPQYGYLT LNNGSQAVGR SSFYCLEYFP SQMLRTGNNF TFSYTFEDVP

421   FHSSYAHSQS LDRLMNPLID QYLYYLNRTQ NQSGSAQNKD LLFSRGSPAG MSVQPKNWLP

481   GPCYRQQRVS KTKTDNNNSN FTWTGASKYN LNGRESIINP GTAMASHKDD KDKFFPMSGV

541   MIFGKESAGA SNTALDNVMI TDEEEIKATN PVATERFGTV AVNLQSSSTD PATGDVHVMG

601   ALPGMVWQDR DVYLQGPIWA KIPHTDGHFH PSPLMGGFGL KHPPPQILIK NTPVPANPPA

661   EFSATKFASF ITQYSTGQVS VEIEWELQKE NSKRWNPEVQ YTSNYAKSAN VDFTVDNNGL

721   YTEPRPIGTR YLTRPL
```

Other exemplary modified AAV6 VP1 protein has the same sequence as SEQ ID NO:7 except that the start residue in position 1 is not present, or is T, L, V or another amino acid encoded by a non-canonical start codon such as a suboptimal start codon. A baculoviral helper construct encoding one of these modified AAV6 VP1 proteins can be used to produce rAAV6 or a pseudotyped or chimeric rAAV with improved potency and yield in insect cells.

In some embodiments, the engineered Cap gene encodes an AAV9 VP1 protein containing an AAV2 PLA2 domain. The wildtype AAV9 VP1 sequence (UniProtKB—Q6JC40 (Q6JC40_9VIRU)) is shown below, where the five amino acid residues differing from the corresponding ones in the AAV9/2 VP1 in the PLA2 domain are indicated with boldface and boxes:

(SEQ ID NO: 11)

```
  1 MAADGYLPDW LEDNLSEGIR EWWALKPGAP QPKANQQHQD NARGLVLPGY KYLGPGNGLD
 61 KGEPVNAADA AALEHDKAYD QQLKAGDNPY LKYNHADAEF QERLKEDTSF GGNLGRAVFQ
121 AKKRLLEPLG LVEEAAKTAP GKKRPVEQSP QEPDSSAGIG KSGAQPAKKR LNFGQTGDTE
181 SVPDPQPIGE PPAAPSGVGS LTMASGGGAP VADNNEGADG VGSSSGNWHC DSQWLGDRVI
241 TTSTRTWALP TYNNHLYKQI SNSTSGGSSN DNAYFGYSTP WGYFDFNRFH CHFSPRDWQR
301 LINNNWGFRP KRLNFKLFNI QVKEVTDNNG VKTIANNLTS TVQVFTDSDY QLPYVLGSAH
361 EGCLPPFPAD VFMIPQYGYL TLNDGSQAVG RSSFYCLEYF PSQMLRTGNN FQFSYEFENV
421 PFHSSYAHSQ SLDRLMNPLI DQYLYYLSKT INGSGQNQQT LKFSVAGPSN MAVQGRNYIP
481 GPSYRQQRVS TTVTQNNNSE FAWPGASSWA LNGRNSLMNP GPAMASHKEG EDRFFPLSGS
541 LIFGKQGTGR DNVDADKVMI TNEEEIKTTN PVATESYGQV ATNHQSAQAQ AQTGWVQNQG
601 ILPGMVWQDR DVYLQGPIWA KIPHTDGNFH PSPLMGGFGM KHPPPQILIK NTPVPADPPT
661 AFNKDKLNSF ITQYSTGQVS VEIEWELQKE NSKRWNPEIQ YTSNYYKSNN VEFAVNTEGV
721 YSEPRPIGTR YLTRNL
```

The wildtype AAV9 and AAV2 sequences in this region (residues 52-97 of SEQ ID NO:11) are shown below, where the five amino acid changes relative to wildtype AAV9 after the AAV2 sequence transplant are boldfaced and boxed:

AAV9:

(SEQ ID NO: 12)

YLGPGNGLDK GEPVNAADAA ALEHDKAYDQ QLKAGDNPYL KYNHAD

AAV2:

(SEQ ID NO: 6)

YLGPFNGLDK GEPVNEADAA ALEHDKAYDR QLDSGDNPYL KYNHAD

AAV6 AAP:

(SEQ ID NO: 8)

MATQSQSPTH NLSENLQQPP LLWDLLQWLQ

AAV9 AAP:

(SEQ ID NO: 9)

MATQSQSQTL NQSENLPQPP QVWDLLQWLQ

The complete AAV6 AAP wild-type sequence is shown below:

(SEQ ID NO: 10)

```
MATQSQSPTH NLSENLQQPP LLWDLLQWLQ AVAHQWQTIT KAPTEWVMPQ EIGIAIPHGW
ATESSPPAPE HGPCPPITTT STSKSPVLQR GPATTTTTSA TAPPGGILIS TDSTAISHHV
TGSDSSTTIG DSGPRDSTSS SSTSKSRRSR RMMASRPSLI TLPARFKSSR TRSTSCRTSS
ALRTRAASLR SRRTCS
```

In some embodiments, M203 in SEQ ID NO:11 may be replaced by V203 or another amino acid encoded by a noncanonical start codon.

C. Modifications to AAP

Figure 4A:
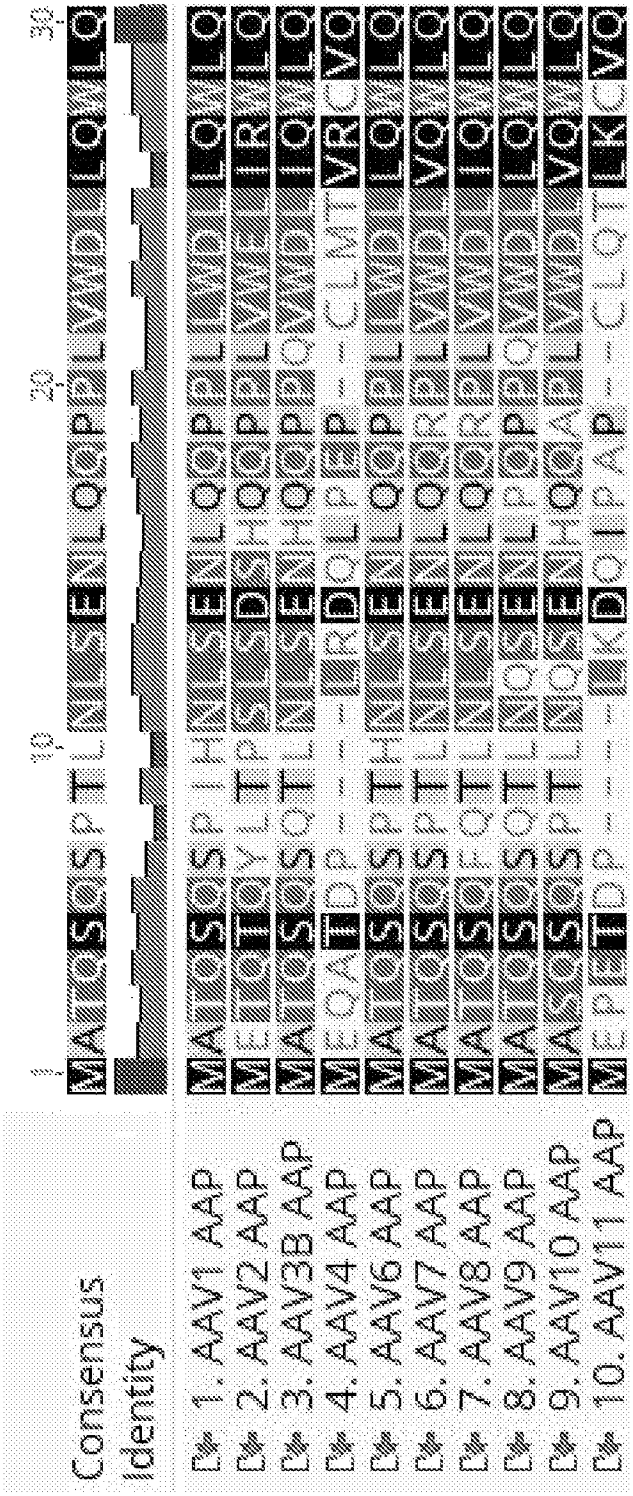
FIG. 4A shows the alignment of the assembly-activating protein (AAP) amino acid sequences from AAV serotypes 1, 2, 3B, 4, and 6-11 in the indicated region. Amino acid residue numbers are based on the consensus sequence. Multiple sequence alignment was generated using the Geneious software package and default settings for ClustalW alignment.

In some embodiments, the VP1 coding sequence also encodes an engineered AAP that has improved abilities to stabilize capsid protein and to facilitate capsid assembly. It has been shown that when residues 1-30 of AAV6 AAP ("AAP6") are changed to residues 1-30 AAV9 AAP ("AAP9"), the potency of the rAAV produced with the engineered helper construct is significantly increased. Residues 1-30 of AAP6 and AAP9 are shown below, where the six amino acid differences in wildtype AAP9 relative to wildtype AAP6 are indicated by boldface and boxes:

In some embodiments, the engineered AAP protein comprises one or more mutations at residues 8, 10, 12, 17, 21, and 22 (numbering based on consensus sequence in FIG. 4A). In further embodiments, the engineered AAP protein may comprise one or more of the following amino acid residues: Q8, L10, Q12, P17, Q21, and V22. In some embodiments, the engineered AAP protein may comprise one or more of the following mutations relative to the wildtype AAP sequence: P8Q, H10L, L12Q, Q17P, L21Q, and L22V. Unlimiting examples of engineered, improved AAP proteins are shown below:

(1) engineered AAP1 (AAP of serotype 1) comprising one or more of the following mutations: P8Q, I9T, H10L, L12Q, L16H, Q17P, L21Q, L22V, and L26I;

(2) engineered AAP2 (AAP of serotype 2) comprising one or more of the following mutations: E2A, T5S, Y7S, L8Q, P10L, S11N, L12Q, D14E, S15N, H16L, Q17P, L21Q, E24D, I26L, and R27Q;

(3) engineered AAP4 (AAP of serotype 4) comprising one or more of the following mutations: E2A, Q3T, A4Q, T5S, D6Q, P7S, L12Q, R13S, D14E, Q15N, L16H, P17Q, E18Q, C22V, L23W, M24D, T25L, V26I/L, R27Q, and C28W;

(4) engineered AAP6 (AAP of serotype 6) comprising one or more of the following mutations: P8Q, H10L, L12Q, L16H, Q17P, L21Q, L22V, and L26I;

(5) engineered AAP7 (AAP of serotype 7) comprising one or more of the following mutations: P8Q, L12Q, L16H, Q17P, L21Q, L22V, and L26I;

(6) engineered AAP8 (AAP of serotype 8) comprising one or more of the following mutations: F7S, L12Q, L16H, Q17P, R19P, L21Q, and I26L;

(7) engineered AAP10 (AAP of serotype 10) comprising one or more of the following mutations: S3T, P8Q, Q12L, L16H, Q17P, A19P, L21Q, and V26I/L; and (8) engineered AAP11 (AAP of serotype 11) comprising one or more of the following mutations: E2A, P3T, E4Q, T5S, D6Q, P7S, L12Q, R13S, D14E, Q15N, I16L/H, P17Q, A18Q, C22V, L23W, Q24D, T25L, L26I, K27Q, and C28W (see also FIG. 4B).

To generate engineered AAP protein, one can perform point mutations. Because the open reading frame encoding AAP is embedded in the Cap gene and is translated merely by a frameshift, one may also transplant from another serotype a portion of the Cap gene containing the coding sequence for an N terminal portion of AAP (e.g., residues 1-30, residues 1-28, residues 2-30, residues 2-28, etc.). In some embodiments, an AAV9 Cap gene portion coding for an AAV9 VP1/VP2 unique region (i.e., region common to VP1 and VP2 but absent in VP3), for example, a cap9 sequence comprising nucleotides 18-151 of SEQ ID NO:14 is substituted for the corresponding region of cap6, to generate an engineered VP1 expression cassette expressing an engineered AAV6 VP1 with a portion of AAV9 VP1 (e.g., so as to remove the proteolytic site(s) as discussed above), as well as an engineered AAP6 whose N-terminal 1-30 amino acid residues are now identical to those of AAP9. In some embodiments, the AAP mutations are generated by the same method as described above for the AAV9 Cap gene transplant.

Additional examples of capsid proteins are described in the Examples below.

II. Rep Protein Expression Cassettes

In mammalian cells, the Rep gene is transcribed into a Rep78-encoding RNA under the control of the mammalian p5 promoter and a Rep52-encoding RNA under the mammalian p19 promoter situated within the Rep78 ORF (see, e.g., Urabe et al., 2002, supra). The start codons for both Rep78 and Rep52 are ATG. It has been found that overexpression of Rep78 relative to Rep52 adversely impacts the yield of rAAV.

Failures of prior insect cell systems to produce rAAV with high yield have been attributed in part to the inability of these systems to achieve an optimal stoichiometry of the Rep proteins. In the present rAAV production systems, two separate expression cassettes are used for expressing Rep78 and Rep52. In some embodiments, the expression cassette for Rep78 and the expression cassette for Rep52 use insect promoters of the same or similar strengths; but the use of a weaker start codon (e.g., CTG, TTG, GTG, and ACG) for Rep78 helps achieve a desired Rep78:Rep52 protein ratio and high AAV yield. In certain embodiments, the two cassettes may use identical promoters such as those listed above for the capsid expression cassettes. In other embodiments, the Rep78 expression cassette has a canonical start codon (ATG) but uses a weaker promoter than the Rep52 expression cassette to achieve the desired stoichiometry.

In some embodiments, the Rep expression cassettes may contain additional regulatory elements such as those described above for the capsid protein expression cassettes.

In some embodiments, the coding sequences for the Rep proteins may be modified to further enhance AAV yield and potency. For example, the coding sequences may be codon-modified to increase mRNA stability, translation efficiency, or DNA vector stability in insect cells. To avoid production of Rep52 or any other by-product peptide from the Rep78 expression cassette, the Rep78 coding sequence may be mutated to remove the start codon for the embedded Rep52 ORF, any off-frame ATG sites, any undesired splice acceptor sites, any cryptic promoter sequences, and/or any destabilizing elements (see, e.g., Smith et al., supra). Conversely, the Rep52 coding sequence may be trimmed to remove any Rep78 coding sequence upstream of the Rep52 start codon.

The use of separate expression cassettes for Rep78 and Rep52, together with the use of a suboptimal start codon for Rep78, surprisingly leads to high yield production of potent rAAV.

III. Production of rAAV in Insect Cells

Production of rAAV in insect cells can be performed as described previously. See, e.g., Urabe et al., 2002 and 2006, supra; Chen et al., supra; Smith et al., supra; Mietzsch et al., supra; WO 2007/046703, WO 2007/148971, WO 2009/104964, WO 2013/036118, and WO 2008/024998, all of which are incorporated herein by reference in their entirety.

The insect cells in the production methods of the present disclosure comprise the dual baculoviral helper vectors described herein. The insect cells may be, without limitation, a cultured cell line such as BTI-TN-5B1-4 derived from *Trichoplusia ni* (High Five™, Thermo Fisher Scientific, Carlsbad, CA), Sf9 cells or Sf21 cells (both of which are derived from *Spodoptera frugiperda*), Sf9 or TN368 cells with mammalian-type glycan profiles (GlycoBac), or Sf-RVN cells (MilliporeSigma), Sf9-13F12 cells (Rhadovirus-free cells; Ma et al., *Virology* (2019) 536:125-33).

The rAAV may comprise within its capsid an AAV vector containing a transgene of interest. The transgene may encode a reporter protein for detection using biochemical (luciferase, SEAP) or imaging (GFP, Venus, dTomato) techniques. The transgene may encode a therapeutic protein, including, without limitation, a chimeric antigen receptor (CAR), a C-peptide or insulin, collagen VII, IGF-I, lipoprotein lipase, fibrinogen, prothrombin, Factor V, Factor VIII, Factor IX, Factor XI, Factor XII, Factor XIII, von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, plasminogen activator inhibitor-2, or any enzyme for treating a lysosome storage disease such as alpha-galactosidase A (for treating Fabry disease). The transgene may encode a sequence-specific binding protein (e.g., ZFP, TALE, TALEN, or dCas9). In some embodiments, the ZFP may be a ZFP transcription factor (e.g., a fusion protein in which a ZFP domain is fused to a transcription factor), a zinc finger nuclease (e.g., a fusion protein in which a ZFP domain is fused to a nuclease), or a ZFP base editor (e.g., a fusion protein in which a ZFP domain is fused to a nucleobase editor). The transgene may carry a sequence that can be incorporated into a specific site in the host genome (donor) by homologous recombination or non-homologous end joining. The transgene may encode an immunogenic protein for vaccination (e.g., a tumor antigen).

The AAV vector may comprise transcription regulatory elements (e.g., promoter and enhancer) that can direct and regulate expression of the transgene in human cells. The AAV vector may also comprise an AAV complete or partial inverted terminal repeat (ITR) on one or both ends of the transgene expression cassette. ITRs are required for packaging and viral integration into the host (human) genome. The AAV vector may be single-stranded or self-complementary.

IV. Pharmaceutical Compositions of rAAV

The rAAV capsids produced by the present methods can be formulated with a pharmaceutically acceptable carrier as a pharmaceutical composition. Formulations include, without limitation, suspensions in liquid or emulsified liquids. Pharmaceutically acceptable carriers include, for example, water, saline, dextrose, glycerol, sucrose, or the like, and combinations thereof. In addition, the composition may contain auxiliary substances, such as, wetting or emulsifying agents, pH buffering agents, stabilizing agents, or other reagents that enhance the effectiveness of the rAAV pharmaceutical composition.

The rAAV pharmaceutical composition may be delivered in vivo by administration to the patient, for example, by systemic administration (e.g., intravenous, intraperitoneal, intramuscular, subdermal, intrathecal, or intracranial infusion) or local injections. Alternatively, the rAAV can be delivered to cells ex vivo, such as cells explanted from a patient (e.g., lymphocytes, bone marrow aspirates, or tissue biopsy) or allogeneic cells (e.g., universal donor cells such as universal CAR T cells), followed by introduction of the treated cells into the patient, usually after selection for cells that have incorporated the rAAV vector.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. In case of conflict, the present specification, including definitions, will control. Generally, nomenclature used in connection with, and techniques of, cell and tissue culture, molecular biology, virology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents forms part of the common general knowledge in the art.

In order that this invention may be better understood, the following examples are set forth. These examples are for purposes of illustration only and are not to be construed as limiting the scope of the invention in any manner.

EXAMPLES

Example 1: Production of AAV in Sf9 Insect Cells

Currently, helper systems used for Sf9 AAV manufacturing rely on leaky scanning, alternative splicing, and/or internal promoters to express all the Rep and capsid proteins required for AAV production (Smith et al., supra; Chen et al., supra). Since AAV capsids assemble based on the stoichiometry of the available capsid proteins (Berns and Parrish, supra), we hypothesized that exerting greater control over the amount of VP1 expressed during rAAV production could increase the amount of VP1 incorporated into rAAV capsids and thereby the viral potency.

Figure 5:
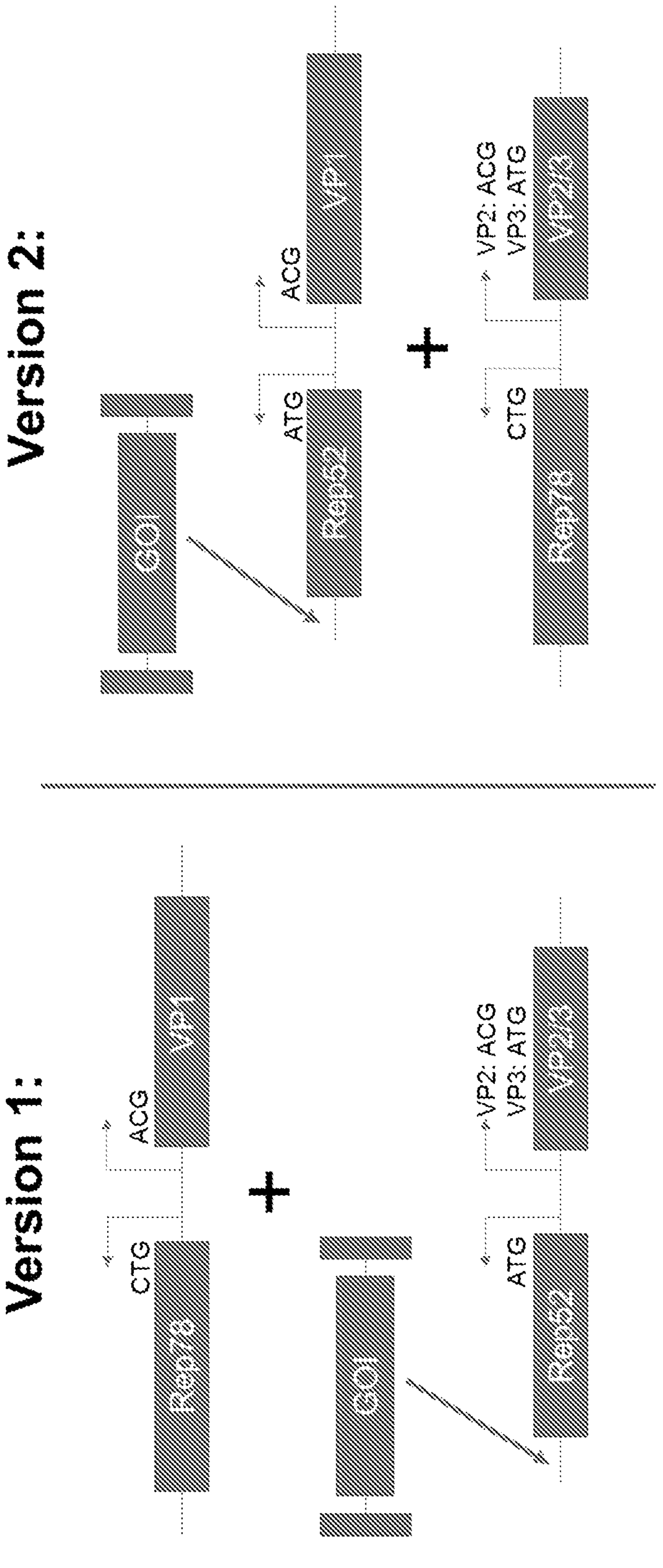
FIG. 5 is a schematic diagram showing two baculoviral helper systems for producing AAV in insect cells. The start codons for the Rep78, Rep52, VP1, and VP2/VP3 coding sequences, along with their transcription direction, are shown. Both systems involve two baculoviral vectors. A coding sequence for a recombinant AAV genome comprising a gene of interest (GOI) flanked by a pair of AAV inverted terminal repeats (ITR) can be placed on a separate baculoviral vector, or placed on the same vector as the Rep52 coding sequence.

To test this hypothesis, we cloned the coding sequences for individual capsid proteins into separate baculoviral vectors under the control of independent promoters. To allow greater control over the Rep proteins, we also cloned the coding sequences for individual Rep proteins into separate baculoviral vectors. In order to test various possible combinations of Rep and Cap coding sequences on different vectors, we constructed two versions of the baculoviral helper systems (FIG. 5).

In the first version, we paired the Rep78 expression cassette with the VP1 expression cassette and paired the Rep52 expression cassette with the VP2/VP3 expression cassette. In the second version, we paired the Rep52 expression cassette with the VP1 expression cassette and paired the Rep78 expression cassette with the VP2/VP3 expression cassette. Both Rep expression cassettes were under the control of a polyhedrin promoter. Both the VP1 and VP2/3 expression cassettes were under the control of a p10 promoter. With the exception of the VP2/3 gene, which utilizes the same leaky scanning mechanism as in the natural context of AAV replication, none of the Rep coding sequences and the VP1 coding sequence in these helper vectors relies on leaky scanning or alternative splicing for expression. In order to reduce the number of baculoviral vectors required for rAAV production, we incorporated the coding sequence for the AAV minigenome into the Rep52-expressing vector in both versions (FIG. 5). For the present study, the AAV minigenome contained the expression cassette for alpha-galactosidase A (GLA) or zinc finger proteins (ZFP) (SBS #65918 and SBS #57890, whose coding sequences were separated by a nucleotide linker encoding a T2A self-cleaving peptide in the transgene expression cassette; see WO 2018/102665 and WO 2020/072677). A GLA-encoding rAAV may be useful in gene therapy for Fabry disease. The ZFP bound to and repressed the expression of the mouse microtubule-associated protein tau (Mapt) gene.

The coding sequences in the expression cassettes and the encoded polypeptide sequences are as follows. In the VP1 coding sequence, the ATG start codon for the native VP3 ORF was changed to GTG, resulting in an M-to-V substitution. In the Rep78 coding sequence, the ATG start codon for the native Rep58 ORF was changed to GTG, also resulting in an M-to-V substitution. For the studies herein, the Rep gene was derived from AAV2.

Generation of rAAV and Determination of Relative Yield

Naïve Sf9 insect cells were inoculated with baculovirus-infected insect cells (BIIC1 and BIIC2 for cells respectively infected by the two baculoviral vectors). The ratio of BIIC1:BIIC2:naïve Sf9 cells for the inoculation was 1:1:10000. Cell cultures were incubated for six days. The cells were then harvested, resuspended and freeze/thawed three times. The cell lysate was treated with benzonase. Cell debris was removed by centrifugation. AAV was concentrated by the addition of PEG and NaCl followed by incubation on ice and centrifugation of precipitated virus. Concentrated virus was resuspended and applied to a CsCl gradient followed by overnight ultracentrifugation. Banded AAV was collected and dialyzed. Then qPCR was performed to titer the vector genome (vg) content. rAAV6 (with a GLA-encoding transgene) and rAAV9 (with a ZFP-encoding transgene) tested herein were obtained by these methods. Total AAV yield was calculated by multiplying the vg/mL by the total mL of the sample and expressed relative to the yield of the standard helper system 1, which expresses the AAV2 replicases and AAV6 capsid proteins and employs the one-vector system described in Smith et al., supra.

Additional rAAV serotypes, rAAV1, rAAV2, and rAAV3B, were obtained by the Version 2 method illustrated in FIG. 5. The VP1 in the rAAV1 and rAAV3B viruses contained an AAV2 PLA2 domain as described above. In the case of rAAV1, the VP1 and VP2 additionally contained an AAV9 transplant as described above to remove proteolytic sites. AAV2 and AAV3B did not appear susceptible to the proteolytic cleavage as observed with AAV1 and AAV6; and thus, their VP1/VP2 were not engineered to contain a transplanted AAV9 VP sequence). These three viruses also carried the same ZFP transgene as the rAAV9.

In the studies, the AAV genomes included ITR (inverted terminal repeats) from AAV2 and the insect cells expressed AAV2 replicases.

The capsid protein sequences of the rAAV6, rAAV9, rAAV1, rAAV2, and rAAV3B viruses herein are shown below. The capsid proteins of rAAV6 contained sequences from AAV2 and AAV9 as described in detail above. The capsid proteins of rAAV9, rAAV1, and rAAV3B also were engineered to contain sequences from other AAV serotypes, as indicated below.

Determination of rAAV6 Potency rAAV6 obtained by the method described above in this Example was applied to HepG2 cells at a multiplicity of infection (MOI or virus/cell based on the vg titer) of 900K. The cells were incubated for five days. The tissue culture supernatant was collected and assayed for GLA enzyme activity by measuring the level of a fluorescent reporter 4-methylumbelliferyl (4-MU) released from a GLA substrate. Enzymatic activity was calculated relative to activity with an rAAV sample produced by standard helper system 1.

Determination of rAAV9 Potency rAAV9 obtained by the method described above in this Example was applied to mouse cortical neurons at an MOI of 30K and incubated for six days. The cells were harvested for total RNA and used to generate cDNA. The cDNA was analyzed by qPCR for expression of mouse Mapt mRNA and zinc finger protein (ZFP) mRNA encoded by the AAV transgene. After normalizing the mRNA expression to the host cell RNA, potency was calculated relative to the rAAV9 produced by the AAV9 standard helper system (infra). The potency of the rAAV1, rAAV2, and rAAV3B viruses can be tested in the same manner as well.

Sequences of Rep and Capsid Proteins

The amino acid and coding sequences for the rAAV6, rAAV1, rAAV2, rAAV3B, and rAAV9 viruses tested herein are shown below.

```
rAAV6 VP1 coding sequence:
                                                  (SEQ ID NO: 15)
ACGGCTGCCGACGGTTATCTACCCGATTGGCTCGAGGACAACCTCTCTGA

GGGCATTCGCGAGTGGTGGGACCTCAAACCTGGAGCCCCGAAACCCAAAG

CCAACCAGCAAAAGCAGGACGACGGCCGGGGTCTGGTGCTTCCTGGGTAC

AAGTACCTCGGACCCTTCAACGGACTCGACAAGGGAGAGCCGGTCAACGA

GGCAGACGCCGCGGCCCTCGAGCACGACAAAGCCTACGACCGGCAGCTCG

ACAGCGGAGACAACCCGTACCTCAAGTACAACCACGCCGACGCGGAGTTT

CAGGAGCGCCTTCAAGAAGATACGTCTTTTGGGGGCAACCTCGGGCGAGC

AGTCTTCCAGGCCAAGAAGAGGGTTCTCGAACCTTTTGGTCTGGTTGAGG

AAGGTGCTAAGACCGCTCCTGGAAAGAAACGTCCGGTAGAGCAGTCGCCA

CAAGAGCCAGACTCCTCCGCGGGTATTGGCAAATCGGGTGCACAGCCCGC

TAAAAAGAGACTCAATTTCGGTCAGACTGGCGACACAGAGTCAGTCCCAG

ACCCTCAACCAATCGGAGAACCTCCCGCAGCCCCCTCAGGTGTGGGATCT

CTTACAGTGGCTTCAGGCGGTGGCGCACCAGTGGCAGACAATAACGAAGG

CGCCGACGGAGTGGGTAATGCCTCAGGAAATTGGCATTGCGATTCCACAT

GGCTGGGCGACAGAGTCATCACCACCAGCACCCGAACATGGGCCTTGCCC

ACCTATAACAACCACCTCTACAAGCAAATCTCCAGTGCTTCAACGGGGGC

CAGCAACGACAACCACTACTTCGGCTACAGCACCCCCTGGGGGTATTTTG

ATTTCAACAGATTCCACTGCCATTTCTCACCACGTGACTGGCAGCGACTC

ATCAACAACAATTGGGGATTCCGGCCCAAGAGACTCAACTTCAAGCTCTT
```

-continued

CAACATCCAAGTCAAGGAGGTCACGACGAATGATGGCGTCACGACCATCG

CTAATAACCTTACCAGCACGGTTCAAGTCTTCTCGGACTCGGAGTACCAG

TTGCCGTACGTCCTCGGCTCTGCGCACCAGGGCTGCCTCCCTCCGTTCCC

GGCGGACGTGTTCATGATTCCGCAGTACGGCTACCTAACGCTCAACAATG

GCAGCCAGGCAGTGGGACGGTCATCCTTTTACTGCCTGGAATATTTCCCA

TCGCAGATGCTGAGAACGGGCAATAACTTTACCTTCAGCTACACCTTCGA

GGACGTGCCTTTCCACAGCAGCTACGCGCACAGCCAGAGCCTGGACCGGC

TGATGAATCCTCTCATCGACCAGTACCTGTATTACCTGAACAGAACTCAG

AATCAGTCCGGAAGTGCCCAAAACAAGGACTTGCTGTTTAGCCGGGGGTC

TCCAGCTGGCATGTCTGTTCAGCCCAAAAACTGGCTACCTGGACCCTGTT

ACCGGCAGCAGCGCGTTTCTAAAACAAAAACAGACAACAACAACAGCAAC

TTTACCTGGACTGGTGCTTCAAAATATAACCTTAATGGGCGTGAATCTAT

AATCAACCCTGGCACTGCTATGGCCTCACACAAAGACGACAAAGACAAGT

TCTTTCCCATGAGCGGTGTCATGATTTTTGGAAAGGAGAGCGCCGGAGCT

TCAAACACTGCATTGGACAATGTCATGATCACAGACGAAGAGGAAATCAA

AGCCACTAACCCCGTGGCCACCGAAAGATTTGGGACTGTGGCAGTCAATC

TCCAGAGCAGCAGCACAGACCCTGCGACCGGAGATGTGCATGTTATGGGA

GCCTTACCTGGAATGGTGTGGCAAGACAGAGACGTATATCTGCAGGGTCC

TATTTGGGCCAAAATTCCTCACACGGATGGACACTTTCACCCGTCTCCTC

TCATGGGCGGCTTTGGACTTAAGCACCCGCCTCCTCAGATCCTCATCAAA

AACACGCCTGTTCCTGCGAATCCTCCGGCAGAGTTTTCGGCTACAAAGTT

TGCTTCATTCATCACCCAGTATTCCACAGGACAAGTGAGCGTGGAGATTG

AATGGGAGCTGCAGAAAGAAAACAGCAAACGCTGGAATCCCGAAGTGCAG

TATACATCTAACTATGCAAAATCTGCCAACGTTGATTTCACTGTGGACAA

CAATGGACTTTATACTGAGCCTCGCCCCATTGGCACCCGTTACCTCACCC

GTCCCCTGTAA rAAV6 VP1 polypeptide:

(SEQ ID NO: 16; X = M or T)

XAADGYLPDW LEDNLSEGIR EWWDLKPGAP KPKANQQKQD DGRGLVLPGY KYLGPFNGLD

KGEPVNEADA AALEHDKAYD RQLDSGDNPY LKYNHADAEF QERLQEDTSF GGNLGRAVFQ

AKKRVLEPFG LVEEGAKTAP GKKRPVEQSP QEPDSSAGIG KSGAQPAKKR LNFGQTGDTE

SVPDPQPIGE PPAAPSGVGS LTVASGGGAP VADNNEGADG VGNASGNWHC DSTWLGDRVI

TTSTRTWALP TYNNHLYKQI SSASTGASND NHYFGYSTPW GYFDFNRFHC HFSPRDWQRL

INNNWGFRPK RLNFKLFNIQ VKEVTTNDGV TTIANNLTST VQVFSDSEYQ LPYVLGSAHQ

GCLPPFPADV FMIPQYGYLT LNNGSQAVGR SSFYCLEYFP SQMLRTGNNF TFSYTFEDVP

FHSSYAHSQS LDRLMNPLID QYLYYLNRTQ NQSGSAQNKD LLFSRGSPAG MSVQPKNWLP

GPCYRQQRVS KTKTDNNNSN FTWTGASKYN LNGRESIINP GTAMASHKDD KDKFFPMSGV

MIFGKESAGA SNTALDNVMI TDEEEIKATN PVATERFGTV AVNLQSSSTD PATGDVHVMG

ALPGMVWQDR DVYLQGPIWA KIPHTDGHFH PSPLMGGFGL KHPPPQILIK NTPVPANPPA

EFSATKFASF ITQYSTGQVS VEIEWELQKE NSKRWNPEVQ YTSNYAKSAN VDFTVDNNGL

YTEPRPIGTR YLTRPL

-continued rAAV6 VP2/VP3 coding sequence:

(SEQ ID NO: 17)

ACGGCTCCTGGAAAGAAACGTCCGGTAGAGCAGTCGCCACAAGAGCCAGA

CTCCTCCGCGGGTATTGGCAAATCGGGTGCACAGCCCGCTAAAAAGAGAC

TCAATTTCGGTCAGACTGGCGACACAGAGTCAGTCCCAGACCCTCAACCA

ATCGGAGAACCTCCCGCAGCCCCCTCAGGTGTGGGATCTCTTACAATGGC

TTCAGGCGGTGGCGCACCAGTGGCAGACAATAACGAAGGCGCCGACGGAG

TGGGTAATGCCTCAGGAAATTGGCATTGCGATTCCACATGGCTGGGCGAC

AGAGTCATCACCACCAGCACCCGAACATGGGCCTTGCCCACCTATAACAA

CCACCTCTACAAGCAAATCTCCAGTGCTTCAACGGGGGCCAGCAACGACA

ACCACTACTTCGGCTACAGCACCCCCTGGGGGTATTTTGATTTCAACAGA

TTCCACTGCCATTTCTCACCACGTGACTGGCAGCGACTCATCAACAACAA

TTGGGGATTCCGGCCCAAGAGACTCAACTTCAAGCTCTTCAACATCCAAG

TCAAGGAGGTCACGACGAATGATGGCGTCACGACCATCGCTAATAACCTT

ACCAGCACGGTTCAAGTCTTCTCGGACTCGGAGTACCAGTTGCCGTACGT

CCTCGGCTCTGCGCACCAGGGCTGCCTCCCTCCGTTCCCGGCGGACGTGT

TCATGATTCCGCAGTACGGCTACCTAACGCTCAACAATGGCAGCCAGGCA

GTGGGACGGTCATCCTTTTACTGCCTGGAATATTTCCCATCGCAGATGCT

GAGAACGGGCAATAACTTTACCTTCAGCTACACCTTCGAGGACGTGCCTT

TCCACAGCAGCTACGCGCACAGCCAGAGCCTGGACCGGCTGATGAATCCT

CTCATCGACCAGTACCTGTATTACCTGAACAGAACTCAGAATCAGTCCGG

AAGTGCCCAAAACAAGGACTTGCTGTTTAGCCGGGGGTCTCCAGCTGGCA

TGTCTGTTCAGCCCAAAAACTGGCTACCTGGACCCTGTTACCGGCAGCAG

CGCGTTTCTAAAACAAAAACAGACAACAACAACAGCAACTTTACCTGGAC

TGGTGCTTCAAAATATAACCTTAATGGGCGTGAATCTATAATCAACCCTG

GCACTGCTATGGCCTCACACAAAGACGACAAAGACAAGTTCTTTCCCATG

AGCGGTGTCATGATTTTTGGAAAGGAGAGCGCCGGAGCTTCAAACACTGC

ATTGGACAATGTCATGATCACAGACGAAGAGGAAATCAAAGCCACTAACC

CCGTGGCCACCGAAAGATTTGGGACTGTGGCAGTCAATCTCCAGAGCAGC

AGCACAGACCCTGCGACCGGAGATGTGCATGTTATGGGAGCCTTACCTGG

AATGGTGTGGCAAGACAGAGACGTATATCTGCAGGGTCCTATTTGGGCCA

AAATTCCTCACACGGATGGACACTTTCACCCGTCTCCTCTCATGGGCGGC

TTTGGACTTAAGCACCCGCCTCCTCAGATCCTCATCAAAAACACGCCTGT

TCCTGCGAATCCTCCGGCAGAGTTTTCGGCTACAAAGTTTGCTTCATTCA

TCACCCAGTATTCCACAGGACAAGTGAGCGTGGAGATTGAATGGGAGCTG

CAGAAAGAAAACAGCAAACGCTGGAATCCCGAAGTGCAGTATACATCTAA

CTATGCAAAATCTGCCAACGTTGATTTCACTGTGGACAACAATGGACTTT

ATACTGAGCCTCGCCCCATTGGCACCCGTTACCTCACCCGTCCCCTGTAA

-continued rAAV6 VP2 polypeptide sequence:

(SEQ ID NO: 18; X = M or T)

XAPGKKRPVE QSPQEPDSSA GIGKSGAQPA KKRLNFGQTG DTESVPDPQP IGEPPAAPSG

VGSLTMASGG GAPVADNNEG ADGVGNASGN WHCDSTWLGD RVITTSTRTW ALPTYNNHLY

KQISSASTGA SNDNHYFGYS TPWGYFDFNR FHCHFSPRDW QRLINNNWGF RPKRLNFKLF

NIQVKEVTTN DGVTTIANNL TSTVQVFSDS EYQLPYVLGS AHQGCLPPFP ADVFMIPQYG

YLTLNNGSQA VGRSSFYCLE YFPSQMLRTG NNFTFSYTFE DVPFHSSYAH SQSLDRLMNP

LIDQYLYYLN RTQNQSGSAQ NKDLLFSRGS PAGMSVQPKN WLPGPCYRQQ RVSKTKTDNN

NSNFTWTGAS KYNLNGRESI INPGTAMASH KDDKDKFFPM SGVMIFGKES AGASNTALDN

VMITDEEEIK ATNPVATERF GTVAVNLQSS STDPATGDVH VMGALPGMVW QDRDVYLQGP

IWAKIPHTDG HFHPSPLMGG FGLKHPPPQI LIKNTPVPAN PPAEFSATKF ASFITQYSTG

QVSVEIEWEL QKENSKRWNP EVQYTSNYAK SANVDFTVDN NGLYTEPRPI GTRYLTRPL rAAV6 VP3 polypeptide sequence:

(SEQ ID NO: 19)

MASGGGAPVA DNNEGADGVG NASGNWHCDS TWLGDRVITT STRTWALPTY NNHLYKQISS

ASTGASNDNH YFGYSTPWGY FDFNRFHCHF SPRDWQRLIN NNWGFRPKRL NFKLFNIQVK

EVTTNDGVTT IANNLTSTVQ VFSDSEYQLP YVLGSAHQGC LPPFPADVFM IPQYGYLTLN

NGSQAVGRSS FYCLEYFPSQ MLRTGNNFTF SYTFEDVPFH SSYAHSQSLD RLMNPLIDQY

LYYLNRTQNQ SGSAQNKDLL FSRGSPAGMS VQPKNWLPGP CYRQQRVSKT KTDNNNSNFT

WTGASKYNLN GRESIINPGT AMASHKDDKD KFFPMSGVMI FGKESAGASN TALDNVMITD

EEEIKATNPV ATERFGTVAV NLQSSSTDPA TGDVHVMGAL PGMVWQDRDV YLQGPIWAKI

PHTDGHFHPS PLMGGFGLKH PPPQILIKNT PVPANPPAEF SATKFASFIT QYSTGQVSVE

IEWELQKENS KRWNPEVQYT SNYAKSANVD FTVDNNGLYT EPRPIGTRYL TRPL rAAV1 VP1/VP2/VP3 polypeptide sequences (transplanted AAV2 PLA2 domain is shown in box; transplanted AAV9 VP2/VP3 proteolytic resistant domain is italicized and boldfaced; the first amino acids of VP2 and VP3 (T138 and V203, respectively, in SEQ ID NO:24) are boldfaced and underlined):

(SEQ ID NO: 24)

TAADGYLPDW LEDNLSEGIR EWWDLKPGAP KPKANQQKQD DGRGLVLPGY KYLGPFNGLD

KGEPVNEADA AALEHDKAYD RQLDSGDNPY LKYNHADAEF QERLQEDTSF GGNLGRAVFQ

AKKRVLEPLG LVEEGAKTAP GKKRPVEQSP QEPDSS*AGIG KSGAQPAKKR LNFGQTGDTE*

*SVPDPQPIGE PPAAPSGVGS L*TVASGGGAP VADNNEGADG VGNASGNWHC DSTWLGDRVI

TTSTRTWALP TYNNHLYKQI SSASTGASND NHYFGYSTPW GYFDFNRFHC HFSPRDWQRL

INNNWGFRPK RLNFKLFNIQ VKEVTTNDGV TTIANNLTST VQVFSDSEYQ LPYVLGSAHQ

GCLPPFPADV FMIPQYGYLT LNNGSQAVGR SSFYCLEYFP SQMLRTGNNF TFSYTFEEVP

FHSSYAHSQS LDRLMNPLID QYLYYLNRTQ NQSGSAQNKD LLFSRGSPAG MSVQPKNWLP

GPCYRQQRVS KTKTDNNNSN FTWTGASKYN LNGRESIINP GTAMASHKDD EDKFFPMSGV

MIFGKESAGA SNTALDNVMI TDEEEIKATN PVATERFGTV AVNFQSSSTD PATGDVHAMG

ALPGMVWQDR DVYLQGPIWA KIPHTDGHFH PSPLMGGFGL KNPPPQILIK NTPVPANPPA

EFSATKFASF ITQYSTGQVS VEIEWELQKE NSKRWNPEVQ YTSNYAKSAN VDFTVDNNGL

YTEPRPIGTR YLTRPL rAAV2 VP1/VP2/VP3 polypeptide sequences (the first amino acids of VP2 and VP3 (T138 and V203, respectively, in SEQ ID NO:25) are boldfaced and underlined):

(SEQ ID NO: 25)

```
TAADGYLPDW LEDTLSEGIR QWWKLKPGPP PPKPAERHKD
DSRGLVLPGY KYLGPFNGLD KGEPVNEADA AALEHDKAYD
RQLDSGDNPY LKYNHADAEF QERLKEDTSF GGNLGRAVFQ
AKKRVLEPLG LVEEPVKTAP GKKRPVEHSP VEPDSSSGTG
KAGQQPARKR LNFGQTGDAD SVPDPQPLGQ PPAAPSGLGT
NTVATGSGAP VADNNEGADG VGNSSGNWHC DSTWLGDRVI
TTSTRTWALP TYNNHLYKQI SSQSGASNDN HYFGYSTPWG
YFDFNRFHCH FSPRDWQRLI NNNWGFRPKR LNFKLFNIQV
KEVTQNDGTT TIANNLTSTV QVFTDSEYQL PYVLGSAHQG
```

-continued

```
CLPPFPADVF MVPQYGYLTL NNGSQAVGRS SFYCLEYFPS
QMLRTGNNFT FSYTFEDVPF HSSYAHSQSL DRLMNPLIDQ
YLYYLSRINT PSGTTTQSRL QFSQAGASDI RDQSRNWLPG
PCYRQQRVSK TSADNNNSEY SWTGATKYHL NGRDSLVNPG
PAMASHKDDE EKFFPQSGVL IFGKQGSEKT NVDIEKVMIT
DEEEIRTINP VATEQYGSVS TNLQRGNRQA ATADVNTQGV
LPGMVWQDRD VYLQGPIWAK IPHTDGHFHP SPLMGGFGLK
HPPPQILIKN TPVPANPSTT FSAAKFASFI TQYSTGQVSV
EIEWELQKEN SKRWNPEIQY TSNYNKSVNV DFTVDINGVY
SEPRPIGTRY LTRNL
```

rAAV3B VP1/VP2/VP3 polypeptide sequences (transplanted AAV2 PLA2 domain is shown in box; the first amino acids of VP2 and VP3 (T138 and V203, respectively, in SEQ ID NO:26) are boldfaced and underlined):

(SEC ID NO: 26)

```
LAADGYLPDW LEDNLSEGIR EWWALKPGVP QPKANQQHQD NRRG[LVLPGY KYLGPFNGLD
KGEPVNEADA AALEHDKAYD RQLDSGDNPY LKYNHADAEF QERL]QEDTSF GGNLGRAVFQ
AKKRILEPLG LVEEAAKTAP GKKRPVDQSP QEPDSSSGVG KSGKQPARKR LNFGQTGDSE
SVPDPQPLGE PPAAPTSLGS NTVASGGGAP VADNNEGADG VGNSSGNWHC DSQWLGDRVI
TTSTRTWALP TYNNHLYKQI SSQSGASNDN HYFGYSTPWG YFDFNRFHCH FSPRDWQRLI
NNNWGFRPKK LSFKLFNIQV KEVTQNDGTT TIANNLTSTV QVFTDSEYQL PYVLGSAHQG
CLPPFPADVF MVPQYGYLTL NNGSQAVGRS SFYCLEYFPS QMLRTGNNFQ FSYTFEDVPF
HSSYAHSQSL DRLMNPLIDQ YLYYLNRTQG TTSGTTNQSR LLFSQAGPQS MSLQARNWLP
GPCYRQQRLS KTANDNNNSN FPWTAASKYH LNGRDSLVNP GPAMASHKDD EEKFFPMHGN
LIFGKEGTTA SNAELDNVMI TDEEEIRTTN PVATEQYGTV ANNLQSSNTA PTTRTVNDQG
ALPGMVWQDR DVYLQGPIWA KIPHTDGHFH PSPLMGGFGL KHPPPQIMIK NTPVPANPPT
TFSPAKFASF ITQYSTGQVS VEIEWELQKE NSKRWNPEIQ YTSNYNKSVN VDFTVDTNGV
YSEPRPIGTR YLTRNL
```

rAAV9 VP1/VP2/VP3 polypeptide sequences (transplanted AAV2 PLA2 domain is shown in box; the first amino acids of VP2 and VP3 (T138 and V203, respectively, in SEQ ID NO:27) are boldfaced and underlined):

(SEC ID NO: 27)

```
LAADGYLPDW LEDNLSEGIR EWWALKPGVP QPKANQQHQD NRRG[LVLPGY KYLGPFNGLD
KGEPVNEADA AALEHDKAYD RQLDSGDNPY LKYNHADAEF QERL]KEDTSF GGNLGRAVFQ
AKKRLLEPLG LVEEAAKTAP GKKRPVEQSP QEPDSSAGIG KSGAQPAKKR LNFGQTGDTE
SVPDPQPIGE PPAAPSGVGS LTVASGGGAP VADNNEGADG VGSSSGNWHC DSQWLGDRVI
TTSTRTWALP TYNNHLYKQI SNSTSGGSSN DNAYFGYSTP WGYFDFNRFH CHFSPRDWQR
LINNNWGFRP KRLNFKLFNI QVKEVTDNNG VKTIANNLTS TVQVFTDSDY QLPYVLGSAH
EGCLPPFPAD VFMIPQYGYL TLNDGSQAVG RSSFYCLEYF PSQMLRTGNN FQFSYEFENV
PFHSSYAHSQ SLDRLMNPLI DQYLYYLSKT INGSGQNQQT LKFSVAGPSN MAVQGRNYIP
GPSYRQQRVS TTVTQNNNSE FAWPGASSWA LNGRNSLMNP GPAMASHKEG EDRFFPLSGS
```

-continued

LIFGKQGTGR DNVDADKVMI TNEEEIKTTN PVATESYGQV ATNHQSAQAQ AQTGWVQNQG

ILPGMVWQDR DVYLQGPIWA KIPHTDGNFH PSPLMGGFGM KHPPPQILIK NTPVPADPPT

AFNKDKLNSF ITQYSTGQVS VEIEWELQKE NSKRWNPEIQ YTSNYYKSNN VEFAVNTEGV

YSEPRPIGTR YLTRNL

AAV2 Rep78 coding sequence:

(SEQ ID NO: 20)

CTGGCGGGGTTTTACGAGATTGTGATTAAGGTCCCCAGCGACCTTGACGA

GCATCTGCCCGGCATTTCTGACAGCTTTGTGAACTGGGTGGCCGAGAAGG

AGTGGGAGTTGCCGCCAGATTCTGACTTGGATCTGAATCTGATTGAGCAG

GCACCCCTGACCGTGGCCGAGAAGCTGCAGCGCGACTTTCTGACGGAGTG

GCGCCGTGTGAGTAAGGCCCCGGAGGCCCTTTTCTTTGTGCAATTTGAGA

AGGGAGAGAGCTACTTCCACTTACACGTGCTCGTGGAAACCACCGGGGTG

AAATCCTTAGTTTTGGGACGTTTCCTGAGTCAGATTCGCGAAAAACTGAT

TCAGAGAATTTACCGCGGGATCGAGCCGACTTTGCCAAACTGGTTCGCGG

TCACAAAGACCAGAAACGGCGCCGGAGGCGGGAACAAGGTGGTGGACGAG

TGCTACATCCCCAATTACTTGCTCCCCAAAACCCAGCCTGAGCTCCAGTG

GGCGTGGACTAATTTAGAACAGTATTTAAGCGCCTGTTTGAATCTCACGG

AGCGTAAACGGTTGGTGGCGCAGCATCTGACGCACGTGTCGCAGACGCAG

GAGCAGAACAAAGAGAATCAGAATCCCAATTCTGACGCGCCGGTGATCAG

ATCAAAAACTTCAGCCAGGTACGTGGAGCTGGTCGGGTGGCTCGTGGACA

AGGGGATTACCTCGGAGAAGCAGTGGATCCAGGAGGACCAGGCCTCATAC

ATCTCCTTCAATGCGGCCTCCAACTCGCGGTCCCAAATCAAGGCTGCCTT

GGACAATGCGGGAAAGATTATGAGCCTGACTAAAACCGCCCCCGACTACC

TGGTGGGCCAGCAGCCCGTGGAGGACATTTCCAGCAATCGGATTTATAAA

ATTTTGGAACTAAACGGGTACGATCCCCAATATGCGGCTTCCGTCTTTCT

-continued

GGGATGGGCCACGAAAAAGTTCGGCAAGAGGAACACCATCTGGCTGTTTG

GGCCTGCAACTACCGGGAAGACCAACATCGCGGAGGCCATAGCCCACACT

GTGCCCTTCTACGGGTGCGTAAACTGGACCAATGAGAACTTTCCCTTCAA

CGACTGTGTCGACAAGATGGTGATCTGGTGGGAGGAGGGGAAGATGACCG

CCAAGGTCGTGGAGTCGGCCAAAGCCATTCTCGGAGGAAGCAAGGTGCGC

GTGGACCAGAAATGCAAGTCCTCGGCCCAGATAGACCCGACTCCCGTGAT

CGTCACCTCCAACACCAACATGTGCGCCGTGATTGACGGGAACTCAACGA

CCTTCGAACACCAGCAGCCGTTGCAAGACCGGATGTTCAAATTTGAACTC

ACCCGCCGTCTGGATCATGACTTTGGGAAGGTCACCAAGCAGGAAGTCAA

AGACTTTTTCCGGTGGGCAAAGGATCACGTGGTTGAGGTGGAGCATGAAT

TCTACGTCAAAAAGGGTGGAGCCAAGAAAAGACCCGCCCCCAGTGACGCA

GATATAAGTGAGCCCAAACGGGTGCGCGAGTCAGTTGCGCAGCCATCGAC

GTCAGACGCGGAAGCTTCGATCAACTACGCAGACAGGTACCAAAACAAAT

GTTCTCGTCACGTGGGCATGAATCTGATGCTGTTTCCCTGCAGACAATGC

GAGAGAATGAATCAGAATTCAAATATCTGCTTCACTCACGGACAGAAAGA

CTGTTTAGAGTGCTTTCCCGTGTCAGAATCTCAACCCGTTTCTGTCGTCA

AAAAGGCGTATCAGAAACTGTGCTACATTCATCATATCATGGGAAAGGTG

CCAGACGCTTGCACTGCCTGCGATCTGGTCAATGTGGATTTGGATGACTG

CATCTTTGAACAATAA

AAV2 Rep78 polypeptide:

(SEQ ID NO: 21; X = M or L)

XAGFYEIVIK VPSDLDEHLP GISDSFVNWV AEKEWELPPD SDLDLNLIEQ APLTVAEKLQ

RDFLTEWRRV SKAPEALFFV QFEKGESYFH LHVLVETTGV KSLVLGRFLS QIREKLIQRI

YRGIEPTLPN WFAVTKTRNG AGGGNKVVDE CYIPNYLLPK TQPELQWAWT NLEQYLSACL

NLTERKRLVA QHLTHVSQTQ EQNKENQNPN SDAPVIRSKT SARYVELVGW LVDKGITSEK

QWIQEDQASY ISFNAASNSR SQIKAALDNA GKIMSLTKTA PDYLVGQQPV EDISSNRIYK

ILELNGYDPQ YAASVFLGWA TKKFGKRNTI WLFGPATTGK TNIAEAIAHT VPFYGCVNWT

NENFPFNDCV DKMVIWWEEG KMTAKVVESA KAILGGSKVR VDQKCKSSAQ IDPTPVIVTS

NTNMCAVIDG NSTTFEHQQP LQDRMFKFEL TRRLDHDFGK VTKQEVKDFF RWAKDHVVEV

EHEFYVKKGG AKKRPAPSDA DISEPKRVRE SVAQPSTSDA EASINYADRY QNKCSRHVGM

NLMLFPCRQC ERMNQNSNIC FTHGQKDCLE CFPVSESQPV SVVKKAYQKL CYIHHIMGKV

PDACTACDLV NVDLDDCIFE Q

AAV2 Rep52 coding sequence:

(SEQ ID NO: 22)

```
ATGGAGCTGGTCGGGTGGCTCGTGGACAAGGGGATTACCTCGGAGAAGCA
GTGGATCCAGGAGGACCAGGCCTCATACATCTCCTTCAATGCGGCCTCCA
ACTCGCGGTCCCAAATCAAGGCTGCCTTGGACAATGCGGGAAAGATTATG
AGCCTGACTAAAACCGCCCCCGACTACCTGGTGGGCCAGCAGCCCGTGGA
GGACATTTCCAGCAATCGGATTTATAAAATTTTGGAACTAAACGGGTACG
ATCCCCAATATGCGGCTTCCGTCTTTCTGGGATGGGCCACGAAAAAGTTC
GGCAAGAGGAACACCATCTGGCTGTTTGGGCCTGCAACTACCGGGAAGAC
CAACATCGCGGAGGCCATAGCCCACACTGTGCCCTTCTACGGGTGCGTAA
ACTGGACCAATGAGAACTTTCCCTTCAACGACTGTGTCGACAAGATGGTG
ATCTGGTGGGAGGAGGGGAAGATGACCGCCAAGGTCGTGGAGTCGGCCAA
AGCCATTCTCGGAGGAAGCAAGGTGCGCGTGGACCAGAAATGCAAGTCCT
CGGCCCAGATAGACCCGACTCCCGTGATCGTCACCTCCAACACCAACATG
TGCGCCGTGATTGACGGGAACTCAACGACCTTCGAACACCAGCAGCCGTT
GCAAGACCGGATGTTCAAATTTGAACTCACCCGCCGTCTGGATCATGACT
TTGGGAAGGTCACCAAGCAGGAAGTCAAAGACTTTTTCCGGTGGGCAAAG
GATCACGTGGTTGAGGTGGAGCATGAATTCTACGTCAAAAAGGGTGGAGC
CAAGAAAAGACCCGCCCCCAGTGACGCAGATATAAGTGAGCCCAAACGGG
TGCGCGAGTCAGTTGCGCAGCCATCGACGTCAGACGCGGAAGCTTCGATC
AACTACGCAGACAGGTACCAAAACAAATGTTCTCGTCACGTGGGCATGAA
TCTGATGCTGTTTCCCTGCAGACAATGCGAGAGAATGAATCAGAATTCAA
ATATCTGCTTCACTCACGGACAGAAAGACTGTTTAGAGTGCTTTCCCGTG
TCAGAATCTCAACCCGTTTCTGTCGTCAAAAAGGCGTATCAGAAACTGTG
CTACATTCATCATATCATGGGAAAGGTGCCAGACGCTTGCACTGCCTGCG
ATCTGGTCAATGTGGATTTGGATGACTGCATCTTTGAACAATAA
```

AAV2 Rep52 polypeptide:

(SEQ ID NO: 23)

```
MELVGWLVDK GITSEKQWIQ EDQASYISFN AASNSRSQIK AALDNAGKIM SLTKTAPDYL
VGQQPVEDIS SNRIYKILEL NGYDPQYAAS VFLGWATKKF GKRNTIWLFG PATTGKTNIA
EAIAHTVPFY GCVNWTNENF PFNDCVDKMV IWWEEGKMTA KVVESAKAIL GGSKVRVDQK
CKSSAQIDPT PVIVTSNTNM CAVIDGNSTT FEHQQPLQDR MFKFELTRRL DHDFGKVTKQ
EVKDFFRWAK DHVVEVEHEF YVKKGGAKKR PAPSDADISE PKRVRESVAQ PSTSDAEASI
NYADRYQNKC SRHVGMNLML FPCRQCERMN QNSNICFTHG QKDCLECFPV SESQPVSVVK
KAYQKLCYIH HIMGKVPDAC TACDLVNVDL DDCIFEQ
```

Results

We tested the ability of each version in FIG. 5 to produce rAAV6 and the potency of the resulting rAAV with respect to standard helper system 1 and standard helper system 2, which differs from standard helper system 1 in that its capsid expression cassettes use the AAV6/2/9 hybrid sequences described above. Surprisingly, the pairing of the Rep and Cap genes had a significant impact on both yield and potency. Version 1 had an approximately two-fold reduction in yield and eight-fold increase in potency, whereas Version 2 had an approximately four-fold increase in yield and five-fold increase in potency (Table 1). Comparison of the capsid ratios showed that the Version 1 rAAV6 had very little VP2 and a VP1:VP3 ratio similar to that observed with wildtype AAV (1:10). Recombinant AAV produced by the Version 2 system had a similar capsid ratio to that observed with standard helper system 2 (Table 1).

TABLE 1

Characterization of rAAV6*

| Helper | Relative Yield (N = 3) | Potency (N = 3) | Capsid ratio VP1 | VP2 | VP3 |
|---|---|---|---|---|---|
| Standard helper system 1 | 1.0 | 1.0 | 1 | 2 | 66 |
| Standard helper system 2 | 3.8 | 3.1 | 1 | 1.6 | 24 |
| Version 1 | 0.5 | 8.5 | 1 | 0.005 | 14 |
| Version 2 | 4.1 | 5.2 | 1 | 1.4 | 26 |

*The yield and potency numbers are averages of three independent production lots. The capsid ratios are from a single production lot.

For rAAV9, Version 1 had an approximately three-fold reduction in yield and similar potency, whereas Version 2 had an approximately four-fold increase in yield and two-fold decrease in potency, as compared to standard helper system 1 (Table 2). Comparison of the capsid ratios showed that the Version 1 rAAV9 had half as much VP2 as the AAV9 standard helper system and a VP1:VP3 ratio one half of that observed with wildtype AAV (1:10). Recombinant AAV9 produced by the Version 2 system had a similar capsid ratio to that observed with rAAV9 provided by the AAV9 standard helper system (Table 2). The AAV9 standard helper system was the same as the AAV6 standard helper system 2, except that instead of producing AAV6/2/9 hybrid capsid proteins, it produced hybrid AAV9 capsid proteins in which the VP1 protein was engineered to contain an AAV2 PLA2 domain as described above.

TABLE 2

| Characterization of rAAV9* | | | | | |
|---|---|---|---|---|---|
| | Relative Yield | Potency | Capsid ratio | | |
| Helper | (N = 6) | (N = 6) | VP1 | VP2 | VP3 |
| AAV9 standard helper | 1.0 | 1.0 | 1 | 1.7 | 18 |
| Version 1 | 0.3 | 0.9 | 1 | 0.8 | 20 |
| Version 2 | 4.0 | 0.5 | 1 | 1.5 | 26 |

*The yield and potency numbers and capsid ratios are from six dependent production lots.

Additional serotypes rAAV1, rAAV2 and rAAV3B were successfully produced by the Version 2 method of FIG. 5.

These data suggest that the pairing of Rep and Cap expression cassettes on a helper vector influences the yield and potency of produced rAAV. Furthermore, the data demonstrate that the Rep and Cap proteins can be successfully expressed from two separate baculoviral vectors and help produce infectious rAAV at high yield. Lastly, these data demonstrate that the production system described herein is broadly applicable to different AAV serotypes and is not restricted to the more extensively tested AAV6 and AAV9 versions.

TABLE 3

List of Sequences

| SEQ ID NO | Description |
|---|---|
| 1 | AAV6 VP1 amino acid sequence |
| 2 | AAV6 proteolytic site |
| 3 | AAV6 VP1/VP2 fragment |
| 4 | AAV9 VP1/VP2 fragment |
| 5 | AAV6 VP1 fragment |
| 6 | AAV2 VP1 fragment |
| 7 | AAV6/2/9 VP1 amino acid sequence |
| 8 | AAP6 residues 1-30 |
| 9 | AAP9 residues 1-30 |
| 10 | AAP6 amino acid sequence |
| 11 | AAV9 VP1 amino acid sequence |
| 12 | AAV9 VP1 fragment |
| 13 | Partial AAV6 Cap nucleotide sequence |
| 14 | Partial AAV9 Cap nucleotide sequence |
| 15 | VP1 coding sequence of rAAV6 in Example 1 |
| 16 | VP1 polypeptide sequence of rAAV6 in Example 1 |
| 17 | VP2/VP3 coding sequence of rAAV6 in Example 1 |
| 18 | VP2 polypeptide sequence of rAAV6 in Example 1 |
| 19 | VP3 polypeptide sequence of rAAV6 in Example 1 |
| 20 | AAV2 Rep78 coding sequence in Example 1 |
| 21 | AAV2 Rep78 polypeptide sequence in Example 1 |
| 22 | AAV2 Rep52 coding sequence in Example 1 |
| 23 | AAV2 Rep52 polypeptide sequence in Example 1 |
| 24 | VP1/VP2/VP3 polypeptide sequences of rAAV1 in Example 1 |
| 25 | VP1/VP2/VP3 polypeptide sequences of rAAV2 in Example 1 |
| 26 | VP1/VP2/VP3 polypeptide sequences of rAAV3B in Example 1 |
| 27 | VP1/VP2/VP3 polypeptide sequences of rAAV9 in Example 1 |
| 28-73 | Sequences in figures |

What is claimed is:

1. An insect cell comprising a first baculoviral vector comprising an expression cassette encoding Rep78 and a second baculoviral vector comprising an expression cassette encoding Rep52, wherein (i) the first vector comprises an expression cassette encoding VP2 and VP3 but not VP1 and the second vector comprises an expression cassette encoding VP1 but not VP2 and VP3, or (ii) the first vector comprises an expression cassette encoding VP1 but not VP2 and VP3 and the second vector comprises an expression cassette encoding VP2 and VP3 but not VP1.

2. The insect cell of claim 1, wherein the Rep78 expression cassette and the Rep52 expression cassette comprise identical insect promoters.

3. The insect cell of claim 1, wherein the Rep78 expression cassette comprises a non-canonical start codon for the Rep78 coding sequence, wherein the non-canonical start codon is optionally ACG, TTG, GTG, or CTG.

4. The insect cell of claim 1, wherein the VP1 expression cassette and the VP2 and VP3 expression cassette comprise identical promoters.

5. The insect cell of claim 1, wherein the encoded VP1, VP2, and VP3 comprise amino acid sequences from a same AAV serotype, or from more than one AAV serotype.

6. The insect cell of claim 5, wherein the encoded VP1, VP2, and/or VP3 comprise amino acid sequences from AAV1, AAV2, AAV3, AAV3B, AAV6, and/or AAV9.

7. The insect cell of claim 1, wherein the encoded Rep78 and Rep52 are derived from a different AAV serotype from the encoded VP1, VP2, and/or VP3.

8. The insect cell of claim 1, wherein (i) the VP1 comprises the sequence set forth in SEQ ID NO:1, 7, or 16 with or without the first amino acid residue;

the VP2 comprises amino acid residues 138-736 or 139-736 of the sequences set forth in SEQ ID NO:1 or 7, or comprises the sequence set forth in SEQ ID NO:18 with or without the first amino acid residue; and the VP3 comprises amino acid residues of 204-736 or 205-736 of the sequence set forth in SEQ ID NO:1 or amino acid residues 203-736 or 204-736 of the sequence set forth in SEQ ID NO:7, or comprises the sequence set forth in SEQ ID NO:19 with or without the first amino acid residue; or (ii) the VP1 comprises the sequence set forth in SEQ ID NO:24 with or without the first amino acid residue;

the VP2 comprises amino acid residues 138-736 or 139-736 of the sequence set forth in SEQ ID NO:24; and the VP3 comprises amino acid residues of 203-736 or 204-736 of the sequence set forth in SEQ ID NO:24; or (iii) the VP1 comprises the sequence set forth in SEQ ID NO:25 with or without the first amino acid residue;

the VP2 comprises amino acid residues 138-735 or 139-735 of the sequence set forth in SEQ ID NO:25; and the VP3 comprises 203-735 or 204-735 of the sequence set forth in SEQ ID NO:25; or (iv) the VP1 comprises the sequence set forth in SEQ ID NO:26 with or without the first amino acid residue;

the VP2 comprises amino acid residues 138-736 or 139-736 of the sequence set forth in SEQ ID NO:26; and the VP3 comprises amino acid residues of 203-736 or 204-736 of the sequence set forth in SEQ ID NO:26; or (v) the VP1 comprises the sequence set forth in SEQ ID NO:27 with or without the first amino acid residue;

the VP2 comprises amino acid residues 138-736 or 139-736 of the sequence set forth in SEQ ID NO:27; and the VP3 comprises amino acid residues of 203-736 or 204-736 of the sequence set forth in SEQ ID NO:27; and optionally wherein the Rep78 comprises the sequence set forth in SEQ ID NO:21 with or without the first amino acid residue; and/or the Rep52 comprises the sequence set forth in SEQ ID NO:23 with or without the first amino acid residue.

9. The insect cell of claim 1, wherein the Rep 78, Rep52, VP1, and VP2 and VP3 expression cassettes each comprises a promoter selected from a polyhedrin promoter, an IE-1 promoter, and a p10 promoter.

10. The insect cell of claim 1, wherein the insect cell is an Sf9 or Sf21 cell.

11. The insect cell of claim 1, further comprising a coding sequence for a recombinant AAV genome, wherein the recombinant AAV genome comprises an expression cassette for a transgene of interest that is operably linked to a mammalian promoter, and an AAV inverted terminal repeat (ITR) on both termini.

12. The insect cell of claim 11, wherein the transgene of interest encodes a therapeutic protein, optionally selected from a zinc finger protein (ZFP) transcription factor and a protein whose function is lacking or deficient in a genetic disease.

13. The insect cell of claim 11, wherein the transgene of interest encodes a gene editing protein, optionally selected from a zinc finger nuclease, a ZFP deaminase, a ZFP recombinase, a transcription activator-like effector nuclease, and a CRISPR Cas protein.

14. A method of producing a recombinant AAV virion, comprising:

providing an insect cell of claim 11, culturing the insect cell under conditions that allow expression of the recombinant AAV genome and packaging of the recombinant AAV genome within an AAV capsid comprising the encoded VP1, VP2, and VP3, and isolating the produced recombinant AAV virion from the culture.

15. A recombinant AAV virion produced in the insect cell of claim 11.

16. A pharmaceutical composition comprising the recombinant AAV virion of claim 15 and a pharmaceutically acceptable carrier.

17. A combination of baculoviral vectors of claim 1, wherein:

the first baculoviral vector comprises an expression cassette encoding Rep78 and an expression cassette encoding VP2 and VP3 but not VP1 and a second baculoviral vector comprises an expression cassette encoding Rep52 and an expression cassette encoding VP1 but not VP2 or VP3; or a first baculoviral vector comprises an expression cassette encoding Rep78 and an expression cassette encoding VP1 but not VP2 or VP3 and the second baculoviral vector comprises an expression cassette encoding Rep52 and an expression cassette encoding VP2 and VP3 but not VP1.

18. The insect cell of claim 1, wherein the VP1 comprises the sequence set forth in SEQ ID NO: 7, 16, 24, 25, 26, or 27 with or without the first amino acid residue.

19. An insect cell comprising a first baculoviral vector comprising an expression cassette encoding Rep78 and a second baculoviral vector comprising an expression cassette encoding Rep52, wherein the first vector comprises an expression cassette encoding VP2 and VP3 but not VP1 and the second vector comprises an expression cassette encoding VP1 but not VP2 and VP3.

20. An insect cell comprising a first baculoviral vector comprising an expression cassette encoding Rep52 and a second baculoviral vector comprising an expression cassette encoding Rep78, wherein the first vector comprises an expression cassette encoding VP2 and VP3 but not VP1 and the second vector comprises an expression cassette encoding VP1 but not VP2 and VP3.

* * * * *

SEQUENCE LISTING

```
<160> NUMBER OF SEQ ID NOS: 73

<210> SEQ ID NO 1
<211> LENGTH: 737
<212> TYPE: PRT
<213> ORGANISM: Unknown
<220> FEATURE:
<221> NAME/KEY: source
<223> OTHER INFORMATION: /note="Description of Unknown:
      VP1 protein sequence"
<220> FEATURE:
<221> NAME/KEY: VARIANT
<222> LOCATION: (1)..(1)
<223> OTHER INFORMATION: /replace="Thr" or "Leu" or "Val"
<220> FEATURE:
<221> NAME/KEY: SITE
<222> LOCATION: (1)..(737)
<223> OTHER INFORMATION: /note="Variant residues given in the sequence
      have no preference with respect to those in the annotations
      for variant positions"

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

-continued

```
Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Val Val Ala Ser Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Asn
        435                 440                 445

Arg Thr Gln Asn Gln Ser Gly Ser Ala Gln Asn Lys Asp Leu Leu Phe
    450                 455                 460

Ser Arg Gly Ser Pro Ala Gly Met Ser Val Gln Pro Lys Asn Trp Leu
465                 470                 475                 480
```

-continued

Pro Gly Pro Cys Tyr Arg Gln Gln Arg Val Ser Lys Thr Lys Thr Asp
485 490 495

Asn Asn Asn Ser Asn Phe Thr Trp Thr Gly Ala Ser Lys Tyr Asn Leu
500 505 510

Asn Gly Arg Glu Ser Ile Ile Asn Pro Gly Thr Ala Met Ala Ser His
515 520 525

Lys Asp Asp Lys Asp Lys Phe Phe Pro Met Ser Gly Val Met Ile Phe
530 535 540

Gly Lys Glu Ser Ala Gly Ala Ser Asn Thr Ala Leu Asp Asn Val Met
545 550 555 560

Ile Thr Asp Glu Glu Glu Ile Lys Ala Thr Asn Pro Val Ala Thr Glu
565 570 575

Arg Phe Gly Thr Val Ala Val Asn Leu Gln Ser Ser Ser Thr Asp Pro
580 585 590

Ala Thr Gly Asp Val His Val Met Gly Ala Leu Pro Gly Met Val Trp
595 600 605

Gln Asp Arg Asp Val Tyr Leu Gln Gly Pro Ile Trp Ala Lys Ile Pro
610 615 620

His Thr Asp Gly His Phe His Pro Ser Pro Leu Met Gly Gly Phe Gly
625 630 635 640

Leu Lys His Pro Pro Pro Gln Ile Leu Ile Lys Asn Thr Pro Val Pro
645 650 655

Ala Asn Pro Pro Ala Glu Phe Ser Ala Thr Lys Phe Ala Ser Phe Ile
660 665 670

Thr Gln Tyr Ser Thr Gly Gln Val Ser Val Glu Ile Glu Trp Glu Leu
675 680 685

Gln Lys Glu Asn Ser Lys Arg Trp Asn Pro Glu Val Gln Tyr Thr Ser
690 695 700

Asn Tyr Ala Lys Ser Ala Asn Val Asp Phe Thr Val Asp Asn Asn Gly
705 710 715 720

Leu Tyr Thr Glu Pro Arg Pro Ile Gly Thr Arg Tyr Leu Thr Arg Pro
725 730 735

Leu

<210> SEQ ID NO 2
<211> LENGTH: 10
<212> TYPE: PRT
<213> ORGANISM: Adeno-associated virus 6

<400> SEQUENCE: 2

Pro Gln Pro Leu Gly Glu Pro Pro Ala Thr
1 5 10

<210> SEQ ID NO 3
<211> LENGTH: 45
<212> TYPE: PRT
<213> ORGANISM: Adeno-associated virus 6

<400> SEQUENCE: 3

Ser Gly Ile Gly Lys Thr Gly Gln Gln Pro Ala Lys Lys Arg Leu Asn
1 5 10 15

Phe Gly Gln Thr Gly Asp Ser Glu Ser Val Pro Asp Pro Gln Pro Leu
20 25 30

Gly Glu Pro Pro Ala Thr Pro Ala Ala Val Gly Pro Thr
35 40 45

-continued

<210> SEQ ID NO 4
<211> LENGTH: 45
<212> TYPE: PRT
<213> ORGANISM: Adeno-associated virus 9

<400> SEQUENCE: 4

```
Ala Gly Ile Gly Lys Ser Gly Ala Gln Pro Ala Lys Lys Arg Leu Asn
1               5                   10                  15

Phe Gly Gln Thr Gly Asp Thr Glu Ser Val Pro Asp Pro Gln Pro Ile
            20                  25                  30

Gly Glu Pro Pro Ala Ala Pro Ser Gly Val Gly Ser Leu
        35                  40                  45
```

<210> SEQ ID NO 5
<211> LENGTH: 46
<212> TYPE: PRT
<213> ORGANISM: Adeno-associated virus 6

<400> SEQUENCE: 5

```
Tyr Leu Gly Pro Phe Asn Gly Leu Asp Lys Gly Glu Pro Val Asn Ala
1               5                   10                  15

Ala Asp Ala Ala Ala Leu Glu His Asp Lys Ala Tyr Asp Gln Gln Leu
            20                  25                  30

Lys Ala Gly Asp Asn Pro Tyr Leu Arg Tyr Asn His Ala Asp
        35                  40                  45
```

<210> SEQ ID NO 6
<211> LENGTH: 46
<212> TYPE: PRT
<213> ORGANISM: Adeno-associated virus 2

<400> SEQUENCE: 6

```
Tyr Leu Gly Pro Phe Asn Gly Leu Asp Lys Gly Glu Pro Val Asn Glu
1               5                   10                  15

Ala Asp Ala Ala Ala Leu Glu His Asp Lys Ala Tyr Asp Arg Gln Leu
            20                  25                  30

Asp Ser Gly Asp Asn Pro Tyr Leu Lys Tyr Asn His Ala Asp
        35                  40                  45
```

<210> SEQ ID NO 7
<211> LENGTH: 736
<212> TYPE: PRT
<213> ORGANISM: Unknown
<220> FEATURE:
<221> NAME/KEY: source
<223> OTHER INFORMATION: /note="Description of Unknown:
      VP1 protein sequence"

<400> SEQUENCE: 7

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95
```

-continued

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Val Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510
```

-continued

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 8
<211> LENGTH: 30
<212> TYPE: PRT
<213> ORGANISM: Adeno-associated virus 6

<400> SEQUENCE: 8

Met Ala Thr Gln Ser Gln Ser Pro Thr His Asn Leu Ser Glu Asn Leu
1               5                   10                  15

Gln Gln Pro Pro Leu Leu Trp Asp Leu Leu Gln Trp Leu Gln
            20                  25                  30

<210> SEQ ID NO 9
<211> LENGTH: 30
<212> TYPE: PRT
<213> ORGANISM: Adeno-associated virus 9

<400> SEQUENCE: 9

Met Ala Thr Gln Ser Gln Ser Gln Thr Leu Asn Gln Ser Glu Asn Leu
1               5                   10                  15

Pro Gln Pro Pro Gln Val Trp Asp Leu Leu Gln Trp Leu Gln
            20                  25                  30

<210> SEQ ID NO 10
<211> LENGTH: 196
<212> TYPE: PRT
<213> ORGANISM: Adeno-associated virus 6

<400> SEQUENCE: 10

```
Met Ala Thr Gln Ser Gln Ser Pro Thr His Asn Leu Ser Glu Asn Leu
1               5                   10                  15

Gln Gln Pro Pro Leu Leu Trp Asp Leu Leu Gln Trp Leu Gln Ala Val
            20                  25                  30

Ala His Gln Trp Gln Thr Ile Thr Lys Ala Pro Thr Glu Trp Val Met
        35                  40                  45

Pro Gln Glu Ile Gly Ile Ala Ile Pro His Gly Trp Ala Thr Glu Ser
    50                  55                  60

Ser Pro Pro Ala Pro Glu His Gly Pro Cys Pro Pro Ile Thr Thr Thr
65                  70                  75                  80

Ser Thr Ser Lys Ser Pro Val Leu Gln Arg Gly Pro Ala Thr Thr Thr
                85                  90                  95

Thr Thr Ser Ala Thr Ala Pro Pro Gly Gly Ile Leu Ile Ser Thr Asp
            100                 105                 110

Ser Thr Ala Ile Ser His His Val Thr Gly Ser Asp Ser Ser Thr Thr
        115                 120                 125

Ile Gly Asp Ser Gly Pro Arg Asp Ser Thr Ser Ser Ser Ser Thr Ser
    130                 135                 140

Lys Ser Arg Arg Ser Arg Arg Met Met Ala Ser Arg Pro Ser Leu Ile
145                 150                 155                 160

Thr Leu Pro Ala Arg Phe Lys Ser Ser Arg Thr Arg Ser Thr Ser Cys
                165                 170                 175

Arg Thr Ser Ser Ala Leu Arg Thr Arg Ala Ala Ser Leu Arg Ser Arg
            180                 185                 190

Arg Thr Cys Ser
        195
```

<210> SEQ ID NO 11
<211> LENGTH: 736
<212> TYPE: PRT
<213> ORGANISM: Adeno-associated virus 9

<400> SEQUENCE: 11

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160
```

-continued

```
Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575
```

```
Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 12
<211> LENGTH: 46
<212> TYPE: PRT
<213> ORGANISM: Adeno-associated virus 9

<400> SEQUENCE: 12

Tyr Leu Gly Pro Gly Asn Gly Leu Asp Lys Gly Glu Pro Val Asn Ala
1               5                   10                  15

Ala Asp Ala Ala Ala Leu Glu His Asp Lys Ala Tyr Asp Gln Gln Leu
            20                  25                  30

Lys Ala Gly Asp Asn Pro Tyr Leu Lys Tyr Asn His Ala Asp
        35                  40                  45


<210> SEQ ID NO 13
<211> LENGTH: 183
<212> TYPE: DNA
<213> ORGANISM: Adeno-associated virus 6

<400> SEQUENCE: 13

aagagccaga ctcctcctcg ggcattggca agacaggcca gcagcccgct aaaaagagac      60

tcaattttgg tcagactggc gactcagagt cagtccccga cccacaacct ctcggagaac     120

ctccagcaac cccgctgct gtgggaccta ctacaatggc ttcaggcggt ggcgcaccaa     180

tgg                                                                   183


<210> SEQ ID NO 14
<211> LENGTH: 183
<212> TYPE: DNA
<213> ORGANISM: Adeno-associated virus 9

<400> SEQUENCE: 14

aagagccaga ctcctccgcg ggtattggca aatcgggtgc acagcccgct aaaaagagac      60

tcaatttcgg tcagactggc gacacagagt cagtcccaga ccctcaacca atcggagaac     120

ctcccgcagc cccctcaggt gtgggatctc ttacaatggc ttcaggcggt ggcgcaccaa     180

tgg                                                                   183
```

<210> SEQ ID NO 15
<211> LENGTH: 2211
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15
acggctgccg acggttatct acccgattgg ctcgaggaca acctctctga gggcattcgc 60
gagtggtggg acctcaaacc tggagccccg aaacccaaag ccaaccagca aaagcaggac 120
gacggccggg gtctggtgct tcctgggtac aagtacctcg gacccttcaa cggactcgac 180
aagggagagc cggtcaacga ggcagacgcc gcggccctcg agcacgacaa agcctacgac 240
cggcagctcg acagcggaga caacccgtac ctcaagtaca accacgccga cgcggagttt 300
caggagcgcc ttcaagaaga tacgtctttt gggggcaacc tcgggcgagc agtcttccag 360
gccaagaaga gggttctcga accttttggt ctggttgagg aaggtgctaa gaccgctcct 420
ggaaagaaac gtccggtaga gcagtcgcca caagagccag actcctccgc gggtattggc 480
aaatcgggtg cacagcccgc taaaaagaga ctcaatttcg gtcagactgg cgacacagag 540
tcagtcccag accctcaacc aatcggagaa cctcccgcag ccccctcagg tgtgggatct 600
cttacagtgg cttcaggcgg tggcgcacca gtggcagaca ataacgaagg cgccgacgga 660
gtgggtaatg cctcaggaaa ttggcattgc gattccacat ggctgggcga cagagtcatc 720
accaccagca cccgaacatg ggccttgccc acctataaca accacctcta caagcaaatc 780
tccagtgctt caacgggggc cagcaacgac aaccactact tcggctacag cacccccctgg 840 gggtattttg atttcaacag attccactgc catttctcac cacgtgactg gcagcgactc 900
atcaacaaca attggggatt ccggcccaag agactcaact tcaagctctt caacatccaa 960
gtcaaggagg tcacgacgaa tgatggcgtc acgaccatcg ctaataacct taccagcacg 1020
gttcaagtct tctcggactc ggagtaccag ttgccgtacg tcctcggctc tgcgcaccag 1080
ggctgcctcc ctccgttccc ggcggacgtg ttcatgattc cgcagtacgg ctacctaacg 1140
ctcaacaatg gcagccaggc agtgggacgg tcatcctttt actgcctgga atatttccca 1200
tcgcagatgc tgagaacggg caataacttt accttcagct acaccttcga ggacgtgcct 1260
ttccacagca gctacgcgca cagccagagc ctggaccggc tgatgaatcc tctcatcgac 1320
cagtacctgt attacctgaa cagaactcag aatcagtccg gaagtgccca aaacaaggac 1380
ttgctgttta gccgggggtc tccagctggc atgtctgttc agcccaaaaa ctggctacct 1440
ggaccctgtt accggcagca gcgcgtttct aaaacaaaaa cagacaacaa caacagcaac 1500
tttacctgga ctggtgcttc aaaatataac cttaatgggc gtgaatctat aatcaaccct 1560
ggcactgcta tggcctcaca caaagacgac aaagacaagt tctttcccat gagcggtgtc 1620
atgatttttg gaaaggagag cgccggagct tcaaacactg cattggacaa tgtcatgatc 1680
acagacgaag aggaaatcaa agccactaac cccgtggcca ccgaaagatt tgggactgtg 1740
gcagtcaatc tccagagcag cagcacagac cctgcgaccg gagatgtgca tgttatggga 1800
gccttacctg gaatggtgtg gcaagacaga gacgtatatc tgcagggtcc tatttgggcc 1860
aaaattcctc acacggatgg acactttcac ccgtctcctc tcatgggcgg ctttggactt 1920
aagcacccgc ctcctcagat cctcatcaaa aacacgcctg ttcctgcgaa tcctccggca 1980
gagttttcgg ctacaaagtt tgcttcattc atcacccagt attccacagg acaagtgagc 2040
gtggagattg aatgggagct gcagaaagaa aacagcaaac gctggaatcc cgaagtgcag 2100
tatacatcta actatgcaaa atctgccaac gttgatttca ctgtggacaa caatggactt 2160
tatactgagc ctcgccccat tggcacccgt tacctcaccc gtcccctgta a 2211

<210> SEQ ID NO 16
<211> LENGTH: 736
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (1)..(1)
<223> OTHER INFORMATION: /replace="Thr"
<220> FEATURE:
<221> NAME/KEY: SITE
<222> LOCATION: (1)..(736)
<223> OTHER INFORMATION: /note="Variant residues given in the sequence have no preference with respect to those in the annotations for variant positions"

<400> SEQUENCE: 16

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Glu Ala Asp Ala Ala Ala Leu Glu His Asp Lys Ala Tyr Asp
65 70 75 80

Arg Gln Leu Asp Ser Gly Asp Asn Pro Tyr Leu Lys Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Phe Gly Leu Val Glu Glu Gly Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

Ala Ala Pro Ser Gly Val Gly Ser Leu Thr Val Ala Ser Gly Gly Gly
195 200 205

Ala Pro Val Ala Asp Asn Asn Glu Gly Ala Asp Gly Val Gly Asn Ala
210 215 220

Ser Gly Asn Trp His Cys Asp Ser Thr Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Ser Ala Ser Thr Gly Ala Ser Asn Asp Asn His
260 265 270

-continued

```
Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685
```

```
Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 17
<211> LENGTH: 1800
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

acggctcctg gaaagaaacg tccggtagag cagtcgccac aagagccaga ctcctccgcg     60

ggtattggca aatcgggtgc acagcccgct aaaaagagac tcaatttcgg tcagactggc    120

gacacagagt cagtcccaga ccctcaacca atcggagaac ctcccgcagc cccctcaggt    180

gtgggatctc ttacaatggc ttcaggcggt ggcgcaccag tggcagacaa taacgaaggc    240

gccgacggag tgggtaatgc ctcaggaaat tggcattgcg attccacatg gctgggcgac    300

agagtcatca ccaccagcac ccgaacatgg gccttgccca cctataacaa ccacctctac    360

aagcaaatct ccagtgcttc aacgggggcc agcaacgaca accactactt cggctacagc    420

accccctggg ggtattttga tttcaacaga ttccactgcc atttctcacc acgtgactgg    480

cagcgactca tcaacaacaa ttggggattc cggcccaaga gactcaactt caagctcttc    540

aacatccaag tcaaggaggt cacgacgaat gatggcgtca cgaccatcgc taataacctt    600

accagcacgg ttcaagtctt ctcggactcg gagtaccagt tgccgtacgt cctcggctct    660

gcgcaccagg gctgcctccc tccgttcccg gcggacgtgt tcatgattcc gcagtacggc    720

tacctaacgc tcaacaatgg cagccaggca gtgggacggt catcctttta ctgcctggaa    780

tatttcccat cgcagatgct gagaacgggc aataacttta ccttcagcta caccttcgag    840

gacgtgcctt tccacagcag ctacgcgcac agccagagcc tggaccggct gatgaatcct    900

ctcatcgacc agtacctgta ttacctgaac agaactcaga atcagtccgg aagtgcccaa    960

aacaaggact tgctgtttag ccgggggtct ccagctggca tgtctgttca gcccaaaaac   1020

tggctacctg gaccctgtta ccggcagcag cgcgtttcta aaacaaaaac agacaacaac   1080

aacagcaact ttacctggac tggtgcttca aaatataacc ttaatgggcg tgaatctata   1140

atcaaccctg gcactgctat ggcctcacac aaagacgaca aagacaagtt ctttcccatg   1200

agcggtgtca tgatttttgg aaaggagagc gccggagctt caaacactgc attggacaat   1260

gtcatgatca cagacgaaga ggaaatcaaa gccactaacc ccgtggccac cgaaagattt   1320

gggactgtgg cagtcaatct ccagagcagc agcacagacc ctgcgaccgg agatgtgcat   1380

gttatgggag ccttacctgg aatggtgtgg caagacagag acgtatatct gcagggtcct   1440

atttgggcca aaattcctca cacggatgga cactttcacc cgtctcctct catgggcggc   1500

tttggactta agcacccgcc tcctcagatc ctcatcaaaa acacgcctgt tcctgcgaat   1560

cctccggcag agttttcggc tacaaagttt gcttcattca tcacccagta ttccacagga   1620

caagtgagcg tggagattga atgggagctg cagaaagaaa acagcaaacg ctggaatccc   1680

gaagtgcagt atacatctaa ctatgcaaaa tctgccaacg ttgatttcac tgtggacaac   1740
```

-continued aatggacttt atactgagcc tcgccccatt ggcacccgtt acctcacccg tcccctgtaa 1800

<210> SEQ ID NO 18
<211> LENGTH: 599
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (1)..(1)
<223> OTHER INFORMATION: /replace="Thr"
<220> FEATURE:
<221> NAME/KEY: SITE
<222> LOCATION: (1)..(599)
<223> OTHER INFORMATION: /note="Variant residues given in the sequence have no preference with respect to those in the annotations for variant positions"

<400> SEQUENCE: 18

```
Met Ala Pro Gly Lys Lys Arg Pro Val Glu Gln Ser Pro Gln Glu Pro
1               5                   10                  15

Asp Ser Ser Ala Gly Ile Gly Lys Ser Gly Ala Gln Pro Ala Lys Lys
            20                  25                  30

Arg Leu Asn Phe Gly Gln Thr Gly Asp Thr Glu Ser Val Pro Asp Pro
        35                  40                  45

Gln Pro Ile Gly Glu Pro Pro Ala Ala Pro Ser Gly Val Gly Ser Leu
    50                  55                  60

Thr Met Ala Ser Gly Gly Gly Ala Pro Val Ala Asp Asn Asn Glu Gly
65                  70                  75                  80

Ala Asp Gly Val Gly Asn Ala Ser Gly Asn Trp His Cys Asp Ser Thr
                85                  90                  95

Trp Leu Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Ala Ser Thr
        115                 120                 125

Gly Ala Ser Asn Asp Asn His Tyr Phe Gly Tyr Ser Thr Pro Trp Gly
    130                 135                 140

Tyr Phe Asp Phe Asn Arg Phe His Cys His Phe Ser Pro Arg Asp Trp
145                 150                 155                 160

Gln Arg Leu Ile Asn Asn Asn Trp Gly Phe Arg Pro Lys Arg Leu Asn
                165                 170                 175

Phe Lys Leu Phe Asn Ile Gln Val Lys Glu Val Thr Thr Asn Asp Gly
            180                 185                 190

Val Thr Thr Ile Ala Asn Asn Leu Thr Ser Thr Val Gln Val Phe Ser
        195                 200                 205

Asp Ser Glu Tyr Gln Leu Pro Tyr Val Leu Gly Ser Ala His Gln Gly
    210                 215                 220

Cys Leu Pro Pro Phe Pro Ala Asp Val Phe Met Ile Pro Gln Tyr Gly
225                 230                 235                 240

Tyr Leu Thr Leu Asn Asn Gly Ser Gln Ala Val Gly Arg Ser Ser Phe
                245                 250                 255

Tyr Cys Leu Glu Tyr Phe Pro Ser Gln Met Leu Arg Thr Gly Asn Asn
            260                 265                 270

Phe Thr Phe Ser Tyr Thr Phe Glu Asp Val Pro Phe His Ser Ser Tyr
        275                 280                 285
```

```
Ala His Ser Gln Ser Leu Asp Arg Leu Met Asn Pro Leu Ile Asp Gln
    290                 295                 300

Tyr Leu Tyr Tyr Leu Asn Arg Thr Gln Asn Gln Ser Gly Ser Ala Gln
305                 310                 315                 320

Asn Lys Asp Leu Leu Phe Ser Arg Gly Ser Pro Ala Gly Met Ser Val
                325                 330                 335

Gln Pro Lys Asn Trp Leu Pro Gly Pro Cys Tyr Arg Gln Gln Arg Val
            340                 345                 350

Ser Lys Thr Lys Thr Asp Asn Asn Asn Ser Asn Phe Thr Trp Thr Gly
        355                 360                 365

Ala Ser Lys Tyr Asn Leu Asn Gly Arg Glu Ser Ile Ile Asn Pro Gly
    370                 375                 380

Thr Ala Met Ala Ser His Lys Asp Asp Lys Asp Lys Phe Phe Pro Met
385                 390                 395                 400

Ser Gly Val Met Ile Phe Gly Lys Glu Ser Ala Gly Ala Ser Asn Thr
                405                 410                 415

Ala Leu Asp Asn Val Met Ile Thr Asp Glu Glu Glu Ile Lys Ala Thr
            420                 425                 430

Asn Pro Val Ala Thr Glu Arg Phe Gly Thr Val Ala Val Asn Leu Gln
        435                 440                 445

Ser Ser Ser Thr Asp Pro Ala Thr Gly Asp Val His Val Met Gly Ala
    450                 455                 460

Leu Pro Gly Met Val Trp Gln Asp Arg Asp Val Tyr Leu Gln Gly Pro
465                 470                 475                 480

Ile Trp Ala Lys Ile Pro His Thr Asp Gly His Phe His Pro Ser Pro
                485                 490                 495

Leu Met Gly Gly Phe Gly Leu Lys His Pro Pro Pro Gln Ile Leu Ile
            500                 505                 510

Lys Asn Thr Pro Val Pro Ala Asn Pro Pro Ala Glu Phe Ser Ala Thr
        515                 520                 525

Lys Phe Ala Ser Phe Ile Thr Gln Tyr Ser Thr Gly Gln Val Ser Val
    530                 535                 540

Glu Ile Glu Trp Glu Leu Gln Lys Glu Asn Ser Lys Arg Trp Asn Pro
545                 550                 555                 560

Glu Val Gln Tyr Thr Ser Asn Tyr Ala Lys Ser Ala Asn Val Asp Phe
                565                 570                 575

Thr Val Asp Asn Asn Gly Leu Tyr Thr Glu Pro Arg Pro Ile Gly Thr
            580                 585                 590

Arg Tyr Leu Thr Arg Pro Leu
        595


<210> SEQ ID NO 19
<211> LENGTH: 534
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Met Ala Ser Gly Gly Gly Ala Pro Val Ala Asp Asn Asn Glu Gly Ala
1               5                   10                  15

Asp Gly Val Gly Asn Ala Ser Gly Asn Trp His Cys Asp Ser Thr Trp
            20                  25                  30
```

```
Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Ala Ser Thr Gly
    50                  55                  60

Ala Ser Asn Asp Asn His Tyr Phe Gly Tyr Ser Thr Pro Trp Gly Tyr
65                  70                  75                  80

Phe Asp Phe Asn Arg Phe His Cys His Phe Ser Pro Arg Asp Trp Gln
                85                  90                  95

Arg Leu Ile Asn Asn Asn Trp Gly Phe Arg Pro Lys Arg Leu Asn Phe
            100                 105                 110

Lys Leu Phe Asn Ile Gln Val Lys Glu Val Thr Thr Asn Asp Gly Val
        115                 120                 125

Thr Thr Ile Ala Asn Asn Leu Thr Ser Thr Val Gln Val Phe Ser Asp
    130                 135                 140

Ser Glu Tyr Gln Leu Pro Tyr Val Leu Gly Ser Ala His Gln Gly Cys
145                 150                 155                 160

Leu Pro Pro Phe Pro Ala Asp Val Phe Met Ile Pro Gln Tyr Gly Tyr
                165                 170                 175

Leu Thr Leu Asn Asn Gly Ser Gln Ala Val Gly Arg Ser Ser Phe Tyr
            180                 185                 190

Cys Leu Glu Tyr Phe Pro Ser Gln Met Leu Arg Thr Gly Asn Asn Phe
        195                 200                 205

Thr Phe Ser Tyr Thr Phe Glu Asp Val Pro Phe His Ser Ser Tyr Ala
    210                 215                 220

His Ser Gln Ser Leu Asp Arg Leu Met Asn Pro Leu Ile Asp Gln Tyr
225                 230                 235                 240

Leu Tyr Tyr Leu Asn Arg Thr Gln Asn Gln Ser Gly Ser Ala Gln Asn
                245                 250                 255

Lys Asp Leu Leu Phe Ser Arg Gly Ser Pro Ala Gly Met Ser Val Gln
            260                 265                 270

Pro Lys Asn Trp Leu Pro Gly Pro Cys Tyr Arg Gln Gln Arg Val Ser
        275                 280                 285

Lys Thr Lys Thr Asp Asn Asn Asn Ser Asn Phe Thr Trp Thr Gly Ala
    290                 295                 300

Ser Lys Tyr Asn Leu Asn Gly Arg Glu Ser Ile Ile Asn Pro Gly Thr
305                 310                 315                 320

Ala Met Ala Ser His Lys Asp Asp Lys Asp Lys Phe Phe Pro Met Ser
                325                 330                 335

Gly Val Met Ile Phe Gly Lys Glu Ser Ala Gly Ala Ser Asn Thr Ala
            340                 345                 350

Leu Asp Asn Val Met Ile Thr Asp Glu Glu Glu Ile Lys Ala Thr Asn
        355                 360                 365

Pro Val Ala Thr Glu Arg Phe Gly Thr Val Ala Val Asn Leu Gln Ser
    370                 375                 380

Ser Ser Thr Asp Pro Ala Thr Gly Asp Val His Val Met Gly Ala Leu
385                 390                 395                 400

Pro Gly Met Val Trp Gln Asp Arg Asp Val Tyr Leu Gln Gly Pro Ile
                405                 410                 415

Trp Ala Lys Ile Pro His Thr Asp Gly His Phe His Pro Ser Pro Leu
            420                 425                 430

Met Gly Gly Phe Gly Leu Lys His Pro Pro Pro Gln Ile Leu Ile Lys
        435                 440                 445
```

-continued

```
Asn Thr Pro Val Pro Ala Asn Pro Pro Ala Glu Phe Ser Ala Thr Lys
    450                 455                 460

Phe Ala Ser Phe Ile Thr Gln Tyr Ser Thr Gly Gln Val Ser Val Glu
465                 470                 475                 480

Ile Glu Trp Glu Leu Gln Lys Glu Asn Ser Lys Arg Trp Asn Pro Glu
                485                 490                 495

Val Gln Tyr Thr Ser Asn Tyr Ala Lys Ser Ala Asn Val Asp Phe Thr
            500                 505                 510

Val Asp Asn Asn Gly Leu Tyr Thr Glu Pro Arg Pro Ile Gly Thr Arg
        515                 520                 525

Tyr Leu Thr Arg Pro Leu
    530


<210> SEQ ID NO 20
<211> LENGTH: 1866
<212> TYPE: DNA
<213> ORGANISM: Adeno-associated virus 2

<400> SEQUENCE: 20

ctggcggggt tttacgagat tgtgattaag gtccccagcg accttgacga gcatctgccc     60

ggcatttctg acagctttgt gaactgggtg gccgagaagg agtgggagtt gccgccagat    120

tctgacttgg atctgaatct gattgagcag gcaccccctga ccgtggccga gaagctgcag   180

cgcgactttc tgacggagtg gcgccgtgtg agtaaggccc cggaggccct tttctttgtg    240

caatttgaga agggagagag ctacttccac ttacacgtgc tcgtggaaac caccggggtg    300

aaatccttag ttttgggacg tttcctgagt cagattcgcg aaaaactgat tcagagaatt    360

taccgcggga tcgagccgac tttgccaaac tggttcgcgg tcacaaagac cagaaacggc    420

gccggaggcg ggaacaaggt ggtggacgag tgctacatcc ccaattactt gctccccaaa    480

acccagcctg agctccagtg ggcgtggact aatttagaac agtatttaag cgcctgtttg    540

aatctcacgg agcgtaaacg gttggtggcg cagcatctga cgcacgtgtc gcagacgcag    600

gagcagaaca aagagaatca gaatcccaat tctgacgcgc cggtgatcag atcaaaaact    660

tcagccaggt acgtggagct ggtcgggtgg ctcgtggaca aggggattac ctcggagaag    720

cagtggatcc aggaggacca ggcctcatac atctccttca atgcggcctc caactcgcgg    780

tcccaaatca aggctgcctt ggacaatgcg ggaaagatta tgagcctgac taaaaccgcc    840

cccgactacc tggtgggcca gcagcccgtg gaggacattt ccagcaatcg gatttataaa    900

attttggaac taaacgggta cgatccccaa tatgcggctt ccgtctttct gggatgggcc    960

acgaaaaagt tcggcaagag gaacaccatc tggctgtttg ggcctgcaac taccgggaag   1020

accaacatcg cggaggccat agcccacact gtgcccttct acgggtgcgt aaactggacc   1080

aatgagaact ttcccttcaa cgactgtgtc gacaagatgg tgatctggtg ggaggagggg   1140

aagatgaccg ccaaggtcgt ggagtcggcc aaagccattc tcggaggaag caaggtgcgc   1200

gtggaccaga aatgcaagtc ctcggcccag atagacccga ctcccgtgat cgtcacctcc   1260

aacaccaaca tgtgcgccgt gattgacggg aactcaacga ccttcgaaca ccagcagccg   1320

ttgcaagacc ggatgttcaa atttgaactc acccgccgtc tggatcatga ctttgggaag   1380

gtcaccaagc aggaagtcaa agactttttc cggtgggcaa aggatcacgt ggttgaggtg   1440

gagcatgaat tctacgtcaa aaagggtgga gccaagaaaa gacccgcccc cagtgacgca   1500

gatataagtg agcccaaacg ggtgcgcgag tcagttgcgc agccatcgac gtcagacgcg   1560
```

-continued

```
gaagcttcga tcaactacgc agacaggtac caaaacaaat gttctcgtca cgtgggcatg   1620

aatctgatgc tgtttccctg cagacaatgc gagagaatga atcagaattc aaatatctgc   1680

ttcactcacg gacagaaaga ctgtttagag tgctttcccg tgtcagaatc tcaacccgtt   1740

tctgtcgtca aaaaggcgta tcagaaactg tgctacattc atcatatcat gggaaaggtg   1800

ccagacgctt gcactgcctg cgatctggtc aatgtggatt tggatgactg catctttgaa   1860

caataa                                                              1866


<210> SEQ ID NO 21
<211> LENGTH: 621
<212> TYPE: PRT
<213> ORGANISM: Adeno-associated virus 2
<220> FEATURE:
<221> NAME/KEY: VARIANT
<222> LOCATION: (1)..(1)
<223> OTHER INFORMATION: /replace="Leu"
<220> FEATURE:
<221> NAME/KEY: SITE
<222> LOCATION: (1)..(621)
<223> OTHER INFORMATION: /note="Variant residues given in the sequence
      have no preference with respect to those in the annotations
      for variant positions"

<400> SEQUENCE: 21

Met Ala Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Leu Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Leu Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Leu Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Val Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255
```

-continued

```
Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
    610                 615                 620
```

<210> SEQ ID NO 22
<211> LENGTH: 1194
<212> TYPE: DNA
<213> ORGANISM: Adeno-associated virus 2

<400> SEQUENCE: 22
atggagctgg tcgggtggct cgtggacaag ggggattacct cggagaagca gtggatccag 60
gaggaccagg cctcatacat ctccttcaat gcggcctcca actcgcggtc ccaaatcaag 120
gctgccttgg acaatgcggg aaagattatg agcctgacta aaaccgcccc cgactacctg 180
gtgggccagc agcccgtgga ggacatttcc agcaatcgga tttataaaat tttggaacta 240
aacgggtacg atccccaata tgcggcttcc gtctttctgg gatgggccac gaaaaagttc 300
ggcaagagga acaccatctg gctgtttggg cctgcaacta ccgggaagac caacatcgcg 360
gaggccatag cccacactgt gcccttctac gggtgcgtaa actggaccaa tgagaacttt 420
cccttcaacg actgtgtcga caagatggtg atctggtggg aggaggggaa gatgaccgcc 480
aaggtcgtgg agtcggccaa agccattctc ggaggaagca aggtgcgcgt ggaccagaaa 540
tgcaagtcct cggcccagat agacccgact cccgtgatcg tcacctccaa caccaacatg 600
tgcgccgtga ttgacgggaa ctcaacgacc ttcgaacacc agcagccgtt gcaagaccgg 660
atgttcaaat ttgaactcac ccgccgtctg gatcatgact ttgggaaggt caccaagcag 720
gaagtcaaag actttttccg gtgggcaaag gatcacgtgg ttgaggtgga gcatgaattc 780
tacgtcaaaa agggtggagc caagaaaaga cccgccccca gtgacgcaga tataagtgag 840
cccaaacggg tgcgcgagtc agttgcgcag ccatcgacgt cagacgcgga agcttcgatc 900
aactacgcag acaggtacca aaacaaatgt tctcgtcacg tgggcatgaa tctgatgctg 960
tttccctgca gacaatgcga gagaatgaat cagaattcaa atatctgctt cactcacgga 1020
cagaaagact gtttagagtg ctttcccgtg tcagaatctc aacccgtttc tgtcgtcaaa 1080
aaggcgtatc agaaactgtg ctacattcat catatcatgg gaaaggtgcc agacgcttgc 1140
actgcctgcg atctggtcaa tgtggatttg gatgactgca tctttgaaca ataa 1194

<210> SEQ ID NO 23
<211> LENGTH: 397
<212> TYPE: PRT
<213> ORGANISM: Adeno-associated virus 2

<400> SEQUENCE: 23

Met Glu Leu Val Gly Trp Leu Val Asp Lys Gly Ile Thr Ser Glu Lys
1 5 10 15

Gln Trp Ile Gln Glu Asp Gln Ala Ser Tyr Ile Ser Phe Asn Ala Ala
20 25 30

Ser Asn Ser Arg Ser Gln Ile Lys Ala Ala Leu Asp Asn Ala Gly Lys
35 40 45

Ile Met Ser Leu Thr Lys Thr Ala Pro Asp Tyr Leu Val Gly Gln Gln
50 55 60

Pro Val Glu Asp Ile Ser Ser Asn Arg Ile Tyr Lys Ile Leu Glu Leu
65 70 75 80

Asn Gly Tyr Asp Pro Gln Tyr Ala Ala Ser Val Phe Leu Gly Trp Ala
85 90 95

Thr Lys Lys Phe Gly Lys Arg Asn Thr Ile Trp Leu Phe Gly Pro Ala
100 105 110

Thr Thr Gly Lys Thr Asn Ile Ala Glu Ala Ile Ala His Thr Val Pro
115 120 125

Phe Tyr Gly Cys Val Asn Trp Thr Asn Glu Asn Phe Pro Phe Asn Asp
130 135 140

```
Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
    290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Ser Asn Ile Cys
                325                 330                 335

Phe Thr His Gly Gln Lys Asp Cys Leu Glu Cys Phe Pro Val Ser Glu
            340                 345                 350

Ser Gln Pro Val Ser Val Val Lys Lys Ala Tyr Gln Lys Leu Cys Tyr
        355                 360                 365

Ile His His Ile Met Gly Lys Val Pro Asp Ala Cys Thr Ala Cys Asp
    370                 375                 380

Leu Val Asn Val Asp Leu Asp Asp Cys Ile Phe Glu Gln
385                 390                 395
```

<210> SEQ ID NO 24
<211> LENGTH: 736
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

```
Thr Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95
```

-continued

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Val Ala Ser Gly Gly Gly
        195                 200                 205

Ala Pro Val Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510
```

```
Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 25
<211> LENGTH: 735
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

```
Thr Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125
```

-continued

```
Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Val Ala Thr Gly Ser Gly
        195                 200                 205

Ala Pro Val Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540
```

Gln Gly Ser Glu Lys Thr Asn Val Asp Ile Glu Lys Val Met Ile Thr
545 550 555 560

Asp Glu Glu Glu Ile Arg Thr Thr Asn Pro Val Ala Thr Glu Gln Tyr
565 570 575

Gly Ser Val Ser Thr Asn Leu Gln Arg Gly Asn Arg Gln Ala Ala Thr
580 585 590

Ala Asp Val Asn Thr Gln Gly Val Leu Pro Gly Met Val Trp Gln Asp
595 600 605

Arg Asp Val Tyr Leu Gln Gly Pro Ile Trp Ala Lys Ile Pro His Thr
610 615 620

Asp Gly His Phe His Pro Ser Pro Leu Met Gly Gly Phe Gly Leu Lys
625 630 635 640

His Pro Pro Pro Gln Ile Leu Ile Lys Asn Thr Pro Val Pro Ala Asn
645 650 655

Pro Ser Thr Thr Phe Ser Ala Ala Lys Phe Ala Ser Phe Ile Thr Gln
660 665 670

Tyr Ser Thr Gly Gln Val Ser Val Glu Ile Glu Trp Glu Leu Gln Lys
675 680 685

Glu Asn Ser Lys Arg Trp Asn Pro Glu Ile Gln Tyr Thr Ser Asn Tyr
690 695 700

Asn Lys Ser Val Asn Val Asp Phe Thr Val Asp Thr Asn Gly Val Tyr
705 710 715 720

Ser Glu Pro Arg Pro Ile Gly Thr Arg Tyr Leu Thr Arg Asn Leu
725 730 735

<210> SEQ ID NO 26
<211> LENGTH: 736
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

Leu Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Val Pro Gln Pro
20 25 30

Lys Ala Asn Gln Gln His Gln Asp Asn Arg Arg Gly Leu Val Leu Pro
35 40 45

Gly Tyr Lys Tyr Leu Gly Pro Phe Asn Gly Leu Asp Lys Gly Glu Pro
50 55 60

Val Asn Glu Ala Asp Ala Ala Ala Leu Glu His Asp Lys Ala Tyr Asp
65 70 75 80

Arg Gln Leu Asp Ser Gly Asp Asn Pro Tyr Leu Lys Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Ile Leu Glu Pro
115 120 125

Leu Gly Leu Val Glu Glu Ala Ala Lys Thr Ala Pro Gly Lys Lys Arg
130 135 140

Pro Val Asp Gln Ser Pro Gln Glu Pro Asp Ser Ser Ser Gly Val Gly
145 150 155 160

-continued

```
Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Val Ala Ser Gly Gly Gly
        195                 200                 205

Ala Pro Val Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575
```

Tyr Gly Thr Val Ala Asn Asn Leu Gln Ser Ser Asn Thr Ala Pro Thr
580 585 590

Thr Arg Thr Val Asn Asp Gln Gly Ala Leu Pro Gly Met Val Trp Gln
595 600 605

Asp Arg Asp Val Tyr Leu Gln Gly Pro Ile Trp Ala Lys Ile Pro His
610 615 620

Thr Asp Gly His Phe His Pro Ser Pro Leu Met Gly Gly Phe Gly Leu
625 630 635 640

Lys His Pro Pro Pro Gln Ile Met Ile Lys Asn Thr Pro Val Pro Ala
645 650 655

Asn Pro Pro Thr Thr Phe Ser Pro Ala Lys Phe Ala Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Asn Lys Ser Val Asn Val Asp Phe Thr Val Asp Thr Asn Gly Val
705 710 715 720

Tyr Ser Glu Pro Arg Pro Ile Gly Thr Arg Tyr Leu Thr Arg Asn Leu
725 730 735

<210> SEQ ID NO 27
<211> LENGTH: 736
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

Leu Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Phe Asn Gly Leu Asp Lys Gly Glu Pro
50 55 60

Val Asn Glu Ala Asp Ala Ala Ala Leu Glu His Asp Lys Ala Tyr Asp
65 70 75 80

Arg Gln Leu Asp Ser Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

-continued

```
Ala Ala Pro Ser Gly Val Gly Ser Leu Thr Val Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605
```

Asp Arg Asp Val Tyr Leu Gln Gly Pro Ile Trp Ala Lys Ile Pro His
610 615 620

Thr Asp Gly Asn Phe His Pro Ser Pro Leu Met Gly Gly Phe Gly Met
625 630 635 640

Lys His Pro Pro Pro Gln Ile Leu Ile Lys Asn Thr Pro Val Pro Ala
645 650 655

Asp Pro Pro Thr Ala Phe Asn Lys Asp Lys Leu Asn Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Tyr Lys Ser Asn Asn Val Glu Phe Ala Val Asn Thr Glu Gly Val
705 710 715 720

Tyr Ser Glu Pro Arg Pro Ile Gly Thr Arg Tyr Leu Thr Arg Asn Leu
725 730 735

<210> SEQ ID NO 28
<211> LENGTH: 52
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (44)..(44)
<223> OTHER INFORMATION: Any amino acid
<220> FEATURE:
<221> NAME/KEY: MOD_RES
<222> LOCATION: (47)..(47)
<223> OTHER INFORMATION: Any amino acid

<400> SEQUENCE: 28

Asp Ser Ser Ser Gly Ile Gly Lys Ser Gly Gln Gln Pro Ala Xaa Lys
1 5 10 15

Arg Leu Asn Phe Gly Gln Thr Gly Asp Ser Glu Ser Val Pro Asp Pro
20 25 30

Gln Pro Leu Gly Glu Pro Pro Ala Ala Pro Ser Xaa Val Gly Xaa Asn
35 40 45

Thr Met Ala Ser
50

<210> SEQ ID NO 29
<211> LENGTH: 52
<212> TYPE: PRT
<213> ORGANISM: Adeno-associated virus 3B

<400> SEQUENCE: 29

Asp Ser Ser Ser Gly Val Gly Lys Ser Gly Lys Gln Pro Ala Arg Lys
1 5 10 15

Arg Leu Asn Phe Gly Gln Thr Gly Asp Ser Glu Ser Val Pro Asp Pro
20 25 30

```
Gln Pro Leu Gly Glu Pro Pro Ala Ala Pro Thr Ser Leu Gly Ser Asn
        35                  40                  45

Thr Met Ala Ser
    50


<210> SEQ ID NO 30
<211> LENGTH: 44
<212> TYPE: PRT
<213> ORGANISM: Adeno-associated virus 5

<400> SEQUENCE: 30

Lys Lys Ala Arg Thr Glu Glu Asp Ser Lys Pro Ser Thr Ser Ser Asp
1               5                   10                  15

Ala Glu Ala Gly Pro Ser Gly Ser Gln Gln Leu Gln Ile Pro Ala Gln
            20                  25                  30

Pro Ala Ser Ser Leu Gly Ala Asp Thr Met Ser Ala
        35                  40


<210> SEQ ID NO 31
<211> LENGTH: 52
<212> TYPE: PRT
<213> ORGANISM: Adeno-associated virus 6

<400> SEQUENCE: 31

Asp Ser Ser Ser Gly Ile Gly Lys Thr Gly Gln Gln Pro Ala Lys Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Thr Pro Ala Ala Val Gly Pro Thr
        35                  40                  45

Thr Met Ala Ser
    50


<210> SEQ ID NO 32
<211> LENGTH: 52
<212> TYPE: PRT
<213> ORGANISM: Adeno-associated virus 8

<400> SEQUENCE: 32

Asp Ser Ser Thr Gly Ile Gly Lys Lys Gly Gln Gln Pro Ala Arg Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Ala Pro Ser Gly Val Gly Pro Asn
        35                  40                  45

Thr Met Ala Ala
    50


<210> SEQ ID NO 33
<211> LENGTH: 52
<212> TYPE: PRT
<213> ORGANISM: Adeno-associated virus 9

<400> SEQUENCE: 33

Asp Ser Ser Ala Gly Ile Gly Lys Ser Gly Ala Gln Pro Ala Lys Lys
1               5                   10                  15

Arg Leu Asn Phe Gly Gln Thr Gly Asp Thr Glu Ser Val Pro Asp Pro
            20                  25                  30
```

```
Gln Pro Ile Gly Glu Pro Pro Ala Ala Pro Ser Gly Val Gly Ser Leu
        35                  40                  45

Thr Met Ala Ser
    50


<210> SEQ ID NO 34
<211> LENGTH: 51
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (15)..(15)
<223> OTHER INFORMATION: Any amino acid

<400> SEQUENCE: 34

Asp Ser Ser Ser Gly Ile Gly Lys Lys Gly Gln Gln Pro Ala Xaa Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Ala Pro Ser Gly Val Gly Ser Asn
        35                  40                  45

Thr Met Ala
    50


<210> SEQ ID NO 35
<211> LENGTH: 51
<212> TYPE: PRT
<213> ORGANISM: Adeno-associated virus 1

<400> SEQUENCE: 35

Asp Ser Ser Ser Gly Ile Gly Lys Thr Gly Gln Gln Pro Ala Lys Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Thr Pro Ala Ala Val Gly Pro Thr
        35                  40                  45

Thr Met Ala
    50


<210> SEQ ID NO 36
<211> LENGTH: 51
<212> TYPE: PRT
<213> ORGANISM: Adeno-associated virus 2

<400> SEQUENCE: 36

Asp Ser Ser Ser Gly Thr Gly Lys Ala Gly Gln Gln Pro Ala Arg Lys
1               5                   10                  15

Arg Leu Asn Phe Gly Gln Thr Gly Asp Ala Asp Ser Val Pro Asp Pro
            20                  25                  30

Gln Pro Leu Gly Gln Pro Pro Ala Ala Pro Ser Gly Leu Gly Thr Asn
        35                  40                  45

Thr Met Ala
    50


<210> SEQ ID NO 37
<211> LENGTH: 51
<212> TYPE: PRT
```

<213> ORGANISM: Adeno-associated virus 3B

<400> SEQUENCE: 37

```
Asp Ser Ser Ser Gly Val Gly Lys Ser Gly Lys Gln Pro Ala Arg Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Ala Pro Thr Ser Leu Gly Ser Asn
        35                  40                  45

Thr Met Ala
    50
```

<210> SEQ ID NO 38
<211> LENGTH: 46
<212> TYPE: PRT
<213> ORGANISM: Adeno-associated virus 4

<400> SEQUENCE: 38

```
Asp Ser Ser Thr Gly Ile Gly Lys Lys Gly Lys Gln Pro Ala Lys Lys
1               5                   10                  15

Lys Leu Val Phe Glu Asp Glu Thr Gly Ala Gly Asp Gly Pro Pro Glu
            20                  25                  30

Gly Ser Thr Ser Gly Ala Met Ser Asp Asp Ser Glu Met Arg
        35                  40                  45
```

<210> SEQ ID NO 39
<211> LENGTH: 51
<212> TYPE: PRT
<213> ORGANISM: Adeno-associated virus 7

<400> SEQUENCE: 39

```
Asp Ser Ser Thr Gly Ile Gly Lys Lys Gly Gln Gln Pro Ala Arg Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Ala Pro Ser Ser Val Gly Ser Gly
        35                  40                  45

Thr Val Ala
    50
```

<210> SEQ ID NO 40
<211> LENGTH: 51
<212> TYPE: PRT
<213> ORGANISM: Adeno-associated virus 8

<400> SEQUENCE: 40

```
Asp Ser Ser Thr Gly Ile Gly Lys Lys Gly Gln Gln Pro Ala Arg Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Ala Pro Ser Gly Val Gly Pro Asn
        35                  40                  45

Thr Met Ala
    50
```

<210> SEQ ID NO 41
<211> LENGTH: 51
<212> TYPE: PRT
<213> ORGANISM: Adeno-associated virus 9

<400> SEQUENCE: 41

Asp Ser Ser Ala Gly Ile Gly Lys Ser Gly Ala Gln Pro Ala Lys Lys
1               5                   10                  15

Arg Leu Asn Phe Gly Gln Thr Gly Asp Thr Glu Ser Val Pro Asp Pro
            20                  25                  30

Gln Pro Ile Gly Glu Pro Pro Ala Ala Pro Ser Gly Val Gly Ser Leu
        35                  40                  45

Thr Met Ala
    50

<210> SEQ ID NO 42
<211> LENGTH: 51
<212> TYPE: PRT
<213> ORGANISM: Adeno-associated virus 10

<400> SEQUENCE: 42

Asp Ser Ser Thr Gly Ile Gly Lys Lys Gly Gln Gln Pro Ala Lys Lys
1               5                   10                  15

Arg Leu Asn Phe Gly Gln Thr Gly Glu Ser Glu Ser Val Pro Asp Pro
            20                  25                  30

Gln Pro Ile Gly Glu Pro Pro Ala Gly Pro Ser Gly Leu Gly Ser Gly
        35                  40                  45

Thr Met Ala
    50

<210> SEQ ID NO 43
<211> LENGTH: 46
<212> TYPE: PRT
<213> ORGANISM: Adeno-associated virus 11

<400> SEQUENCE: 43

Asp Ser Ser Ser Gly Ile Gly Lys Lys Gly Lys Gln Pro Ala Arg Lys
1               5                   10                  15

Arg Leu Asn Phe Glu Glu Asp Thr Gly Ala Gly Asp Gly Pro Pro Glu
            20                  25                  30

Gly Ser Asp Thr Ser Ala Met Ser Ser Asp Ile Glu Met Arg
        35                  40                  45

<210> SEQ ID NO 44
<211> LENGTH: 173
<212> TYPE: DNA
<213> ORGANISM: Adeno-associated virus 6

<400> SEQUENCE: 44
aagagccaga ctcctcctcg ggcattggca agacaggcca gcagcccgct aaaaagagac     60
tcaattttgg tcagactggc gagtccccga cccacaacct ctcggagaac ctccagcaac    120
ccccgctgct gtgggaccta ctacaatggc ttcaggcggt ggcgcaccaa tgg           173

<210> SEQ ID NO 45
<211> LENGTH: 183
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
aagagccaga ctcctccgcg ggtattggca aatcgggtgc acagcccgct aaaaagagac 60
tcaatttcgg tcagactggc gacacagagt cagtcccaga ccctcaacca atcggagaac 120
ctcccgcagc cccctcaggt gtgggatctc ttacaatggc ttcaggcggt ggcgcaccaa 180
tgg 183

<210> SEQ ID NO 46
<211> LENGTH: 57
<212> TYPE: PRT
<213> ORGANISM: Adeno-associated virus 6

<400> SEQUENCE: 46

Pro Gln Glu Pro Asp Ser Ser Ser Gly Ile Gly Lys Thr Gly Gln Gln
1 5 10 15

Pro Ala Lys Lys Arg Leu Asn Phe Gly Gln Thr Gly Asp Ser Glu Ser
20 25 30

Val Pro Asp Pro Gln Pro Leu Gly Glu Pro Pro Ala Thr Pro Ala Ala
35 40 45

Val Gly Pro Thr Thr Met Ala Ser Gly
50 55

<210> SEQ ID NO 47
<211> LENGTH: 57
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 47

Pro Gln Glu Pro Asp Ser Ser Ala Gly Ile Gly Lys Ser Gly Ala Gln
1 5 10 15

Pro Ala Lys Lys Arg Leu Asn Phe Gly Gln Thr Gly Asp Thr Glu Ser
20 25 30

Val Pro Asp Pro Gln Pro Ile Gly Glu Pro Pro Ala Ala Pro Ser Gly
35 40 45

Val Gly Ser Leu Thr Met Ala Ser Gly
50 55

<210> SEQ ID NO 48
<211> LENGTH: 57
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 48

Pro Gln Glu Pro Asp Ser Ser Ser Gly Ile Gly Lys Thr Gly Gln Gln
1 5 10 15

Pro Ala Lys Lys Arg Leu Asn Phe Gly Gln Thr Gly Asp Thr Glu Ser
20 25 30

Val Pro Asp Pro Gln Pro Ile Gly Glu Pro Pro Ala Ala Pro Ser Gly
35 40 45

Val Gly Ser Leu Thr Met Ala Ser Gly
50 55

```
<210> SEQ ID NO 49
<211> LENGTH: 57
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Pro Gln Glu Pro Asp Ser Ser Ser Gly Ile Gly Lys Thr Gly Gln Gln
1               5                   10                  15

Pro Ala Lys Lys Arg Leu Asn Phe Gly Gln Thr Gly Asp Thr Glu Ser
            20                  25                  30

Val Pro Asp Pro Gln Pro Ile Gly Glu Pro Pro Ala Ala Pro Ser Gly
        35                  40                  45

Val Gly Pro Thr Thr Met Ala Ser Gly
    50                  55


<210> SEQ ID NO 50
<211> LENGTH: 57
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Pro Gln Glu Pro Asp Ser Ser Ser Gly Ile Gly Lys Thr Gly Gln Gln
1               5                   10                  15

Pro Ala Lys Lys Arg Leu Asn Phe Gly Gln Thr Gly Asp Ser Glu Ser
            20                  25                  30

Val Pro Asp Pro Gln Pro Leu Gly Glu Pro Pro Ala Ala Pro Ser Gly
        35                  40                  45

Val Gly Ser Leu Thr Met Ala Ser Gly
    50                  55


<210> SEQ ID NO 51
<211> LENGTH: 57
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Pro Gln Glu Pro Asp Ser Ser Ala Gly Ile Gly Lys Ser Gly Ala Gln
1               5                   10                  15

Pro Ala Lys Lys Arg Leu Asn Phe Gly Gln Thr Gly Asp Ser Glu Ser
            20                  25                  30

Val Pro Asp Pro Gln Pro Leu Gly Glu Pro Pro Ala Thr Pro Ala Ala
        35                  40                  45

Val Gly Pro Thr Thr Met Ala Ser Gly
    50                  55


<210> SEQ ID NO 52
<211> LENGTH: 150
<212> TYPE: DNA
<213> ORGANISM: Adeno-associated virus 6
```

<400> SEQUENCE: 52
gccagcagcc cgctaaaaag agactcaatt ttggtcagac tggcgactca gagtcagtcc 60
ccgacccaca acctctcgga gaacctccag caaccccgc tgctgtggga cctactacaa 120
tggcttcagg cggtggcgca ccaatggcag 150

<210> SEQ ID NO 53
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 53
gtgcacagcc cgctaaaaag agactcaatt tcggtcagac tggcgacaca gagtcagtcc 60
cagaccctca accaatcgga gaacctcccg cagcccctc aggtgtggga tctcttacaa 120
tggcttcagg cggtggcgca ccaatggcag 150

<210> SEQ ID NO 54
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 54
gccagcagcc cgctaaaaag agactcaatt ttggtcagac tggcgacaca gagtcagtcc 60
ccgacccaca acctatcgga gaacctccag cagcccctc aggtgtggga tctcttacaa 120
tggcttcagg cggtggcgca ccaatggcag 150

<210> SEQ ID NO 55
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 55
gccagcagcc cgctaaaaag agactcaatt ttggtcagac tggcgacaca gagtcagtcc 60
ccgacccaca acctatcgga gaacctccag cagcccctc aggtgtggga cctactacaa 120
tggcttcagg cggtggcgca ccaatggcag 150

<210> SEQ ID NO 56
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 56
gccagcagcc cgctaaaaag agactcaatt ttggtcagac tggcgactca gagtcagtcc 60
ccgacccaca acctctcgga gaacctccag cagccccctc aggtgtggga tctcttacaa 120
tggcttcagg cggtggcgca ccaatggcag 150

<210> SEQ ID NO 57
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57
gcgcgcagcc cgctaaaaag agactcaatt ttggtcagac tggcgactca gagtcagtcc 60
ccgacccaca acctctcgga gaacctccag caaccccccgc tgctgtggga cctactacaa 120
tggcttcagg cggtggcgca ccaatggcag 150

<210> SEQ ID NO 58
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 58

Met Ala Thr Gln Ser Gln Ser Pro Thr Leu Asn Leu Ser Glu Asn Leu
1 5 10 15

Gln Gln Pro Pro Leu Val Trp Asp Leu Leu Gln Trp Leu Gln
20 25 30

<210> SEQ ID NO 59
<211> LENGTH: 30
<212> TYPE: PRT
<213> ORGANISM: Adeno-associated virus 1

<400> SEQUENCE: 59

Met Ala Thr Gln Ser Gln Ser Pro Ile His Asn Leu Ser Glu Asn Leu
1 5 10 15

Gln Gln Pro Pro Leu Leu Trp Asp Leu Leu Gln Trp Leu Gln
20 25 30

<210> SEQ ID NO 60
<211> LENGTH: 30
<212> TYPE: PRT
<213> ORGANISM: Adeno-associated virus 2

<400> SEQUENCE: 60

Met Glu Thr Gln Thr Gln Tyr Leu Thr Pro Ser Leu Ser Asp Ser His
1 5 10 15

Gln Gln Pro Pro Leu Val Trp Glu Leu Ile Arg Trp Leu Gln
20 25 30

<210> SEQ ID NO 61
<211> LENGTH: 30
<212> TYPE: PRT
<213> ORGANISM: Adeno-associated virus 3B

```
<400> SEQUENCE: 61

Met Ala Thr Gln Ser Gln Ser Gln Thr Leu Asn Leu Ser Glu Asn His
1               5                   10                  15

Gln Gln Pro Pro Gln Val Trp Asp Leu Ile Gln Trp Leu Gln
            20                  25                  30


<210> SEQ ID NO 62
<211> LENGTH: 24
<212> TYPE: PRT
<213> ORGANISM: Adeno-associated virus 4

<400> SEQUENCE: 62

Met Glu Gln Ala Thr Asp Pro Leu Arg Asp Gln Leu Pro Glu Pro Cys
1               5                   10                  15

Leu Met Thr Val Arg Cys Val Gln
            20


<210> SEQ ID NO 63
<211> LENGTH: 30
<212> TYPE: PRT
<213> ORGANISM: Adeno-associated virus 7

<400> SEQUENCE: 63

Met Ala Thr Gln Ser Gln Ser Pro Thr Leu Asn Leu Ser Glu Asn Leu
1               5                   10                  15

Gln Gln Arg Pro Leu Val Trp Asp Leu Val Gln Trp Leu Gln
            20                  25                  30


<210> SEQ ID NO 64
<211> LENGTH: 30
<212> TYPE: PRT
<213> ORGANISM: Adeno-associated virus 8

<400> SEQUENCE: 64

Met Ala Thr Gln Ser Gln Phe Gln Thr Leu Asn Leu Ser Glu Asn Leu
1               5                   10                  15

Gln Gln Arg Pro Leu Val Trp Asp Leu Ile Gln Trp Leu Gln
            20                  25                  30


<210> SEQ ID NO 65
<211> LENGTH: 30
<212> TYPE: PRT
<213> ORGANISM: Adeno-associated virus 10

<400> SEQUENCE: 65

Met Ala Ser Gln Ser Gln Ser Pro Thr Leu Asn Gln Ser Glu Asn His
1               5                   10                  15

Gln Gln Ala Pro Leu Val Trp Asp Leu Val Gln Trp Leu Gln
            20                  25                  30


<210> SEQ ID NO 66
<211> LENGTH: 24
<212> TYPE: PRT
<213> ORGANISM: Adeno-associated virus 11

<400> SEQUENCE: 66

Met Glu Pro Glu Thr Asp Pro Leu Lys Asp Gln Ile Pro Ala Pro Cys
1               5                   10                  15

Leu Gln Thr Leu Lys Cys Val Gln
            20
```

```
<210> SEQ ID NO 67
<211> LENGTH: 49
<212> TYPE: PRT
<213> ORGANISM: Adeno-associated virus 6
<220> FEATURE:
<221> NAME/KEY: VARIANT
<222> LOCATION: (14)..(14)
<223> OTHER INFORMATION: /replace="Met"
<220> FEATURE:
<221> NAME/KEY: SITE
<222> LOCATION: (1)..(49)
<223> OTHER INFORMATION: /note="Variant residues given in the sequence
      have no preference with respect to those in the annotations
      for variant positions"

<400> SEQUENCE: 67

Gly Gln Gln Pro Ala Lys Lys Arg Leu Asn Phe Gly Gln Leu Ala Thr
1               5                   10                  15

Gln Ser Gln Ser Pro Thr His Asn Leu Ser Glu Asn Leu Gln Gln Pro
            20                  25                  30

Pro Leu Leu Trp Asp Leu Leu Gln Trp Leu Gly Gly Gly Ala Pro Met
        35                  40                  45

Ala


<210> SEQ ID NO 68
<211> LENGTH: 49
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (14)..(14)
<223> OTHER INFORMATION: /replace="Met"
<220> FEATURE:
<221> NAME/KEY: SITE
<222> LOCATION: (1)..(49)
<223> OTHER INFORMATION: /note="Variant residues given in the sequence
      have no preference with respect to those in the annotations
      for variant positions"

<400> SEQUENCE: 68

Gly Ala Gln Pro Ala Lys Lys Arg Leu Asn Phe Gly Gln Leu Ala Thr
1               5                   10                  15

Gln Ser Gln Ser Gln Thr Leu Asn Gln Ser Glu Asn Leu Pro Gln Pro
            20                  25                  30

Pro Gln Val Trp Asp Leu Leu Gln Trp Leu Gly Gly Gly Ala Pro Met
        35                  40                  45

Ala


<210> SEQ ID NO 69
<211> LENGTH: 49
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (14)..(14)
<223> OTHER INFORMATION: /replace="Met"
<220> FEATURE:
<221> NAME/KEY: SITE
<222> LOCATION: (1)..(49)
```

```
<223> OTHER INFORMATION: /note="Variant residues given in the sequence
      have no preference with respect to those in the annotations
      for variant positions"

<400> SEQUENCE: 69

Gly Gln Gln Pro Ala Lys Lys Arg Leu Asn Phe Gly Gln Leu Ala Thr
1               5                   10                  15

Gln Ser Gln Ser Pro Thr His Asn Leu Ser Glu Asn Leu Gln Gln Pro
            20                  25                  30

Pro Gln Val Trp Asp Leu Leu Gln Trp Leu Gly Gly Gly Ala Pro Met
        35                  40                  45

Ala


<210> SEQ ID NO 70
<211> LENGTH: 49
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (14)..(14)
<223> OTHER INFORMATION: /replace="Met"
<220> FEATURE:
<221> NAME/KEY: SITE
<222> LOCATION: (1)..(49)
<223> OTHER INFORMATION: /note="Variant residues given in the sequence
      have no preference with respect to those in the annotations
      for variant positions"

<400> SEQUENCE: 70

Gly Gln Gln Pro Ala Lys Lys Arg Leu Asn Phe Gly Gln Leu Ala Thr
1               5                   10                  15

Gln Ser Gln Ser Pro Thr His Asn Leu Ser Glu Asn Leu Gln Gln Pro
            20                  25                  30

Pro Gln Val Trp Asp Leu Leu Gln Trp Leu Gly Gly Gly Ala Pro Met
        35                  40                  45

Ala


<210> SEQ ID NO 71
<211> LENGTH: 49
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (14)..(14)
<223> OTHER INFORMATION: /replace="Met"
<220> FEATURE:
<221> NAME/KEY: SITE
<222> LOCATION: (1)..(49)
<223> OTHER INFORMATION: /note="Variant residues given in the sequence
      have no preference with respect to those in the annotations
      for variant positions"
```

<400> SEQUENCE: 71

```
Gly Gln Gln Pro Ala Lys Lys Arg Leu Asn Phe Gly Gln Leu Ala Thr
1               5                   10                  15

Gln Ser Gln Ser Pro Thr His Asn Leu Ser Glu Asn Leu Gln Gln Pro
            20                  25                  30

Pro Gln Val Trp Asp Leu Leu Gln Trp Leu Gly Gly Gly Ala Pro Met
        35                  40                  45

Ala
```

<210> SEQ ID NO 72
<211> LENGTH: 49
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (14)..(14)
<223> OTHER INFORMATION: /replace="Met"
<220> FEATURE:
<221> NAME/KEY: SITE
<222> LOCATION: (1)..(49)
<223> OTHER INFORMATION: /note="Variant residues given in the sequence have no preference with respect to those in the annotations for variant positions"

<400> SEQUENCE: 72

```
Gly Ala Gln Pro Ala Lys Lys Arg Leu Asn Phe Gly Gln Leu Ala Thr
1               5                   10                  15

Gln Ser Gln Ser Pro Thr His Asn Leu Ser Glu Asn Leu Gln Gln Pro
            20                  25                  30

Pro Leu Leu Trp Asp Leu Leu Gln Trp Leu Gly Gly Gly Ala Pro Met
        35                  40                  45

Ala
```

<210> SEQ ID NO 73
<211> LENGTH: 51
<212> TYPE: PRT
<213> ORGANISM: Adeno-associated virus 6

<400> SEQUENCE: 73

```
Asp Ser Ser Ser Gly Ile Gly Lys Thr Gly Gln Gln Pro Ala Lys Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Thr Pro Ala Ala Val Gly Pro Thr
        35                  40                  45

Thr Met Ala
    50
```